US009358269B2

(12) United States Patent
Endo

(10) Patent No.: US 9,358,269 B2
(45) Date of Patent: Jun. 7, 2016

(54) METHOD FOR TREATING DERMATITIS AND IMPROVING SKIN TEXTURE USING NATRIURETIC PEPTIDES

(71) Applicant: IGISU Co., Ltd., Tokyo (JP)

(72) Inventor: Kyoko Endo, Sendai (JP)

(73) Assignee: IGISU CO., LTD, Tokyo (JP)

( * ) Notice: Subject to any disclaimer, the term of this patent is extended or adjusted under 35 U.S.C. 154(b) by 0 days.

(21) Appl. No.: 14/016,637

(22) Filed: Sep. 3, 2013

(65) Prior Publication Data

US 2014/0072520 A1 Mar. 13, 2014

Related U.S. Application Data

(62) Division of application No. 13/386,528, filed as application No. PCT/JP2010/062459 on Jul. 23, 2010, now abandoned.

(30) Foreign Application Priority Data

Jul. 23, 2009 (JP) ................................. 2009-172589
Jun. 11, 2010 (JP) ................................. 2010-134600

(51) Int. Cl.
*A61K 9/06* (2006.01)
*A61K 38/17* (2006.01)
*A61Q 19/00* (2006.01)
*A61K 38/22* (2006.01)
*A61K 8/64* (2006.01)
*A61K 9/00* (2006.01)

(52) U.S. Cl.
CPC . *A61K 38/22* (2013.01); *A61K 8/64* (2013.01); *A61K 9/0014* (2013.01); *A61K 9/06* (2013.01); *A61K 38/2242* (2013.01); *A61Q 19/00* (2013.01)

(58) Field of Classification Search
None
See application file for complete search history.

(56) References Cited

U.S. PATENT DOCUMENTS

| | | | |
|---|---|---|---|
| 5,114,923 A | 5/1992 | Seilhamer et al. | |
| 5,583,108 A | 12/1996 | Wei et al. | |
| 6,028,055 A | 2/2000 | Lowe et al. | |
| 6,707,211 B2* | 3/2004 | Oohashi et al. | 310/179 |
| 6,818,619 B2* | 11/2004 | Burnett et al. | 514/9.7 |
| 7,384,917 B2* | 6/2008 | Burnett et al. | 514/12.4 |
| 7,648,962 B2 | 1/2010 | James et al. | |
| 7,964,564 B2* | 6/2011 | Burnett et al. | 514/12.4 |
| 8,198,242 B2* | 6/2012 | Wendt et al. | 514/12.4 |
| 8,354,496 B2* | 1/2013 | Pan et al. | 530/300 |
| 8,377,884 B2* | 2/2013 | Wendt et al. | 514/16.7 |
| 8,642,550 B2* | 2/2014 | Dickey et al. | 514/12.4 |
| 2006/0034903 A1 | 2/2006 | Maa et al. | |
| 2008/0070858 A1 | 3/2008 | Mohapatra | |

FOREIGN PATENT DOCUMENTS

| | | |
|---|---|---|
| CN | 101232874 A | 7/2008 |
| EP | 0497368 A1 | 8/1992 |
| EP | 1118329 A1 | 7/2001 |
| EP | 1637162 A1 | 3/2006 |
| EP | 1743653 A1 | 1/2007 |
| EP | 1759710 A1 | 3/2007 |
| EP | 1810716 A1 | 7/2007 |
| JP | 5-207891 A | 8/1993 |
| JP | 6-9688 A | 1/1994 |
| JP | 2000-169387 A | 6/2000 |
| JP | 2007-525213 A | 9/2007 |
| JP | 2007-525957 A | 9/2007 |
| JP | 2008-509746 A | 4/2008 |
| JP | 2008-162987 A | 7/2008 |
| JP | 2008-540509 A | 11/2008 |
| JP | 2010-500032 A | 1/2010 |
| JP | 2010-168283 A | 8/2010 |
| JP | 2010-539022 A | 12/2010 |
| JP | 2308889 A | 4/2011 |
| WO | WO 98/52599 A1 | 11/1998 |
| WO | WO-2004/022003 A2 | 3/2004 |
| WO | WO 2004/110489 A1 | 12/2004 |
| WO | WO 2005/072055 A2 | 8/2005 |
| WO | WO 2005/094889 A1 | 10/2005 |
| WO | WO 2005/094890 A1 | 10/2005 |
| WO | WO 2006/020841 A2 | 2/2006 |
| WO | WO-2007/023396 A2 | 3/2007 |

(Continued)

OTHER PUBLICATIONS

PubMed-B-type natriuretic protein, accessed Feb. 25, 2015.*
Pubmed-C-type natriuretic protein, accessed Feb. 25, 2015.*
J. Allergy Clin. Immunol Suppl. 1 (Feb. 2003), Abstracts, vol. 111, No. 2, p. S309.
Kumar et al., "Atrial natriuretic peptide gene transfer by means of intranasal administration attenuates airway reactivity in a mouse model of allergic sensitization," J. Allergy Clin. Immunol. (2002), vol. 110, pp. 879-882.
Reichert, S. and A. Ignaszewski, "Molecular and physiological effects of nesiritide," Can. J. Cardiol. (Jul. 2008), vol. 24, Suppl. B, pp. 15B-18B.

(Continued)

*Primary Examiner* — Elly-Gerald Stoica
(74) *Attorney, Agent, or Firm* — Birch, Stewart, Kolasch & Birch, LLP

(57) ABSTRACT

The problem to be solved by the present invention is to provide a safe and efficacious therapeutic agent for dermatitis which is not only safe and efficacious for patients with dermatitis, in particular atopic dermatitis, but also significantly effective for severe cases that are judged to be intractable by conventional external preparations, and which is also safely applicable to affected areas such as the face and neck, as well as to subjects with sensitive skin, such as infants and females. Furthermore, the invention aims to provide an external preparation that is efficacious as skin care cosmetics having effects to improve elasticity and wrinkles of the skin, moisturizing effects, and hair-growth effects. The means for solving the problem is a skin external-preparation composition, in particular, a therapeutic agent for dermatitis or a skin texture-improving agent, having C-type natriuretic peptide (CNP) or B-type natriuretic peptide (BNP) as the active ingredient.

20 Claims, 16 Drawing Sheets

(56) References Cited

FOREIGN PATENT DOCUMENTS

| WO | WO-2008/021872 A1 | 2/2008 | | |
|---|---|---|---|---|
| WO | WO-2008/032450 A1 | 3/2008 | | |
| WO | WO-2008/133349 A1 | 11/2008 | | |
| WO | WO-2008/140125 A1 | 11/2008 | | |
| WO | WO 2009/033724 A | 3/2009 | | |
| WO | WO 2009/033807 A2 | 3/2009 | | |
| WO | WO2009033724 | * | 3/2009 | ............. A61K 38/17 |
| WO | WO2009033807 | * | 3/2009 | ............. A61K 38/17 |
| WO | WO 2009/046861 A1 | 4/2009 | | |

OTHER PUBLICATIONS

Agoston et al., "Dexamethasone stimulates expression of C-type Natriuretic Peptide in chondrocytes," BMC Musculoskeletal Disorders, 2006, vol. 7:87, pp. 1-7.

Chiurchiu et al., "Brain Natriuretic Peptide (BNP) regulates the production of inflammatory mediators in human THP-1 macrophages," Regulatory Peptides, 2008, vol. 148, pp. 26-32.

Chusho et al., "Dwarfism and early death in mice lacking C-type natriuretic peptide," PNAS, 2001, vol. 98, No. 7, pp. 4016-4021.

Gelmetti et al., "The value of SCORAD and beyond. Towards a standardized evaluation of severity?," Allergy, 2004, vol. 59(Suppl. 78), pp. 61-65.

Guidelines for Management of Atopic Dermatitis by the Japanese Dermatological Association, 2009.

Guidelines for the Treatment of Atopic Dermatitis by the Scientific Research Division of the Health and Welfare Ministry of Japan, 2005.

Kiemer et al., "The atrial natriuretic peptide regulates the production of inflammatory mediators in macrophages," Ann Rheum Dis., 2001, vol. 60, pp. iii68-iii70.

Kubo et al., "C-type natriuretic peptide is synthesized and secreted from leukemia cell lines, peripheral blood cells, and peritoneal macrophages," Experimental Hematology, 2001, vol. 29, pp. 609-615.

Kuroski de Bold, et al., "Cardiac hormones ANF and BNP modulate proliferation in the unidirectional mixed lymphocyte reaction," The Journal of Heart and Lung Transplantation, 2010, vol. 29, No. 3, pp. 323-326.

Meirovich et al., "Relationship Between Natriuretic Peptides and Inflammation: Proteomic Evidence Obtained During Acute Cellular Cardiac Allograft Rejection in Humans," The Journal of Heart and Lung Transplantation, 2008, vol. 27, No. 1, pp. 31-37.

Obata et al., "CNP infusion attenuates cardiac dysfunction and inflammation in myocarditis," Biochemical and Biophysical Research Communications, 2007, vol. 356, pp. 60-66.

Package Insert of Protopic (Tacrolimus hydrate), Astellas Pharma Inc., 2011.

Scotland et al., "C-Type natriuretic peptide inhibits leukocyte recruitment and platelet-leukocyte interactions via suppresion of P-selectin expression," PNAS, 2005, vol. 102, No. 40, pp. 14452-14457.

The Journal of Therapy (Chiryo), 1995, vol. 77, No. 4, pp. 1339-1344.

Yoshibayashi et al., "Brain natriuretic peptide versus atrial natriuretic peptide—physiological and pathophysiological significance in children and adults: a review," European Journal of Endocrinology, 1996, vol. 135, pp. 265-268.

Gene Bank (NCBI website), Accession No. O46541 (Version O46541.1), Locus: ANFB_Sheep, Sequence Updated: Jun. 1, 1998, Annotation Updated: Apr. 1, 2015, 2 pages.

Gene Bank (NCBI website), Accession No. P07634 (Version P07634.2), Locus: ANFB_Pig, Sequence Updated: Jul. 1, 1989, Annotation Updated: Dec. 9, 2015, 3 pages.

Gene Bank (NCBI website), Accession No. P13204 (Version P13204.3), Locus: ANFB_Bovin, Sequence Updated: Mar. 21, 2012, Annotation Updated: Nov. 11, 2015, 3 pages.

Gene Bank (NCBI website), Accession No. P13205 (Version P13205.3), Locus: ANFB_Rat, Sequence Updated: Feb. 1, 1991, Annotation Updated: Nov. 11, 2015, 3 pages.

Gene Bank (NCBI website), Accession No. P16860 (Version P16860.1), Locus: ANFB_Human, Sequence Updated: Aug. 1, 1990, Annotation Updated: Nov. 11, 2015, 8 pages.

Gene Bank (NCBI website), Accession No. P18104 (Version P18104.2), Locus: ANFC_Pig, Sequence Updated: Aug. 1, 1991, Annotation Updated: Nov. 11, 2015, 3 pages.

Gene Bank (NCBI website), Accession No. P23582 (Version P23582.1), Locus: ANFC_Human, Sequence Updated: Nov. 1, 1991, Annotation Updated: Dec. 9, 2015, 4 pages.

Gene Bank (NCBI website), Accession No. P40753 (Version P40753.2), Locus: ANFB_Mouse, Sequence Updated: Nov. 1, 1995, Annotation Updated: Nov. 11, 2015, 4 pages.

Gene Bank (NCBI website), Accession No. P55207 (Version P55207.1), Locus: ANFC_Rat, Sequence Updated: Oct. 1, 1996, Annotation Updated: Nov. 11, 2015, 2 pages.

Gene Bank (NCBI website), Accession No. Q61839 (Version Q61839.1), Locus: ANFC_Mouse, Sequence Updated: Nov. 1, 1996, Annotation Updated: Dec. 9, 2015, 3 pages.

* cited by examiner

A

B

A          B

A          B

A          B

A                B

A                B

A

B

A

B

A

B

A

B

A

B

SEQUENCE LISTING

```
<160> NUMBER OF SEQ ID NOS: 32

<210> SEQ ID NO 1
<211> LENGTH: 53
<212> TYPE: PRT
<213> ORGANISM: Human
<220> FEATURE:
<221> NAME/KEY: misc_feature
<222> LOCATION: (1)..(53)
<223> OTHER INFORMATION: CNP-53, >sp|P23582|74-126

<400> SEQUENCE: 1

Asp Leu Arg Val Asp Thr Lys Ser Arg Ala Ala Trp Ala Arg Leu Leu
1               5                   10                  15

Gln Glu His Pro Asn Ala Arg Lys Tyr Lys Gly Ala Asn Lys Lys Gly
            20                  25                  30

Leu Ser Lys Gly Cys Phe Gly Leu Lys Leu Asp Arg Ile Gly Ser Met
        35                  40                  45

Ser Gly Leu Gly Cys
    50

<210> SEQ ID NO 2
<211> LENGTH: 53
<212> TYPE: PRT
<213> ORGANISM: Rat
<220> FEATURE:
<221> NAME/KEY: misc_feature
<222> LOCATION: (1)..(53)
<223> OTHER INFORMATION: CNP-53, >sp|P55207|74-126

<400> SEQUENCE: 2

Asp Leu Arg Val Asp Thr Lys Ser Arg Ala Ala Trp Ala Arg Leu Leu
1               5                   10                  15

His Glu His Pro Asn Ala Arg Lys Tyr Lys Gly Gly Asn Lys Lys Gly
            20                  25                  30

Leu Ser Lys Gly Cys Phe Gly Leu Lys Leu Asp Arg Ile Gly Ser Met
        35                  40                  45

Ser Gly Leu Gly Cys
    50

<210> SEQ ID NO 3
<211> LENGTH: 53
<212> TYPE: PRT
```

<213> ORGANISM: Mouse
<220> FEATURE:
<221> NAME/KEY: misc_feature
<222> LOCATION: (1)..(53)
<223> OTHER INFORMATION: CNP-53, >sp|Q61839|74-126

<400> SEQUENCE: 3

Asp Leu Arg Val Asp Thr Lys Ser Arg Ala Ala Trp Ala Arg Leu Leu
1               5                   10                  15

His Glu His Pro Asn Ala Arg Lys Tyr Lys Gly Gly Asn Lys Lys Gly
            20                  25                  30

Leu Ser Lys Gly Cys Phe Gly Leu Lys Leu Asp Arg Ile Gly Ser Met
        35                  40                  45

Ser Gly Leu Gly Cys
    50

<210> SEQ ID NO 4
<211> LENGTH: 53
<212> TYPE: PRT
<213> ORGANISM: Pig
<220> FEATURE:
<221> NAME/KEY: misc_feature
<222> LOCATION: (1)..(53)
<223> OTHER INFORMATION: CNP-53, >sp|P18104|74-126

<400> SEQUENCE: 4

Asp Leu Arg Val Asp Thr Lys Ser Arg Ala Ala Trp Ala Arg Leu Leu
1               5                   10                  15

His Glu His Pro Asn Ala Arg Lys Tyr Lys Gly Gly Asn Lys Lys Gly
            20                  25                  30

Leu Ser Lys Gly Cys Phe Gly Leu Lys Leu Asp Arg Ile Gly Ser Met
        35                  40                  45

Ser Gly Leu Gly Cys
    50

<210> SEQ ID NO 5
<211> LENGTH: 22
<212> TYPE: PRT
<213> ORGANISM: Human
<220> FEATURE:
<221> NAME/KEY: misc_feature
<222> LOCATION: (1)..(22)
<223> OTHER INFORMATION: CNP-22, >sp|P23582|105-126

<400> SEQUENCE: 5

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 6
<211> LENGTH: 22
<212> TYPE: PRT
<213> ORGANISM: Rat
<220> FEATURE:
<221> NAME/KEY: misc_feature
<222> LOCATION: (1)..(22)
<223> OTHER INFORMATION: CNP-22, >sp|P55207|105-126

<400> SEQUENCE: 6

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 7
<211> LENGTH: 22
<212> TYPE: PRT
<213> ORGANISM: Mouse
<220> FEATURE:
<221> NAME/KEY: misc_feature
<222> LOCATION: (1)..(22)
<223> OTHER INFORMATION: CNP-22, >sp|Q61839|105-126

<400> SEQUENCE: 7

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 8
<211> LENGTH: 22
<212> TYPE: PRT
<213> ORGANISM: Pig
<220> FEATURE:
<221> NAME/KEY: misc_feature
<222> LOCATION: (1)..(22)
<223> OTHER INFORMATION: CNP-22, >sp|P18104|105-126

<400> SEQUENCE: 8

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 9
<211> LENGTH: 29
<212> TYPE: PRT
<213> ORGANISM: Human
<220> FEATURE:
<221> NAME/KEY: misc_feature
<222> LOCATION: (1)..(29)
<223> OTHER INFORMATION: CNP-29, >sp|P23582|98-126

<400> SEQUENCE: 9

Tyr Lys Gly Ala Asn Lys Lys Gly Leu Ser Lys Gly Cys Phe Gly Leu
1               5                   10                  15

Lys Leu Asp Arg Ile Gly Ser Met Ser Gly Leu Gly Cys
            20                  25

<210> SEQ ID NO 10
<211> LENGTH: 29
<212> TYPE: PRT
<213> ORGANISM: Rat
<220> FEATURE:
<221> NAME/KEY: misc_feature
<222> LOCATION: (1)..(29)
<223> OTHER INFORMATION: CNP-29, >sp|P55207|98-126

<400> SEQUENCE: 10

Tyr Lys Gly Gly Asn Lys Lys Gly Leu Ser Lys Gly Cys Phe Gly Leu
1               5                   10                  15

Lys Leu Asp Arg Ile Gly Ser Met Ser Gly Leu Gly Cys
            20                  25

<210> SEQ ID NO 11
<211> LENGTH: 29
<212> TYPE: PRT
<213> ORGANISM: Mouse
<220> FEATURE:

```
<221> NAME/KEY: misc_feature
<222> LOCATION: (1)..(29)
<223> OTHER INFORMATION: CNP-29, >sp|Q61839|98-126

<400> SEQUENCE: 11

Tyr Lys Gly Gly Asn Lys Lys Gly Leu Ser Lys Gly Cys Phe Gly Leu
1               5                   10                  15

Lys Leu Asp Arg Ile Gly Ser Met Ser Gly Leu Gly Cys
            20                  25

<210> SEQ ID NO 12
<211> LENGTH: 29
<212> TYPE: PRT
<213> ORGANISM: Pig
<220> FEATURE:
<221> NAME/KEY: misc_feature
<222> LOCATION: (1)..(29)
<223> OTHER INFORMATION: CNP-29, >sp|P18104|98-126

<400> SEQUENCE: 12

Tyr Lys Gly Gly Asn Lys Lys Gly Leu Ser Lys Gly Cys Phe Gly Leu
1               5                   10                  15

Lys Leu Asp Arg Ile Gly Ser Met Ser Gly Leu Gly Cys
            20                  25

<210> SEQ ID NO 13
<211> LENGTH: 45
<212> TYPE: PRT
<213> ORGANISM: Mouse
<220> FEATURE:
<221> NAME/KEY: misc_feature
<222> LOCATION: (1)..(45)
<223> OTHER INFORMATION: BNP-45, >sp|P40753|77-121

<400> SEQUENCE: 13

Ser Gln Gly Ser Thr Leu Arg Val Gln Gln Arg Pro Gln Asn Ser Lys
1               5                   10                  15

Val Thr His Ile Ser Ser Cys Phe Gly His Lys Ile Asp Arg Ile Gly
            20                  25                  30

Ser Val Ser Arg Leu Gly Cys Asn Ala Leu Lys Leu Leu
        35                  40                  45

<210> SEQ ID NO 14
<211> LENGTH: 45
<212> TYPE: PRT
<213> ORGANISM: Rat
<220> FEATURE:
<221> NAME/KEY: misc_feature
<222> LOCATION: (1)..(45)
<223> OTHER INFORMATION: BNP-45, >sp|P13205|77-121

<400> SEQUENCE: 14

Ser Gln Asp Ser Ala Phe Arg Ile Gln Glu Arg Leu Arg Asn Ser Lys
1               5                   10                  15

Met Ala His Ser Ser Ser Cys Phe Gly Gln Lys Ile Asp Arg Ile Gly
            20                  25                  30

Ala Val Ser Arg Leu Gly Cys Asp Gly Leu Arg Leu Phe
        35                  40                  45

<210> SEQ ID NO 15
<211> LENGTH: 32
<212> TYPE: PRT
<213> ORGANISM: Human
<220> FEATURE:
<221> NAME/KEY: misc_feature
```

<222> LOCATION: (1)..(32)
<223> OTHER INFORMATION: BNP-32, >sp|P16860|103-134

<400> SEQUENCE: 15

Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
            20                  25                  30

<210> SEQ ID NO 16
<211> LENGTH: 32
<212> TYPE: PRT
<213> ORGANISM: Pig
<220> FEATURE:
<221> NAME/KEY: misc_feature
<222> LOCATION: (1)..(32)
<223> OTHER INFORMATION: BNP-32, >sp|P07634|100-131

<400> SEQUENCE: 16

Ser Pro Lys Thr Met Arg Asp Ser Gly Cys Phe Gly Arg Arg Leu Asp
1               5                   10                  15

Arg Ile Gly Ser Leu Ser Gly Leu Gly Cys Asn Val Leu Arg Arg Tyr
            20                  25                  30

<210> SEQ ID NO 17
<211> LENGTH: 26
<212> TYPE: PRT
<213> ORGANISM: Human
<220> FEATURE:
<221> NAME/KEY: misc_feature
<222> LOCATION: (1)..(26)
<223> OTHER INFORMATION: BNP-26, >sp|P16860|106-131

<400> SEQUENCE: 17

Met Val Gln Gly Ser Gly Cys Phe Gly Arg Lys Met Asp Arg Ile Ser
1               5                   10                  15

Ser Ser Ser Gly Leu Gly Cys Lys Val Leu
            20                  25

<210> SEQ ID NO 18
<211> LENGTH: 26
<212> TYPE: PRT
<213> ORGANISM: Pig
<220> FEATURE:
<221> NAME/KEY: misc_feature
<222> LOCATION: (1)..(26)
<223> OTHER INFORMATION: BNP-26, >sp|P07634|106-131

<400> SEQUENCE: 18

Asp Ser Gly Cys Phe Gly Arg Arg Leu Asp Arg Ile Gly Ser Leu Ser
1               5                   10                  15

Gly Leu Gly Cys Asn Val Leu Arg Arg Tyr
            20                  25

<210> SEQ ID NO 19
<211> LENGTH: 26
<212> TYPE: PRT
<213> ORGANISM: bovine
<220> FEATURE:
<221> NAME/KEY: misc_feature
<222> LOCATION: (1)..(26)
<223> OTHER INFORMATION: BNP-26, >sp|P13204|104-129

<400> SEQUENCE: 19

Asp Ser Gly Cys Phe Gly Arg Arg Leu Asp Arg Ile Gly Ser Leu Ser
1               5                   10                  15

```
Gly Leu Gly Cys Asn Val Leu Arg Arg Tyr
            20                  25

<210> SEQ ID NO 20
<211> LENGTH: 26
<212> TYPE: PRT
<213> ORGANISM: sheep
<220> FEATURE:
<221> NAME/KEY: misc_feature
<222> LOCATION: (1)..(26)
<223> OTHER INFORMATION: BNP-26, >sp|O46541|104-129

<400> SEQUENCE: 20

Asp Ser Gly Cys Phe Gly Arg Arg Leu Asp Arg Ile Gly Ser Leu Ser
1               5                   10                  15

Gly Leu Gly Cys Asn Val Leu Arg Arg Tyr
            20                  25

<210> SEQ ID NO 21
<211> LENGTH: 30
<212> TYPE: PRT
<213> ORGANISM: Human
<220> FEATURE:
<221> NAME/KEY: misc_feature
<222> LOCATION: (1)..(30)
<223> OTHER INFORMATION: BNP-30, >sp|P16860|103-132

<400> SEQUENCE: 21

Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg
            20                  25                  30

<210> SEQ ID NO 22
<211> LENGTH: 30
<212> TYPE: PRT
<213> ORGANISM: Human
<220> FEATURE:
<221> NAME/KEY: misc_feature
<222> LOCATION: (1)..(30)
<223> OTHER INFORMATION: BNP-30, >sp|P16860|104-133

<400> SEQUENCE: 22

Pro Lys Met Val Gln Gly Ser Gly Cys Phe Gly Arg Lys Met Asp Arg
1               5                   10                  15

Ile Ser Ser Ser Ser Gly Leu Gly Cys Lys Val Leu Arg Arg
            20                  25                  30

<210> SEQ ID NO 23
<211> LENGTH: 30
<212> TYPE: PRT
<213> ORGANISM: Human
<220> FEATURE:
<221> NAME/KEY: misc_feature
<222> LOCATION: (1)..(30)
<223> OTHER INFORMATION: BNP-30, >sp|P16860|105-134

<400> SEQUENCE: 23

Lys Met Val Gln Gly Ser Gly Cys Phe Gly Arg Lys Met Asp Arg Ile
1               5                   10                  15

Ser Ser Ser Ser Gly Leu Gly Cys Lys Val Leu Arg Arg His
            20                  25                  30

<210> SEQ ID NO 24
<211> LENGTH: 29
```

```
<212> TYPE: PRT
<213> ORGANISM: Human
<220> FEATURE:
<221> NAME/KEY: misc_feature
<222> LOCATION: (1)..(29)
<223> OTHER INFORMATION: BNP -29, >sp|P16860|103-131

<400> SEQUENCE: 24

Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu
            20                  25

<210> SEQ ID NO 25
<211> LENGTH: 29
<212> TYPE: PRT
<213> ORGANISM: Human
<220> FEATURE:
<221> NAME/KEY: misc_feature
<222> LOCATION: (1)..(29)
<223> OTHER INFORMATION: BNP -29, >sp|P16860|106-134

<400> SEQUENCE: 25

Met Val Gln Gly Ser Gly Cys Phe Gly Arg Lys Met Asp Arg Ile Ser
1               5                   10                  15

Ser Ser Ser Gly Leu Gly Cys Lys Val Leu Arg Arg His
            20                  25

<210> SEQ ID NO 26
<211> LENGTH: 28
<212> TYPE: PRT
<213> ORGANISM: Human
<220> FEATURE:
<221> NAME/KEY: misc_feature
<222> LOCATION: (1)..(28)
<223> OTHER INFORMATION: BNP -28, >sp|P16860|103-130

<400> SEQUENCE: 26

Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val
            20                  25

<210> SEQ ID NO 27
<211> LENGTH: 28
<212> TYPE: PRT
<213> ORGANISM: Human
<220> FEATURE:
<221> NAME/KEY: misc_feature
<222> LOCATION: (1)..(28)
<223> OTHER INFORMATION: BNP -28, >sp|P16860|105-132

<400> SEQUENCE: 27

Lys Met Val Gln Gly Ser Gly Cys Phe Gly Arg Lys Met Asp Arg Ile
1               5                   10                  15

Ser Ser Ser Ser Gly Leu Gly Cys Lys Val Leu Arg
            20                  25

<210> SEQ ID NO 28
<211> LENGTH: 28
<212> TYPE: PRT
<213> ORGANISM: Human
<220> FEATURE:
<221> NAME/KEY: misc_feature
<222> LOCATION: (1)..(28)
<223> OTHER INFORMATION: BNP -28, >sp|P16860|106-133
```

```
<400> SEQUENCE: 28

Met Val Gln Gly Ser Gly Cys Phe Gly Arg Lys Met Asp Arg Ile Ser
1               5                   10                  15

Ser Ser Ser Gly Leu Gly Cys Lys Val Leu Arg Arg
            20                  25

<210> SEQ ID NO 29
<211> LENGTH: 27
<212> TYPE: PRT
<213> ORGANISM: Human
<220> FEATURE:
<221> NAME/KEY: misc_feature
<222> LOCATION: (1)..(27)
<223> OTHER INFORMATION: BNP-27, >sp|P16860|105-131

<400> SEQUENCE: 29

Lys Met Val Gln Gly Ser Gly Cys Phe Gly Arg Lys Met Asp Arg Ile
1               5                   10                  15

Ser Ser Ser Ser Gly Leu Gly Cys Lys Val Leu
            20                  25

<210> SEQ ID NO 30
<211> LENGTH: 27
<212> TYPE: PRT
<213> ORGANISM: Human
<220> FEATURE:
<221> NAME/KEY: misc_feature
<222> LOCATION: (1)..(27)
<223> OTHER INFORMATION: BNP-27, >sp|P16860|106-132

<400> SEQUENCE: 30

Met Val Gln Gly Ser Gly Cys Phe Gly Arg Lys Met Asp Arg Ile Ser
1               5                   10                  15

Ser Ser Ser Gly Leu Gly Cys Lys Val Leu Arg
            20                  25

<210> SEQ ID NO 31
<211> LENGTH: 25
<212> TYPE: PRT
<213> ORGANISM: Human
<220> FEATURE:
<221> NAME/KEY: misc_feature
<222> LOCATION: (1)..(25)
<223> OTHER INFORMATION: BNP-25, >sp|P16860|107-131

<400> SEQUENCE: 31

Val Gln Gly Ser Gly Cys Phe Gly Arg Lys Met Asp Arg Ile Ser Ser
1               5                   10                  15

Ser Ser Gly Leu Gly Cys Lys Val Leu
            20                  25

<210> SEQ ID NO 32
<211> LENGTH: 24
<212> TYPE: PRT
<213> ORGANISM: Human
<220> FEATURE:
<221> NAME/KEY: misc_feature
<222> LOCATION: (1)..(24)
<223> OTHER INFORMATION: BNP-24, >sp|P16860|106-129
```

```
<400> SEQUENCE: 32

Met Val Gln Gly Ser Gly Cys Phe Gly Arg Lys Met Asp Arg Ile Ser
1               5                   10                  15

Ser Ser Ser Gly Leu Gly Cys Lys
            20
```

METHOD FOR TREATING DERMATITIS AND IMPROVING SKIN TEXTURE USING NATRIURETIC PEPTIDES

This application is a Divisional of Application No. 13/386,528, (now abandoned), which is a National Phase of PCT International Application No. PCT/JP2010/062459 filed on Jul 23, 2010, and which claims priority to patent application Nos. 2009-172589, filed in Japan on Jul 23, 2009 and 2010-134600, filed in Japan on Jun 11, 2010. The entire contents of all of the above applications are hereby incorporated by reference.

FIELD OF INVENTION

The present invention relates to a skin external-preparation composition comprising C-type natriuretic peptide (CNP) or B-type natriuretic peptide (BNP) as its active ingredient. In particular, the present invention relates to a therapeutic agent for skin disease or a skin texture-improving agent comprising C-type natriuretic peptide (CNP) or B-type natriuretic peptide (BNP) as its active ingredient.

BACKGROUND ART

1. Dermatitis:

Dermatitis is an inflammatory reaction of the skin, and is the most prevalent skin disease. Often in acute skin inflammations, clinically, edematous erythema is presented initially, followed by erythematous lesions with papules and serous papules, then formation of vesicles, pustules, erosions, crusts and scales, followed by healing process. When a skin inflammation becomes chronic, thickened skin, lichenification and pigmentations are observed, and they are often associated with itching.

Dermatitis includes contact dermatitis, atopic dermatitis, seborrheic dermatitis, nummular eczema, psoriasis, stasis dermatitis, dyshidrotic eczema, asteatotic eczema, autosensitization eczema, etc.

Of these, atopic dermatitis is induced by hypersensitive reaction to a foreign protein antigen, a substance derived from other organisms which exists as house dust in the environment, as well as the involvement of various other non-specific stimulatory responses and specific allergic reactions. It is characterized by pruritic eczema over wide areas of the body accompanied by dryness and abnormal barrier function of the skin, and many patients have atopic diathesis. Atopic dermatitis is an intractable, chronic inflammatory disease, which relapses between remission and exacerbation. It has been known that delayed reactions associated with infiltration of eosinophils and lymphocytes, and production of various cytokines at the site of inflammation are involved in the onset and chronicity of atopic dermatitis.

2. Treatment of Dermatitis:

Current treatments for atopic dermatitis involve elimination of onset/exacerbation factors and skin care, in combination with pharmacotherapy appropriate for symptoms, while steroid external preparations are most commonly used for treating dermatitis. Recently, tacrolimus, an immunosuppressive drug, has also been used for treating atopic dermatitis.

Despite their dramatic clinical effectiveness, however, steroid external preparations are drugs that elicit numerous side effects. Steroid external preparations are not always satisfactory due to their side effects, including skin thinning, atrophy, so-called "moon face" which results from fat deposition in the face, skin flush, hirsutism, and skin striae, etc. In particular, since affected areas in the face and neck have higher absorbability of drugs than other areas, when a steroid external preparation is applied to the face, etc., they are more susceptible to steroid dermatitis such as steroid-induced rosacea. Moreover, further application of steroid external preparations to control the redness of the skin in steroid dermatitis means that the patients suffer from a vicious cycle of continuous steroid use. This explains why many patients avoid application of steroid drugs to the face and neck. In addition to these adverse side effects and concerns with regard to the use of steroid external preparations, there are further complications with the use of steroid drugs on patients with fairly sensitive skin, including infants, children, women and the patients with concomitant diseases, with whom eczema and dermatitis are found frequently. In addition, the repeated and long-term use of steroid external preparations, which is necessary due to the chronic nature of inflammation in atopic dermatitis developed with a background of atopic diathesis, may result in steroid resistance, in which the steroid external preparations become less effective against dermatitis. Furthermore, patients who withdraw from long-term use of steroid external preparations often suffer from what is known as a "rebound phenomenon" characterized by aggressive recurrence of a worsened symptoms than prior to the treatment.

Other concerns with long-term use of steroid external preparations are skin flush and desquamation of the skin over the whole body, which often occur with the comorbidity of hair loss and swollen lymph nodes. In such conditions of erythroderma posteczematosa, the patients' social lives are severely disrupted.

Generally, steroids used for treating atopic dermatitis are classified as the "strongest", "very strong", "strong", "medium" and "weak" in order of their efficacy, and the choice depends on factors such as the body region, severity of the rash, age and the period of use. For atopic dermatitis treatment using steroids, it is recommended that a steroid of a rank that is sufficiently strong to suppress the inflammatory symptoms of atopic dermatitis is prescribed initially, which is then replaced by progressively weaker ranks of steroids once the symptoms are controlled, allowing the earliest withdrawal from the steroid use.

The "strongest" rank steroids include: clobetasol propionate and diflorasone diacetate, and "very strong" steroids include mometasone furoate, betamethasone butyrate propionate, fluocinonide, betamethasone dipropionate, difluprednate, budesonide, amcinonide, diflucortolone valerate, and hydrocortisone butyrate propionate. In addition, the "strong" rank steroids includes: deprodone propionate, dexamethasone propionate, dexamethasone valerate, halcinonide, betamethasone valerate, beclomethasone propionate, fluocinolone acetonide, etc.; and "medium" rank steroids include: prednisolone valerate acetate, triamcinolone acetonide, flumethasone pivalate, alclometasone propionate, clobetasone butyrate, and hydrocortisone butyrate. The "weak" rank steroids include: predonisolone and hydrocortisone acetate.

Patients with chronic atopic dermatitis due to repeated recurrence are often found to have a history of use of multiple steroids belonging to either the "strongest" or "very strong" rank.

On the other hand, the alternative external preparation available, i.e., tacrolimus, is an immunosuppressive agent, and hence it is not applicable to children with 6 years old of age or younger, women who are or may be pregnant, and patients with renal disorders. The application of tacrolimus also significantly increases the risk of complication of herpes virus infection. This is thought to be due to the effect of the disturbance in the barrier function of the skin suffering from dryness, combined with the steroid-induced depression in the local immune functions. More seriously, incidence of malignant tumors has been recently reported in infants and children, making the safety of tacrolimus questionable. In addition, some patients find some of the local strong irritative side effects including burning sensation and itching, which inevitably occur upon external application of tacrolimus, unbearable.

For the reasons above, a safe, effective, adverse effect-free therapeutic agent for dermatitis, which is not only applicable without irritation to affected areas of higher absorbability of drugs with high density of hair follicles such as the face and the neck, but also safe to apply to patients having sensitive skins, such as females and children, is much hoped for.

3. Natriuretic Peptides:

Natriuretic peptides (NPs) are classified into three known families, named atrial natriuretic peptide (ANP), brain natriuretic peptide (BNP), and C-type natriuretic peptide (CNP); their well-known members are composed of 28, 32, and 22 amino acid residues, respectively.

(1) ANP and BNP:

ANP and BNP are synthesized mainly by the atria and the ventricles, respectively, and released from the heart into the whole body. It is thought that nearly 100% of the circulating ANP and BNP in the blood originate from the heart. These ANP and BNP are reported to be deeply involved in numerous diseases, including hypertension, cardiomegaly, cardiac failure, myocardial infarction, valvular heart disease, cardiac dysrhythmia, and pulmonary hypertension.

Human ANP is a peptide produced and released by atrial cardiocytes, and is composed of 28 amino acids, of which the $7^{th}$ cysteine and the $23^{rd}$ cysteine are bonded by a disulfide bond to form a ring structure. ANP has been shown to have diuretic effects in the kidneys and relaxes/dilates vascular smooth muscle cells in the blood vessels. In contrast, human BNP is a peptide produced and released by ventricular cells, and is composed of 32 amino acids, of which the $10^{th}$ cysteine and the $26^{th}$ cysteine are bonded by a disulfide bond to form a ring structure. BNP also possesses both diuretic and vasodilatory effects. BNP was originally isolated and identified in the porcine brain in Japan in 1988, and is also called B-type natriuretic peptide.

Both ANP and BNP bind to the receptor NPR-A (also called GC-A) having a guanylate cyclase domain, and exert their effects stated above, by stimulating the production of cGMP. In fact, secretion of ANP is stimulated in response to an increase in the atrial pressure by its distension in congestive heart failure, etc., and through its action stated above, ANP relieves the symptoms of congestive heart failure, etc. Likewise, BNP's release is stimulated during certain conditions including myocardial infarction, and BNP, through its action mentioned above, relieves the symptoms associated with myocardial infarction, etc. (Refer to non-patent literature 1). Although most of the circulating BNP derives from the ventricles, some BNP is released by the atria. In cardiac failure, the level of expression of both ANP and BNP increases to as much as 100 times more the normal level, but the increase of BNP expression is reported to be both greater and faster than that of ANP. While ANP (hANP) is marketed as a prescription drug for treating acute cardiac failure in Japan, BNP is clinically used in the United States.

(2) CNP:

CNP, which was once thought to function only as a brain peptide because it was first found in the brain, has now been clarified to exist in the periphery as well. In the vessel walls, in particular, CNP specific receptors were found to be abundant in smooth muscle cells, and CNP is produced by cells of the monocyte/macrophage lineage and the endothelial cells.

For those reasons, CNP is speculated to function in the vascular walls as a local mediator involved in inhibition of growth of vascular smooth muscle cells. Its clinical application is currently being investigated for possible prevention of restenosis by CNP administration, which occurs with a certain frequency after percutaneous transluminal coronary angioplasty (PTCA) performed on patients with ischemic heart failure.

Recently it has been reported that intravenous administration of CNP remarkably improves cardiomegaly and fibrosis associated with myocardial infarction, and improves cardiac functions in animal experiments. Cardiac fibrosis is known to cause diastolic ventricular failure and cardiac dysrhythmia. Since CNP possesses a powerful action to suppress fibroblast proliferation, the potential of CNP as an anti-fibrotic medication for the heart is under investigation. Since CNP is a hormone naturally occurring in the body, there is only little concern of it having adverse side effects; accordingly clinical application of CNP as a therapeutic agent for arteriosclerotic diseases and heart diseases is expected. Here, examples of CNP include CNP-22 composed of 22 amino acids, and CNP-53 wherein 31 amino acid residues are attached to the N-terminal of CNP-22.

(3) Natriuretic Peptide Receptors:

Natriuretic peptide receptors are classified into three subtypes; NPR-A receptor (also called GC-A) and NPR-B receptor (also called GC-B) both of which contain a guanylate cyclase domain, and NPR-C receptor which lacks a guanylate cyclase domain. It is known that ANP can bind to NPR-A and NPR-C receptors, BNP can bind to NPR-A and NPR-C receptors, and CNP can bind to NPR-B and NPR-C receptors.

It is suggested that the activation of NPR-A receptors induces vasodilatory action, diuretic action, and cell growth inhibitory action, while NPR-B receptors are abundant in vascular smooth muscle cells and thought to be involved in the growth inhibition of vascular smooth muscle cells.

(4) Relationship Between Natriuretic Peptides and Immune System:

Historically, natriuretic peptide was first discovered as a peptide released from the atria, later named ANP, and its vasodilatory and diuretic actions gathered attention. BNP and CNP were then discovered as peptides similar to ANP. This historical background offers an explanation to why any attention to the relationship between natriuretic peptides and the immune system has been focused on those related to the cardiovascular system. CNP knock-out mice demonstrated impaired growth of cartilage resulting in a dwarfism-like phenotype (refer to Non-patent literature 2), which directed some interest to the relationship between arthritis and natriuretic peptides.

ANP is implicated in playing a role in arthritis and sepsis as it inhibits the release of inflammatory cytokines including tumor necrosis factor (TNF-α) and interleukin 1β (IL-1β) by macrophages (refer to Non-patent literature 3). This literature, however, does not mention ANP's relationship with the skin.

Similarly, the blood concentration of BNP has been reported to increase with the rejection response following heart transplant, and therefore it is suggested that it is associated with the immune regulation in the cardiovascular system (refer to Non-patent literature 4). However, this literature does not describe any connection between BNP and the skin.

Taking into account the observation that there is an increase in the blood concentration of BNP during the heart graft rejection, Kuroski de Bold et al. have investigated the immunoregulatory action of natriuretic peptides, and have demonstrated that both ANP and BNP inhibit the lymphocyte growth (refer to Non-patent literature 5). However, there is no connection between natriuretic peptides and the skin mentioned in this literature.

Chiurchiu et al. on the other hand have investigated the immunoregulatory action of BNP focusing on its association with the heart diseases and sepsis, and showed that BNP promotes the release by macrophages of pro-inflammatory cytokines such as arachidonic acid, prostaglandin E2 (PGE2), and leukotriene B4 (LTB4), and also promotes the release of anti-inflammatory cytokines including interleukin 10 (IL10). Thus, while BNP is indicated to have some action in the regulation of inflammatory responses, whether BNP acts overall to suppress or promote inflammatory responses remains inconclusive in the literature (refer to Non-patent literature 6). This literature also does not mention any connection between BNP and the skin.

Similarly, CNP is reported to be released by macrophages (refer to Non-patent literature 7), and while investigating the roles of CNP in cardiac ischemia and myocardial damage after reperfusion, Scotland et al. report that CNP suppresses platelet aggregation and lymphocyte migration (refer to Non-patent literature 8). The connection between CNP and the skin, however, is not described in this literature.

Likewise, Obata et al. examined the roles played by CNP in myocarditis using a rat myocarditis model generated by injecting pig myosin. They reported that continuous administration of CNP for 1 week had suppressed necrosis and inflammation of the cardiac tissues, while at the same time promoted the regeneration of blood vessels, thereby preventing functional loss of the heart (refer to Non-patent literature 9). Nevertheless, there is nothing in this literature to suggest a connection between CNP and the skin.

In addition, based on the observation that CNP knock-out mice show a dwarfism-like phenotype, attention has been paid to the potential connection between CNP and cartilage growth. Agoston et al. demonstrated that when incubated with Dexamethasone, the primary cultured chondrocytes extracted from the tibial bones of mouse embryos had significantly increased the expression of CNP genes (refer to Non-patent literature 10). This literature, however does not describe any connections between CNP and the skin.

It is evident that the connections between natriuretic peptides and the immune system have drawn increasing attention in recent years, but it is limited only to the inflammation of the cardiovascular system and arthritis, and the relationship between dermatitis or more specifically atopic dermatitis and natriuretic peptides has never been reported.

(5) Reports on the Application of Natriuretic Peptides:

Following are some examples of a number of applications of CNP, BNP and ANP.

Toshiko Koide and her colleagues have proposed a preparation for repair/regeneration of tissues and organs, comprising a composition that comprises ANP, BNP, CNP and urodilatin (P-Uro), and their precursors and derivatives, or combinations thereof as an active ingredient, and that may comprise pharmaceutically commonly-used diluents, excipients, fillers, and auxiliary agents (refer to Patent Literature 1).

However, specific examples of repair and regeneration of tissues and organs relate only to the regeneration of myocardiocytes, hypodermal tissue, hair, and improvement of cracked, rough skin due to wet work; they all correspond to ANP administration. There is no statement which implies therapeutic agents for treating skin disease or skin texture-improving agents by means of administration of CNP or BNP.

Masaharu Tanaka and his colleagues have proposed a C-type natriuretic peptide exhibiting a growth inhibitory action of vascular smooth muscle cells, as well as a growth inhibitory preparation for vascular smooth muscle cells containing such peptides as its active ingredient (refer to Patent Literature 2).

This, however, relates to the use of CNP in a growth inhibitory agent of vascular smooth muscle cells but does not imply application of CNP or BNP to therapeutic agents for dermatitis.

Katsuhiko Nakada and his colleagues proposed an eye drop for promoting lacrimal secretion or for treating keratoconjunctival disorder, containing as its active ingredient a natriuretic peptide, and they list ANP, BNP and CNP as examples of usable natriuretic peptide (refer to Patent Literature 3).

This, however, only relates to the application of the property of ANP, CNP and BNP to promote lacrimal secretion in an eye drop for treating keratoconjunctival disorder, and does not indicate the use of CNP or BNP in a therapeutic agent to treat dermatitis.

Kazuwa Nakao and his colleagues proposed a composition for increasing the body length containing a guanyl cyclase B (GC-B) activator as the active ingredient, which is to be administered to an individual without FGFR3 abnormality (refer to Patent Literature 4).

This indicates an application of CNP in a composition for increasing the body height based on the finding that the nose-anus length in transgenic mice which over-expressed CNP was larger than that in normal litters, but dose not imply the use of CNP or BNP in a therapeutic agent for dermatitis.

Kazuwa Nakao and his colleagues also proposed a prophylactic agent or therapeutic agent for inflammation of the joints containing a guanyl cyclase B (GC-B) activator such as CNP as an active ingredient (refer to Patent Literature 5).

However, this relates only to the application of CNP in a therapeutic agent or prophylactic agent for inflammation of the joints based on a study revealing that, compared to their litter mates, the articular cartilages grow thicker in the transgenic mice which over-express CNP, along with the observation that arthritis is repressed by the continuous administration of CNP to model animals of arthritis. Hence this does not imply the application of CNP or BNP in a therapeutic agent for dermatitis.

In addition, Masaharu Tanaka and his colleagues reported that CNP differs from ANP and BNP in the structure and function effects as stated below (refer to Patent Literature 2).

"At present, both ANP and BNP are thought to act as a hormone secreted by the heart into the blood, as well as a neurotransmission factor, and to play an important role in maintaining the amount of body fluid and homeostasis of blood pressure . . . . There are many unknown points in the physiological roles of CNP as a natriuretic peptide. Namely, since CNP has an amino acid primary sequence similar to that of ANP and BNP and shows a natriuretic action and a hypotensive action by in vivo administration, CNP was relegated to the natriuretic peptide family. However, because the natriuretic action and hypotensive action of CNP are significantly weaker than those of ANP and BNP (from 1/50 to 1/100) . . . , CNP has held a unique position in the natriuretic peptide family, and has been presumed to be playing a role different from the maintenance of amounts of body fluid and homeostasis of blood pressure . . . . Comparing the structure of CNP with that of ANP/BNP, CNP differs from ANP or BNP in the following points. Namely, the primary amino acid sequence of CNP differs from that of ANP or BNP at the exocyclic N-terminal domain; of the 17 amino acid residues in the endocyclic domain, 5 residues and 4 residues in CNP differ from those in ANP and BNP, respectively. In addition, the structure of the exocyclic C-terminal domain of CNP largely differs from that of ANP or BNP, and CNP does not have the tail structure which exists in ANP or BNP (in the cases of ANP and BNP, 5 amino acid residues and 6 amino acid resides, respectively, are attached to the C-terminal of the cyclic structure in ANP and BNP; this structure is called a tail structure for descriptive purposes). Thus-described structural differences between CNP and ANP/BNP are obviously involved in the manifestation of the above-mentioned characteristic pharmacological effects of CNP."

REFERENCE LIST

Patent Literature

Patent Literature 1: JP A 2008-162987
Patent Literature 2: JP A 6-9688
Patent Literature 3: JP A 2000-169387
Patent Literature 4: WO 2005/094890
Patent Literature 5: WO 2005/094889

Non-Patent Literature

Non-patent Literature 1: European J. Endocrinology, Vol. 135, p. 265, 1996.
Non-patent Literature 2: Proceedings of the National Academy of Sciences of the United States of America, Vol. 98, No. 7, p. 4016, 2001.
Non-patent Literature 3: Annals of the Rheumatic Disease, Vol. 60, Suppl 3, iii, p. 68, 2001.
Non-patent Literature 4: The Journal of Heart and Lung Transplantation, Vol. 27, p. 31, 2008.
Non-patent Literature 5: The Journal of Heart and Lung Transplantation, Vol. 29, No. 3, p. 323, 2010.
Non-patent Literature 6: Regulatory Peptides, Vol. 148, p 26, 2008.
Non-patent Literature 7: Experimental Hematology, Vol. 29, p. 609, 2001.
Non-patent Literature 8: Proceedings of the National Academy of Sciences, Vol. 102, No. 40, p. 14452, 2005.
Non-patent Literature 9: Biochemical and Biophysical Research Communications, Vol. 356, p. 60, 2007.
Non-patent Literature 10: BMC Musculoskeletal Disorders, Vol. 7, p. 87, 2006.

DISCLOSURE OF INVENTION

Summary of Invention

Problems to be Solved by the Invention

The chronic nature of dermatitis, a representative skin disease, and in particular atopic dermatitis, makes continuous use of drugs necessary. While steroid external preparations produce satisfactory clinical effects as stated above, they also have many adverse local effects, including skin thinning and atrophy, moon face, skin flush, hirsutism, and skin striae, hence their application to areas of high drug absorbability such as the face, and to patients with sensitive skin, children and females, has been difficult. In addition to the problem of adverse local effects, the repeated and long-term use of topical steroids, which is necessary in many cases due to the chronic nature of atopic dermatitis, can lead to rebound phenomena induced by discontinuation of external application. In other words, an acute exacerbation, which is worse than the state before the application, occurs upon abrupt discontinuation of external application. In addition, as more serious complications, erythroderma posteczematosa with whole-body skin flush and desquamation can result from continuous inappropriate external application. These severe symptoms induced by a long-term use of steroids have been a serious problem.

Hence, the aim of the present invention is to provide an effective and safe skin external preparation composition for patients with dermatitis, atopic dermatitis in particular, which is not only effective against severe conditions which are intractable with the currently available external preparations, but also safely applicable to affected areas of the face and neck, and also safely applicable to patients with sensitive skin, children and females. Furthermore, the invention also aims to provide a skin texture-improving agent to enhance the skin barrier functions important for prevention of recurrence, to improve the texture and moisture retention ability of the skin, which has an anti-inflammatory effect and effects of care for the horny cell layer, care for the epidermis, and care for the basal membrane.

Means for Solving Problems

Through extensive research, the inventors of the present invention discovered that C-type natriuretic peptide (CNP) and B-type natriuretic peptide (BNP) are safe and effective as a therapeutic agent for dermatitis, especially atopic dermatitis, and that they are also applicable to the face and neck, and patients who have sensitive skins, children and females. The present invention was thus made.

The present invention comprises the following.
1. A skin external-preparation composition comprising C-type natriuretic peptide (CNP) or B-type natriuretic peptide (BNP).
2. The skin external-preparation composition according to the item 1, wherein the C-type natriuretic peptide (CNP) or B-type natriuretic peptide (BNP) is a chimeric peptide of CNP and BNP, in which CNP is CNP-22, CNP-53, or a peptide comprising any amino acid sequence with 5 or more consecutive amino acids in the amino acid sequence having deletion, substitution, or addition of any amino acid in the amino acid sequence of CNP-22 or CNP-53, and in which BNP is BNP-26, BNP-32, BNP-45, or a peptide comprising any amino acid sequence with 5 or more consecutive amino acids in the amino acid sequence having deletion, substitution, or addition of any amino acid in the amino acid sequence of BNP-26, BNP-32 or BNP-45, and wherein the chimeric peptide forms a ring structure by an intramolecular disulfide bond, and wherein the chimeric peptide has CNP activity or BNP activity; or derivative(s) of the chimeric peptide.
3. The skin external-preparation composition according to the item 1, wherein the C-type natriuretic peptide (CNP) is CNP-22, CNP-53, or a CNP derivative in which any amino acid in the amino acid sequence of CNP-22 or CNP-53 is deleted, substituted or added, and which has CNP activity.
4. The skin external-preparation composition according to the item 3, wherein the C-type natriuretic peptide (CNP) is CNP-22.
5. The skin external-preparation composition according to the item 1, wherein the B-type natriuretic peptide (BNP) is BNP-26, BNP-32, BNP-45, or a BNP derivative in which any amino acid in the amino acid sequence of BNP-26, BNP-32, or BNP-45 is deleted, substituted or added, and which has BNP activity.
6. The skin external-preparation composition according to the item 5, wherein the B-type natriuretic peptide (BNP) is BNP-32.

7. The skin external-preparation composition according to the item 1, comprising 1-500 μg/g of C-type natriuretic peptide (CNP) or B-type natriuretic peptide (BNP).
8. The skin external-preparation composition according to the item 1, comprising 20-200 μg/g of C-type natriuretic peptide (CNP) or B-type natriuretic peptide (BNP).
9. The skin external-preparation composition according to the item 1, comprising 30-100 μg/g of C-type natriuretic peptide (CNP) or B-type natriuretic peptide (BNP).
10. The skin external-preparation composition according to the item 1, wherein the skin external-preparation composition is a therapeutic agent for dermatitis or a skin texture-improving agent.
11. The skin external-preparation composition according to the item 10, wherein the skin external-preparation composition is a therapeutic agent for dermatitis, and the dermatitis is atopic dermatitis, dermatitis that led up to steroid dermatitis, steroid-resistant dermatitis, dermatitis to which tacrolimus is not applicable, chronic dermatitis, erythroderma, eczema, contact dermatitis, seborrheic dermatitis, autosensitization dermatitis, stasis dermatitis, urticaria, drug eruption, dermal vasculitis, prurigo, pruritus cutaneus, erythema, psoriasis, rosacea, rosacea-like dermatitis, lichen planus, or follicular keratosis.
12. The skin external-preparation composition according to the item 11, wherein the dermatitis is atopic dermatitis
13. The skin external-preparation composition according to the item 11, wherein the dermatitis is dermatitis that led up to steroid dermatitis.
14. The skin external-preparation composition according to the item 11, wherein the dermatitis is steroid-resistant dermatitis.
15. The skin external-preparation composition according to the item 11, wherein the dermatitis is the one for which tacrolimus is not applicable.
16. The skin external-preparation composition according to the item 11, wherein the dermatitis is chronic dermatitis.
17. The skin external-preparation composition according to the item 11, wherein the dermatitis is eczema.
18. The skin external-preparation composition according to the item 11, wherein the dermatitis is erythroderma.
19. The skin external-preparation composition according to the item 11, wherein the dermatitis is rosacea.
20. The skin external-preparation composition according to the item 11, wherein the dermatitis is rosacea-like dermatitis.
21. The skin external-preparation composition according to the item 11, wherein the dermatitis is psoriasis.
22. The skin external-preparation composition according to the item 10, wherein the skin external-preparation composition is a therapeutic agent for dermatitis, and the dermatitis is an inflammation associated with at least one rash symptom selected from erythema, infiltrative erythema, lichenified lesion, scales, adhesion of crusts, eczema, abrasion, excoriation, prurigo nodularis, papule, erosion, infiltration, vesicle, and edema.
23. The skin external-preparation composition according to the item 10, wherein the skin external-preparation composition is a therapeutic agent for dermatitis, and the dermatitis shows an immune reaction to at least one allergen selected from house dust, mite, cedar pollen, orchard grass pollen, ragweed pollen, egg white, and egg yolk.
24. The skin external-preparation composition according to the item 10, wherein the skin external-preparation composition is a therapeutic agent for dermatitis, and the dermatitis occurs in at least one region selected from the face, neck, back, and arms.
25. The skin external-preparation composition according to the item 1, wherein the dosage form of the external preparation is selected from ointment, gel, cream, lotion, solution, spray, and patch.
26. The skin external-preparation composition according to the item 25, wherein the dosage form is ointment, gel, cream, or solution.
27. The skin external-preparation composition according to the item 1, wherein the skin external-preparation composition is a skin texture-improving agent.
28. The skin external-preparation composition according to the item 27, wherein the skin external-preparation composition is a skin texture-improving agent for improving dry skin, rough skin, sensitive skin and fine wrinkles.
29. The skin external-preparation composition according to the item 27, wherein the skin texture-improving agent is a skin care product or a quasi drug.
30. The skin external-preparation composition according to the item 27, wherein the dosage form is cream, foam, skin lotion, facial mask, skin-softening water, skin emulsion, foundation, makeup base, essence, soap, liquid cleanser, bath agent, sun-block cream, suntan oil or spray-type liquid preparation.

Effects of the Invention

As described in the examples given below, a skin external-preparation composition of the present invention comprising CNP or BNP as its active ingredient can greatly improve erythema, papules and scales associated with severe swelling/edema/infiltration or lichenification, thereby achieving either remission, mild conditions mainly characterized by dry skin with mild erythema and scales, or minor rash having little inflammatory symptoms with dryness of the skin as its main symptom. Hence, the therapeutic agent for dermatitis of the present invention is expected to be applicable and extremely effective against atopic dermatitis, which develops resistance to the conventional steroid external drugs. In particular, it is possible to dramatically improve erythema, infiltration, scales or lichenification and burning sensation on the adult face without producing irritative symptom, which interfere with many aspects of social life. Remarkable improvements are also made in the other parts of the body including the upper limbs and back. The effects are not limited to adults but are similar with infants.

Conventionally and widely used steroid external preparations have the drawbacks of, upon discontinuation of the external application, relapsing to the severity of pre-treatment conditions, or worse, the rebound phenomena mainly characterized by the recurrence of worsened condition. In contrast, the present invention not only completely lacks these problems, but also results in moisturized, fine-textured skin. The effects of the therapeutic agent for dermatitis of the present invention lasted 5 days to 2 weeks after its application was terminated, and the improved skin conditions were sustained throughout. Even in cases, which did not result in the prominent effect, the therapeutic goals of atopic dermatitis were achieved, namely, the main symptoms were improved to dryness, minor or mild severity of erythema, and scales, etc. Furthermore, minor erythema, edema, papules and scales, which recurred after the treatment in some cases, did not worsen to the pre-treatment conditions and remained stable. This could not be attained by the steroid external preparations, the former therapeutic option, and is therefore worthy of special mention. In addition, when re-applied to the rashes that had relapsed, CNP or BNP preparations of the present invention required a smaller number of applications than that of the initial time to reduce the severity of symptoms to either mild or minor rash. In terms of manifestation of effects, the patients experienced subjective awareness of burning sensation subsiding approximately 10 min after the application, and this was followed by the improvements of observable symptoms including erythema, infiltration, edema, papules, scales and excoriations after approximately 30 min. When application was further continued from 2 days to 4 days, erythema and infiltration improved remarkably and the skin became near-normal in condition with a fine texture in many cases. These findings were astonishing even for the inventor of the present invention who is a dermatologist. CNP preparations demonstrated especially remarkable effects.

Given that both BNP and ANP belong to the same family and share the same receptors, it was formerly assumed that BNP and ANP preparations possessed equivalent effects. When they were actually tested on patients with inflammatory disease, in particular atopic dermatitis, however, BNP preparations were revealed to have much more intense pharmacological effects than ANP preparations. That is to say that BNP preparations are faster-acting than ANP preparations, and lead to better improvements of the clinical symptoms and the effects lasted longer. On the other hand, ANP preparations unexpectedly resulted in much poorer improvements in the local dermal symptoms of erythema, infiltration, scale and lichenification compared to BNP preparations, and in many cases, the symptoms showed no improvements or worsened. In cases where a little improvement was observed with ANP preparations, manifestation of the effects was slow and even 7 consecutive days of external application did not result in complete remission of erythema, while both erythema and dryness of the skin remained in all cases. The finding that BNP as a skin external-preparation composition had more intense pharmacological effects than ANP belonging to the same family of natriuretic peptide was surprising.

The active ingredients of the present invention, CNP and BNP, are hormones which naturally occur in the body. Side effects are less expected and with adequate dosage, they are thought to have only a minor effect on the hemodynamic status and hence they are safe to apply to patients with low or unstable blood pressure, allowing long-term administration to chronic dermatitis patients. They show a potency to dermatitis greater than that of conventional steroid external preparations and are also rapid-acting to a greater degree and lead to longer-lasting effects, or more precisely, 5 days to 2 week remission periods were observed even in the severe cases. Moreover, the skin external-preparation composition of the present invention is safely applicable to patients with sensitive skin, children and females, and to the face and neck region, etc. without irritation symptoms, and this makes the present invention an unprecedented, important therapeutic agent for dermatitis.

In addition, when a skin texture-improving agent comprising CNP or BNP of the present invention was applied, effects such as improvement of the texture, dryness and roughness of the skin while enhancing the softness and moisture retention, as well as obscuring fine wrinkles were confirmed. The present invention can therefore be intended as both a therapeutic agent for dermatitis and a skin texture-improving agent aimed at skincare products or similar for improving elasticity, wrinkles of the skin and moisture retention.

EMBODIMENTS FOR CARRYING OUT THE INVENTION

Figure 1:
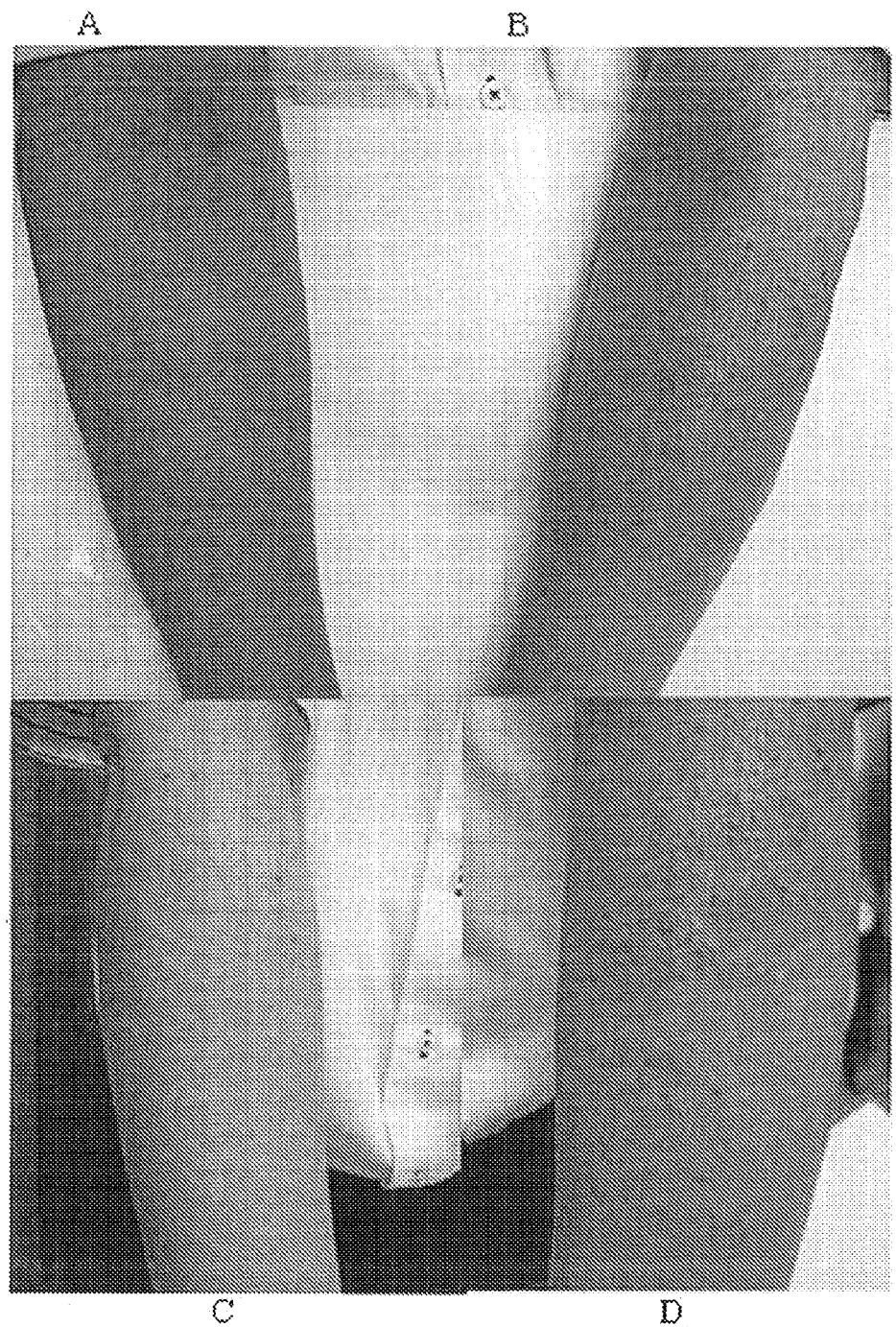
FIG. 1 is a photograph showing the effects of a CNP gel preparation of the present invention when it was applied to a patient who had severe swelling, infiltration and erythema on the upper limbs. A and B show the state before application. C shows the state after application of the CNP gel preparation with 30 µg/g concentration three times at 20 min intervals, while D shows the state after application of a gel preparation without the addition of CNP 3 times at 20 min intervals. (Refer to Case 10 of the CNP gel preparation; subject 5: Tables 3 and 4)

The active ingredient of the skin external-preparation compositions of the present invention is C-type natriuretic peptide (CNP) or B-type natriuretic peptide (BNP).

Here, the CNP means: CNP-22 composed of 22 amino acids, and CNP-53 composed of 53 amino acids in which 31 amino acid residues are attached to the N-terminal of the CNP-22, or derivatives thereof without any particular limitations provided that they possess CNP activity. These CNP-22, CNP-53, and their derivatives are all heretofore known, and can be manufactured by chemical synthesis or genetic manipulations.

There are no particular limitations to the origin of CNP-22 and CNP-53, provided that they possess CNP activity, but the CNP derived from mammals including humans or birds is preferred, and more preferably, the CNP derived from humans, monkeys, mice, rats or pigs, and particularly preferably, the CNP derived from humans.

The CNP derivatives means those having, in the amino acid sequences of the CNP-22 or CNP-53, deletion(s), substitution(s) or addition(s) of 1-5 amino acids, more preferably 1-3 amino acids, and furthermore preferably 1 or amino acids, while possessing CNP activity, or alternatively, those having a sequence with a homology of 85% or more, preferably 90% or more, and more preferably 95% or more with the amino acid sequence of the CNP-22 or CNP-53, while possessing CNP activity.

Replaceable amino acids are ideally substituted by conservative amino acid substitution with amino acids having similar polarities and charges. For example, nonpolar uncharged amino acids include glycine, alanine, valine, leucine, isoleucine, proline, etc.; aromatic amino acids include phenylalanine, tyrosine, tryptophan; polar uncharged amino acids include serine, threonine, cysteine, methionine, asparagine, glutamine, etc.; negatively-charged amino acids include asparaginic acid, glutamic acid; positively-charged amino acids include lysine, arginine, histidine. Thus, preferably amino-acid substitution is carried out between conservative amino acids belonging to the same group. Here, when proline is to be replaced by another nonpolar uncharged amino acid, or when proline is to replace another nonpolar uncharged amino acid, then it should be noted that proline is not flexible in its spatial orientation. Similarly, when cysteine is to be replaced by another polar uncharged amino acid, or when cysteine is to replace another polar uncharged amino acid, then it should be noted that cysteine may form a disulfide bond with another cysteine.

CNP derivatives may include those amidated or methoxylated at a C-terminal, CNP modified with addition of polyethylene glycol or fatty acids, and, glycosylated or alkylated CNP, given that they have CNP activity.

Thus, any heretofore known CNPs with CNP activity can be used in the present invention. Examples may include CNP derivatives disclosed in JP A 6-9688, CNP derivatives disclosed in U.S. Pat. No. 5,583,108, and CD-NP disclosed in U.S. Pat. No. 6,818,619. It is possible to easily test the presence/absence of CNP activities using heretofore known procedures, such as by testing a growth inhibitory action on the vascular smooth muscle cells, or by examining the activity of cGMP production in the cells expressing NPR-B receptors.

While any of CNP-22, CNP-53 and their derivatives can be used as the active ingredient of the present invention, CNP-22 with a smaller molecular weight is more preferable in terms of absorbability. CNP-22 can be manufactured by chemical synthesis or genetic manipulations using human CNP genes, and is also available from, for example, Peptide Institute Inc. as CNP-22 (human).

CNP that can be used in the present invention includes: purified naturally occurring CNP, genetically engineered CNP manufactured using known genetic engineering procedures, CNP manufactured using known chemical synthetic procedures (such as solid-phase peptide synthesis by a peptide synthesis machine). Basic methods including genetic engineering techniques, site-specific mutagenesis, and PCR, are commonly known or heretofore known, and are described in, for example, Current Protocols In Molecular Biology; John Wiley & Sons (1998), and JP A 5-207891.

Here, the BNP refers to: BNP-26 composed of 26 amino acids, BNP-32 composed of 32 amino acids, BNP-45 composed of 45 amino acids, or their derivatives without any particular limitations provided that they possess BNP activity. BNP can also be high molecular weight γ-BNP (molecular weight of approximately 13,000) which is formed by the removal of the signal peptide from a BNP precursor. BNP-32 and their derivatives are preferred. BNP-26, BNP-32, BNP-45, and their derivatives are heretofore known, and can be manufactured by chemical synthesis or genetic manipulations.

There are no particular limitations to the origin of the BNP-26, BNP-32 and BNP-45, provided that they possess BNP activity, but the CNP derived from mammals including humans or birds is preferred, and the CNP derived from humans, monkeys, mice, rats or pigs is more preferred, and the CNP derived from humans is particularly preferred.

The BNP derivatives means, those having, in the amino acid sequences of BNP-26, BNP-32 or BNP-45, deletion(s), substitution(s) or addition(s) of 1-5 amino acids, more preferably 1-3 amino acids, and furthermore preferably 1 or amino acids, while possessing BNP activity, or alternatively, those having a sequence with a homology of 85% or more, preferably 90% or more, and more preferably 95% or more with the amino acid sequence of BNP-26, BNP-32 or BNP-45, while possessing BNP activity.

Replaceable amino acids are ideally substituted by conservative amino acid substitution with amino acids having similar polarities and charges. For example, nonpolar uncharged amino acids include glycine, alanine, valine, leucine, isoleucine, proline, etc.; aromatic amino acids include phenylalanine, tyrosine, tryptophan; polar uncharged amino acids include serine, threonine, cysteine, methionine, asparagine, glutamine, etc.; negatively-charged amino acids include asparaginic acid, glutamic acid; positively-charged amino acids include lysine, arginine, histidine. Thus, preferably amino-acid substitution is carried out between conservative amino acids belonging to the same group. Here, when proline is to be replaced by another nonpolar uncharged amino acid, or when proline is to replace another nonpolar uncharged amino acid, then it should be noted that proline is not flexible in its spatial orientation. Similarly, when cysteine is to be replaced by another polar uncharged amino acid, or when cysteine is to replace another polar uncharged amino acid, then it should be noted that cysteine may form a disulfide bond with another cysteine.

BNP derivatives may include those amidated or methoxylated at a C-terminal of BNP, BNP modified with addition of polyethylene glycol or fatty acids, and, glycosylated or alkylated BNP, provided that they have BNP activity.

Thus, any heretofore known BNP with BNP activity can be used in the present invention. Examples may include BNP derivatives disclosed in JP A 2007-525213, BNP derivatives disclosed in U.S. Pat. No. 6,028,055, BNP derivatives disclosed in U.S. Pat. No. 5,114,923, and BD-NP disclosed in U.S. Pat. No. 6,818,619.

It is possible to easily test the presence/absence of BNP activity using heretofore known procedures, such as an examination of the activity of cGMP production in the cells expressing NPR-A receptors.

While any of BNP-26, BNP-32, BNP-45 and their derivatives can be used as the active ingredient of the present invention, BNP-32 is preferable in terms of drug efficacy and availability.

BNP of the present invention can be manufactured by chemical synthesis or genetic manipulations using human BNP genes (for example, refer to JP A 5-207891, JP A 2007-525957, JP A 2007-525213), and BNP is also commercially available since it has already been launched. Alternatively, it is available from, for example, Peptide Institute Inc. as BNP-32 (human).

BNP that can be used in the present invention includes: purified naturally occurring BNP, genetically engineered BNP manufactured using known genetic engineering procedures, BNP manufactured using known chemical synthesis procedures (such as solid-phase peptide synthesis by a peptide synthesis machine). Basic methods including genetic engineering techniques, site-specific mutagenesis, and PCR, are commonly known or heretofore known, and are described in, for example, Current Protocols in Molecular Biology; John Wiley & Sons (1998), and JP A 5-207891.

When the term "CNP or BNP" is used herein, it refers to either CNP or BNP, as well as the chimeric peptides of CNP and BNP. That is, as used herein, the term "CNP or BNP" refers to "CNP or BNP" which may be: a chimeric peptide of CNP and BNP, in which CNP is CNP-22, CNP-53, or a peptide comprising any amino acid sequence with 5 or more consecutive amino acids in the amino acid sequence having deletion, substitution, or addition of any amino acid in the amino acid sequence of CNP-22 or CNP-53, and in which BNP is BNP-26, BNP-32, BNP-45, or a peptide comprising any amino acid sequence with 5 or more consecutive amino acids in the amino acid sequence having deletion, substitution, or addition of any amino acid in the amino acid sequence of BNP-26, BNP-32 or BNP-45, and wherein the chimeric peptide is the one that for a ring structure by an intramolecular disulfide bond, and wherein the chimeric peptide is the one that has CNP activity or BNP activity; or a derivative of the chimeric peptide.

Here, there are no particular limitations to the origin of CNP-22 and CNP-53, provided that they possess CNP activity, but the CNP derived from mammals including humans or birds are preferred, and more preferably, CNP derived from humans, monkeys, mice, rats or pigs, and most preferably, CNP derived from humans. Similarly, there are no particular limitations to the origin of BNP-26, BNP-32 and BNP-45, provided that they possess BNP activity, but the BNP derived from mammals including humans or birds is preferred, and the BNP derived humans, monkeys, mice, rats or pigs is more preferred, and the BNP derived from humans is particularly preferred.

The derivatives of chimeric peptide of CNP and BNP mean those which have, in the amino acid sequences of the chimeric peptide of CNP and BNP, a deletion, addition or substitution of preferably 1-5 amino acids, more preferably 1-3 amino acids, and furthermore preferably 1 or 2 amino acids, while possessing CNP or BNP activity.

Replaceable amino acids are ideally substituted by conservative amino acid substitution with amino acids having similar polarities and charges. For example, nonpolar uncharged amino acids include glycine, alanine, valine, leucine, isoleucine, proline, etc.; aromatic amino acids include phenylalanine, tyrosine, tryptophan; polar uncharged amino acids include serine, threonine, cysteine, methionine, asparagine, glutamine, etc.; negatively-charged amino acids include asparaginic acid, glutamic acid; positively-charged amino acids include lysine, arginine, histidine. Thus, preferably amino-acid substitution is carried out between conservative amino acids belonging to the same group. Here, when proline is to be replaced by another nonpolar uncharged amino acid, or when proline is to replace another nonpolar uncharged amino acid, then it should be noted that proline is not flexible in its spatial orientation. Similarly, when cysteine is to be replaced by another polar uncharged amino acid, or when cysteine is to replace another polar uncharged amino acid, then it should be noted that cysteine may form a disulfide bond with another cysteine.

The derivatives of chimeric peptide of CNP and BNP may include those amidated or methoxylated at C terminal of the of chimeric peptide of CNP and BNP, those modified with addition of polyethylene glycol or fatty acids in the chimeric peptide of CNP and BNP, and, glycosylated or alkylated chimeric peptide of CNP and BNP, provided that they have CNP or BNP activity.

Thus, it is possible to use any heretofore known chimeric peptides of CNP and BNP or derivatives thereof in the present invention, on the condition that they possess CNP or BNP activity.

Presence/absence of CNP or BNP activity can be easily tested using heretofore known procedures, such as an examination of the activity of cGMP production in the cells expressing NPR-A receptors or in the cells expressing NPR-B.

The chimeric peptides of CNP and BNP and their derivatives of the present invention can also be manufactured by chemical synthesis or by genetic manipulations.

Dermatitis is an inflammation of the skin, characterized by common symptoms such as erythema, infiltrative erythema, lichenified lesions, scales, adhesion of crusts, eczema, abrasion, excoriations, prurigo nodularis, papules, erosions, infiltration, vesicles, edema, etc., and in particular, symptoms such as itching, blisters, reddening, swelling, feeling of oozing, scabs, scale formation, etc.

The skin external-preparation composition of the present invention can be applied to dermatitis patients with inflammation, preferably suffering from, but not limited to; atopic dermatitis, dermatitis that led up to steroid dermatitis, steroid-resistant dermatitis, dermatitis which cannot be treated with tacrolimus, chronic dermatitis, erythroderma, eczema, contact dermatitis, seborrheic dermatitis, autosensitization dermatitis, stasis dermatitis, urticaria, drug eruption, cutaneous angiitis, prurigo, pruritus cutaneus, erythema, psoriasis, rosacea, rosacea-like dermatitis, lichen planus, follicular keratosis, and more preferably from atopic dermatitis, dermatitis that led up to steroid dermatitis, steroid-resistant dermatitis, dermatitis which cannot be treated with tacrolimus, chronic dermatitis, eczema, erythroderma, rosacea, rosacea-like dermatitis, and psoriasis, and even more preferably from atopic dermatitis, steroid-resistant dermatitis, chronic dermatitis, eczema, erythroderma, rosacea, rosacea-like dermatitis, and psoriasis, and most preferably from atopic dermatitis.

A skin external-preparation composition means a composition externally and directly applicable to the skin, and more specifically refers to a therapeutic agent for dermatitis or skin texture-improving agent. There are no particular limitations in its dosage form, but preferably it is an ointment, gel, cream, lotion, solution, spray, or patch, and more preferably, an ointment, gel, cream or solution. These dosage forms are particularly suited for therapeutic agents for dermatitis. When the skin external-preparation composition of the present invention is to be used as a skin texture-improving agent, the preferred dosage forms are the following; cream, foam, skin lotion, facial mask, skin-softening water, skin emulsion, foundation, makeup base, essence, soap, liquid cleanser, bath agent, sun-block cream, suntan oil or spray-type liquid preparation. When the skin external-preparation composition of the present invention is used as a skin texture-improving agent, it may be a skin-care cosmetic or a quasi drug.

In terms of indication, the skin external-preparation composition of the present invention as a therapeutic agent for dermatitis can be applied to dermatitis associated with at least one of the rash symptoms selected from: erythema, infiltrative erythema, lichenified lesions, scales, adhesion of crusts, eczema, abrasion, excoriations, prurigo nodularis, papules, erosions, infiltration, vesicles, and edema. These symptoms are the symptoms observed in patients with atopic dermatitis.

Atopic dermatitis mentioned above is defined by the Japanese Dermatological Association as a dermatitis for "which exacerbations and remissions recur, being mainly characterized by pruritic eczema, in which most of the patients have atopic diathesis".

That is to say, atopic dermatitis is a chronic eczema associated with itching that occurs in those who have an allergic predisposition. It is a typical inflammatory skin disease showing the conditions wherein the symptoms accompany itching, the rashes are eczematous lesions, which reddens as an acute lesion (erythema), oozing eruptions (papules and serous papules) are formed, then the skin peeled off and crusts are formed (scales and crusts). The chronic pathological lesions include thickening and hardening of the skin (lichenification), and formation of hard lumps (prurigo). Rashes have a tendency to develop on the forehead, around the eyes, around the mouth, on the neck, around the joints such as the elbows, knees and wrists, on the dorsal and abdominal regions, and they are often characterized by a symmetrical distribution. In infantile atopic dermatitis, the lesions generally appear on the head and face first, and occasionally spread to the trunk and four limbs, whereas in puberty and adulthood, severe rashes tend to occur in the upper body (face, neck, chest and back). Atopic dermatitis also has a tendency to be chronic or recurrent lasting over 6 months, or 2 months in infants.

The skin external-preparation of the present invention, in particular the therapeutic agent for dermatitis, is both safe and effective as a therapeutic agent for such atopic dermatitis which has conventionally been regarded as a difficult-to-treat disease.

Dermatitis that led up to steroid dermatitis refers to dermatitis, wherein it develops a group of adverse side effects due to the long-term continuous use of steroid external drugs. In particular, dermatitis in which a rebound phenomenon occurs upon withdrawal from steroid external drugs is called steroid dermatitis, and steroid rosacea is a typical example of steroid dermatitis.

Steroid-resistant dermatitis refers to dermatitis with decreased responsiveness to the steroid external preparations resulting from long-term use of the steroid external preparations. Steroid-resistant dermatitis tends to occur when steroid external preparations are used for a long time for the treatment of atopic dermatitis.

Dermatitis to which tacrolimus is not applicable, means dermatitis suffered by pregnant women, infants below the age of 2, patients with oozing ulcerated regions or scratches, and women who are breast-feeding. In cases of dermatitis in immune-compromised patients and patients with a kidney disorder, caution needs to be taken with the use of tacrolimus. Hence, these dermatitides can also be regarded as the dermatitis to which tacrolimus is not applicable.

Chronic dermatitis is a dermatitis that has become chronic and intractable, and includes atopic dermatitis and contact dermatitis caused by an allergy or an irritation by the substance that contacts the skin.

Psoriasis is a chronic and repeatedly recurrent skin disease, characterized by one or several erythematous rashes (erythema) and silvery-white squamate scales.

Erythroderma, also called exfoliative dermatitis, commonly develops from atopic dermatitis or eczema in elderly patients, and it is a dermatitis characterized by skin flush over the whole body accompanied by desquamation. Diffuse erythema is observed over the whole body or on wide areas of the skin. Erythroderma includes erythroderma posteczematosa and erythroderma secondary to dermatoses, toxic erythroderma, infantile desquamative erythroderma, and paraneoplastic erythroderma. Of these, erythroderma posteczematosa refers to a state called erythroderma that shows skin flush and desquamation over the whole body, caused by generalization of eczema due to long-term external application of inappropriate steroids or due to an increase of severity. Erythroderma is a significantly intractable disease with systemic symptoms, which is usually associated with itching, and as systemic symptoms, associated with failure of thermoregulation such as fever, chills, and shivering, hypoproteinemia and edema occurring with desquamation, electrolyte abnormality due to loss of water from the exfoliated skin, swelling of lymph nodes, a general feeling of malaise, and loss of body weight. Internal or external application of steroids is adopted for the treatment; however, because of its significantly intractable nature, symptoms may immediately relapse or even worsen as rebound phenomena upon discontinuation of medication.

Rosacea is a persistent skin disease, which typically produces conditions in which reddening and small pustules occur on the central area of the face, and in which blood vessels are fairly visible.

Rosacea-like dermatitis is characterized by many red papules, diffused skin flush and desquamation, and is often seen in adult females. Its major development factor is a long-term external application of steroids, and it is one of the representative side effects of steroid external preparations; for its treatment, rebound of symptoms is severe, and therapeutic technique and the patients' patience are required for getting over it.

Prurigo often induces rashes as symptoms in addition to itching. Major causes of prurigo include parasites such as *Sarcoptes scabiei*, mites and lice, insect bites, urticaria, atopic dermatitis, allergic dermatitis and contact dermatitis, etc.

Erythema multiforme is a repeatedly recurrent dermatosis characterized by red raised skin lesions, presenting rashes that look like shooting targets. Symptoms of erythema multiforme often appear as a result of infection with herpes simplex viruses. In many cases, Erythema multiforme develops suddenly, and presents with red rashes (erythema) on the arms, legs and face as symptoms. Erythema presents with symptoms in a concentric fashion like a shooting target, sometimes associated with blisters.

Erythema nodosum is an inflammatory disease with tender red lumps (nodules) under the skin. Quite frequently it appears as a symptom of other diseases or as hypersensitivity to drugs. Young adults, in particular females are prone to erythema nodosum. It relapses repeatedly for several months to several years. Erythema nodosum may occur from infection with bacteria, fungi, or viruses.

Lichen planus is a skin disease with recurrent itching. Its symptoms include occurrence of small red or purple raised rashes. Initially the rashes are individually separated, then in many cases, plural rashes are fused to form papules associated with rough, scaly and dry skin.

Lichen pilaris is also called as follicular keratosis. It is a disease in which the orifice of the hair follicle is clogged with dead cells (cuticle) that have been sloughed off from the upper layer of the skin.

Contact dermatitis includes irritant contact dermatitis and allergic contact dermatitis. The former is an inflammation of the skin caused by direct contact of the skin with a specific irritant, such as acid, alkali and solvent, etc. The rash is associated with strong itching, and affected regions are limited, often having a clear boundary with normal skin.

The therapeutic agent compositions for dermatitis of the present invention can be formulated using widely used technologies. Examples of their formulation include external preparation, injectable preparation, oral preparation, and nasal preparation. In the case of oral preparation, enteric-coated preparations are preferred in order to avoid peptide degradation in the stomach. Examples of enteric-coated preparations include preparations wherein an enteric-substance is coated on capsules, tablets, or granules. In general, since peptide drugs are rapidly metabolized and easily excreted from the body, they can be modified with polyethylene glycol (PEGylation) in order to prolong their half life without affecting the biological activities, and to decrease antigenicity.

The preferred dosage form of the therapeutic agent compositions for dermatitis of the present invention is external preparations (transdermal absorption preparations) such as gel preparations, ointment preparations, liquid preparations, etc.

External preparations are not particularly limited as long as the present agent can be directly applied, sprayed, or attached to the desired region of the skin (affected area). The dosage form of the therapeutic agent composition for dermatitis of the present invention is preferably an external preparation such as an ointment preparation, gel preparation, cream preparation, lotion preparation, liquid preparation, spray preparation, or patch preparation, and particularly preferably, from the viewpoint of ease of application, an ointment preparation, gel preparation, cream preparation or liquid preparation, and more preferably a gel preparation, ointment preparation or liquid preparation consisting of an aqueous solution.

These external preparations can be easily obtained in accordance with heretofore known or well-known methods, by blending a pharmaceutically acceptable base and, as necessary, various additives, with CNP or BNP as an active ingredient or a principal agent.

A gel preparation (suspension base) may be a hydrous gel, an anhydrous gel, or a gel with a low water content comprising a gel-forming material that can swell. It may also be a hydrogel base or a lyogel base, and preferably a transparent hydrogel having an inorganic or organic polymer as a base. Similar to those preparations comprising an oil or fat content, the gel itself is not absorbed by the skin. Hydrogel bases have no fat, have a consistency similar to that of ointment, and aim at increasing the transdermal absorbability of drugs. Lyogel bases are gelled by suspending stearyl alcohol, etc. in propylene glycol, and they have excellent transdermal absorbability and hygroscopicity.

The gel preparation (suspension base) of the present invention may be a gel preparation (suspension base) manufactured by homogenously dispersing CNP or BNP as an active ingredient into a hydrophilic gel base comprising carboxy vinyl polymer, sodium polyacrylate, sodium polyacrylate, (vinyl methyl ether/ethyl maleate) copolymer, polymethacrylate, propylene glycol, etc. Examples of such gel preparations (suspension bases) include gel preparations (suspension bases) wherein ingredients are homogeneously dispersed in a commercially-available long-lasting water-retention agent, such as Lubrajel NP, Lubrajel CG, Lubrajel DV, Lubrajel MS, Lubrajel OIL, Lubrajel TW, Lubrajel DS, which are commercially-available products available from ISP Japan, Ltd., etc.

As used herein, "gel preparation" refers to gel preparations (suspension bases) prepared in accordance with Example 2, comprising dipotassium glycyrrhizinate, allantoin, pyridoxine hydrochloride, xanthan gum, and vitamin E. As used herein, "gel-base preparation" refers to gel preparations (suspension bases) prepared in accordance with Examples 7, 13 or 14, which differ from the "gel preparation" in that the gel-base preparation does not comprise dipotassium glycyrrhizinate, allantoin, pyridoxine hydrochloride, xanthan gum, and vitamin E. The "gel preparations" (suspension base) of the present invention include both "gel preparations" and "gel-base preparations."

A liquid preparation means those wherein an active ingredient consisting of CNP or BNP is dissolved in a base such as alcohol, propylene glycol, polyethylene glycol or water. Preferably, it means a liquid preparation consisting of an aqueous solution wherein either CNP or BNP is dissolved in saline. In the aqueous solutions, a small amount of an organic base such as alcohol, propylene glycol, polyethylene glycol, etc. may be mixed, in addition to saline.

At this time, in order to ensure the extent of bioavailability and to provide more effective liquid preparations, in other words, with the aim of improving the extent of bioavailability upon subcutaneous injection of a bioactive peptide comprising CNP or BNP, it is possible to make the pH of the solution to be 3.0-7.0 by making an acid solution wherein one or more from the group consisting of butyric acid, lactic acid, phosphoric acid, glycine, citric acid, hydrochloric acid, propionic acid, butyric acid, benzoic acid, and salts thereof are combined with the bioactive peptide CNP or BNP as the active ingredient, or by making a polar organic solution wherein one or more from the group consisting of alcohols, and/or N-methyl-2-pyrrolidine, dimethylformamide, dimethyl sulfoxide, and methylparaben are combined with the bioactive peptide CNP or BNP as the active ingredient.

An ointment preparation may be either a grease base or a water-soluble base, and both can be easily obtained in accordance with heretofore known methods. A grease base such as vaseline has little irritation and is odorless, which is superior in protective action of the skin, softening action, crust-removal action, formation of granulation tissue, and epithelialization-stimulating action. A water-soluble base is an ointment having a macrogol base as the main ingredient, and has a strong action to absorb and remove aqueous secretions.

A cream preparation (emulsion base) may be an oil-in-water base (O/W) (vanishing cream) or a water-in-oil base (cold cream). An oil-in-water base has a smaller amount of oil-soluble component than water-soluble component. It has an advantage that the white color of a cream appears to disappear upon application. It extends well and feels good upon application to sweaty skin, thus it is cosmetically superior. In addition, it also has a good absorbability into the skin, thus is applicable to chronic hypertrophic lesions. A water-in-oil base has a smaller amount of water-soluble component than oil-soluble component, and is also called a cold cream because it has a cooling action upon application by extending over the skin.

A lotion preparation means a liquid external preparation wherein CNP or BNP is dissolved or homogeneously dispersed in a liquid. Since ointments and creams tend to adhere to the hair, lotions are suitable for use on the head hair region, etc. The form of lotions may be any of a suspension lotion base, an emulsion lotion, and a solution-type lotion base.

In a patch preparation, a component comprising CNP or BNP is adsorbed to a patch, thereby stimulating absorption of the drug by utilizing the airtight characteristic of the patch. Upon application of the patch, scratching can be prevented.

A spray preparation refers to those wherein CNP or BNP is made into a solution, which is then sprayed by gas pressure. Sprays are convenient when applied to wide areas.

Thus, the therapeutic agent composition for dermatitis of the present invention is a transdermal external preparation comprising an appropriate amount of CNP or BNP and various bases, as well as additives as necessary. To exert drug effects as an external preparation, it is important that the concentration of the active ingredient (CNP or BNP) applied to the skin surface can reach an effective concentration at affected lesions, and that the concentration can be maintained. Accordingly, dosage forms and bases can be appropriately selected depending on the symptoms and patient.

Additives may be appropriately used depending on objectives. As additives, the following may be used.

Vaseline: Vaseline can be used as a base for ointment preparations. Viscosity and consistency vary with temperature, and its hardness differs between winter and summer. Vaseline is one of the safest bases. There are yellow vaseline, and white vaseline with a higher purity; both can be used.

Propylene glycol: Propylene glycol can be used as a solvent, solubilizing agent, or base for drugs.

Paraffin: Paraffin can be used when adjusting the viscosity/consistency of ointment preparations. Since its emulsification is relatively-easy, paraffin may also be used as an oil base for production of creams.

Bees wax (white beeswax): Bees wax is a processed wax of the honeycomb, which can be used as "Japanese Pharmacopoeia" simple ointment by blending with plant-derived fat and oil. White beeswax is a bleached product of bees wax to improve color and odor.

Macrogol: Macrogol is a mixture of polyethylene glycols with different molecular weights. It has good drug solubility and mixing characteristic, absorbs water well; thus is suitable for adsorption and elimination of eluate from mucosa and affected area.

Stearyl alcohol: Stearyl alcohol can be used for emulsion lotions.

Isopropanol: Isopropanol can be used as a solvent or solubilizing agent, etc.

Benzyl alcohol: Benzyl alcohol can be used as a solubilizing agent and preservative, etc.

Parahydroxybenzoate esters (parabens): Parahydroxybenzoate esters can be used as an antiseptic agent, preservative, and stabilizer.

Gelled hydrocarbon: Gelled hydrocarbon is generally called "Plastibase", which is made by making liquid paraffin into a gelled (semi-solid) state using polyethylene.

Citric acid, sodium citrate: Citric acid and sodium citrate can be used as buffering agents or pH adjusters.

Squalene: Squalene is used as a base, and has slightly less oily feeling, being less sticky, than liquid paraffin. Similar to creams, squalene can also be used widely for emulsion lotions.

Lanolins: Lanolins are fats and oils obtained from sheep's wool; although lanolins have drawbacks in terms of color and odor, they are effective for improving the softness of the skin.

Glycerin: Glycerin can be blended in creams, etc. as a moisturizing agent.

Polyoxyethylene hardened castor oil: This can be used as an emulsifying agent, solubilizing agent, etc.

Sorbitan fatty acid ester, glycerin fatty acid ester: They can be used as emulsifying agents, etc.

The therapeutic agent for dermatitis of the present invention may further comprise moisturizing agents (skin softening agents) and symptom-relieving agents, etc. as described below.

Moisturizing agent (skin softening agent): Moisturizing agents provide moisture and oil content to the skin. Moisturizing agents are most effectively used when the skin is already moisturized, for example, just after taking a bath or shower. Components contained in moisturizing agents include glycerin, mineral oil, and vaseline, etc. The form and type of moisturizing agents include lotion preparations, cream preparations, ointment preparations and bathing oils, etc. Those comprising urea, lactic acid and glycolic acid have superior moisturizing effects.

Symptom-relieving agent: Skin diseases are often accompanied by itching. Itching and mild pain can be reduced by blending a sedative drug, specifically, chamomile, eucalyptus, camphor, menthol, zinc oxide, talc, glycerin, and calamine, etc. To suppress itching due to an allergy, antihistamine agents such as diphenhydramine may be comprised.

As such, when manufacturing the therapeutic agents for dermatitis of the present invention, the following various agents may be arbitrarily blended in combination: base, moisturizing agent, ultraviolet absorbing agent, alcohols, chelates, pH adjuster, antiseptic agent, thickening agent, coloring agent, flavor, filling agent, excipient, disintegrating agent, filler, binding agent, coating agent, solubilizing agent, suspending agent, buffer, stabilizing agent, preservative, surfactant, antioxidative agent, dispersing agent, emulsifying agent, dissolving agent, solubilizer, etc. In addition to CNP or BNP, which is the principal agent, various drugs such as antiphlogistic analgetics, sterilizing agents, vitamins, skin softening agents, etc. may be appropriately blended as necessary.

When the skin external-preparation composition of the present invention is used as a skin texture-improving agent, it can be used as a skin-care cosmetic or quasi drug; specific usage forms include cream, foam, skin lotion, facial mask, skin-softening water, skin emulsion, foundation, makeup base, essence, soap, liquid cleanser, bath agent, sun-block cream, suntan oil, or spray-type liquid preparation. These may be easily produced by application of well-known or heretofore known formulation technologies.

Next, as representative examples of preparations of the therapeutic agent composition for dermatitis of the present invention, production of aqueous-solution preparations as a liquid preparation and gel preparation will be described.

In the present invention, one of the preferred external preparations is an aqueous-solution preparation.

Such an aqueous-solution preparation, can be prepared for example, as a liquid preparation with a CNP or BNP concentration of 1-1000 μg/g, by dissolving 0.01-10 mg of human CNP-22 (Peptide Institute, Inc.) or human BNP-32 (Peptide Institute, Inc.) as the principal agent into 10 ml of saline. Here, since the specific gravity of water is 1, the CNP or BNP concentration in this case is 1-1000 μg/g by weight ratio. When the blending ratio is 1 μg/g or less, effects are not sufficient, and sufficient effects can be obtained with blending at a ratio of no more than 500 μg/g. Concentrations of CNP or BNP in an aqueous-solution preparation are preferably 1-500 μg/g, more preferably 10-500 μg/g, furthermore preferably 20-200 μg/g, and particularly preferably 30-100 μg/g.

Gel preparations can be obtained by, in accordance with heretofore known or well-known methods, dissolving an appropriate amount of CNP or BNP into distilled water or saline to make an aqueous solution, and by mixing and stirring a heretofore known or well-known gelling agent with the solution. The final concentration of the CNP or BNP in the gel preparation should be prepared to be preferably 1-500 μg/g, more preferably 10-500 μg/g, furthermore preferably 20-200 μg/g, and particularly preferably 30-100 μg/g.

Examples of the gelling agent consisting of macromolecular inorganic components include hydrous or water-absorbing silicates, such as aluminum silicate, bentonite, magnesium aluminum silicate, and colloid silica. As the gelling agent consisting of macromolecular organic substances, natural, semi-synthetic, or synthetic polymers may be used. Examples of natural and semi-synthetic polymers include, polysaccharides such as cellulose etc., starch, tragacanth, gum arabic, xanthan gum, agar, gelatin, alginic acid and its salts, for example, sodium alginate and its derivatives, lower alkyl cellulose, for example, methyl cellulose or ethyl cellulose, carboxy- or hydroxyl-lower-alkyl-cellulose, for example, carboxymethyl cellulose, or hydroxypropyl cellulose, etc. Examples of synthetic gelling agents include polyvinyl alcohols, polyvinyl pyrrolidones, polyacrylic acids or polymethacrylic acids, etc. Only one kind of these gelling agents, or a mixture of two or more kinds of these may be used.

As necessary, a transdermal absorption aid may be added. Examples of the transdermal absorption aid include, for example, acetic acid, sodium acetate, limonene, menthol, salicylic acid, hyaluronic acid, oleic acid, N,N-diethyl-m-toluamide, n-butyl stearate, benzyl alcohol, isopropyl myristate, isopropyl palmitate, polypropylene glycol, crotamiton, diethyl sebacate, N-methyl pyrrolidone, N-ethyl pyrrolidone, lauryl alcohol, etc. In addition, an antiseptic agent and an antioxidant may be added as necessary.

The concentration of CNP or BNP in the therapeutic agent composition for dermatitis of the present invention may be appropriately selected according to symptoms, age, and dosage form, etc. The preferable concentration of CNP or BNP is, for external preparations such as liquid preparations, gel preparations and lotion preparations, etc., 1-500 μg/g, more preferably 10-500 μg/g, furthermore preferably 20-200 μg/g, and particularly preferably 30-100 μg/g. For younger patients or patients with sensitive skin, the use of 20-100 μg/g concentration is preferred. The concentration of CNP or BNP in a gel preparation and ointment preparation is preferably 1-500 μg/g, more preferably 10-500 μg/g, and furthermore preferably 20-200 μg/g, and particularly preferably 30-100 μg/g. The concentration of CNP or BNP in a liquid preparation is preferably 1-500 μg/ml, more preferably 10-500 μg/ml, furthermore preferably 20-200 μg/ml, and particularly preferably 30-100 μg/ml. Here, since the specific gravity of the solution used in the liquid preparation of the present invention is almost 1, when the concentration of CNP or BNP in the liquid preparation is indicated in the units of μg/g, it is equivalent to the indication in the units of μg/ml for the concentration of CNP or BNP.

The administration of the therapeutic agent composition for dermatitis of the present invention differs depending on symptoms, age and dosage form, etc.; however, administration is normally once or twice a day, and the duration of administration is from 1 to 10 days.

EXAMPLE 1

Diagnosis and Evaluation of Subjects

First, prior to administration of the CNP preparation or BNP preparation of the present invention, subjects were diagnosed and evaluated. The methods for diagnosis and evaluation of the subjects are as follows.

1. Diagnosis of Subjects:

All the subjects were patients for whom administration of existing external drugs such as steroids, etc. was ineffective. The diagnosis and treatment of these subjects were performed by the present inventor as a medical doctor.

2. Evaluation of Symptoms:

The evaluation of symptoms of atopic dermatitis was performed in accordance with, in principle, "2005 Guideline for the Treatment of Atopic Dermatitis by the Scientific Research Division of the Health and Welfare Ministry of Japan" (hereinafter, simply referred to as "Guideline 2005") by the classification into four levels as shown in Table 1.

TABLE 1

| Evaluation of symptoms | |
|---|---|
| Mild | Only mild rash is observed regardless of size. |
| Moderate | Rash with severe inflammation is observed in less than 10% of the body surface area. |
| Severe | Rash with severe inflammation is observed over 10% or more and less than 30% of the body surface area. |
| Most severe | Rash with severe inflammation is observed over 30% or more of the body surface area. |

"Mild rash": means lesions mainly characterized by mild erythema, dryness, and desquamation.
"Rash with severe inflammation": means lesions associated with erythema, papules, erosions, infiltration and lichenification, etc.

In addition, the severity level of the rash at each region was determined in accordance with "Guidelines for Management of Atopic Dermatitis by the Japanese Dermatological Association" (hereinafter, simply referred to as the "Dermatological Association Guideline"), as shown in Table 2.

TABLE 2

| Severity level of rash | |
|---|---|
| Minor | Mainly characterized by dry symptoms with a little inflammation symptoms. |
| Mild | Mainly characterized by dryness and mild erythema and scales, etc. |
| Moderate | Mainly characterized by up to mild erythema, scales, a small number of papules and abrasion, etc. |
| Severe | Mainly characterized by erythema with severe swelling/edema/infiltration/or lichenification, many papules, severe scales, adhesion of crusts, vesicles, erosions, numerous excoriations, and prurigo nodularis, etc. |

The severity level of the rash of each region was also determined using SCORAD (SCORing of Atopic Dermatitis) index, which was proposed by the European Task Force on Atopic Dermatitis and is widely used throughout the world. With the SCORAD index, a severity level is determined by the summation of rating scores for each of (A) extent %, (B) intensity of rash, (C) subjective symptoms. In the evaluation of the present study, the intensity of rash (B) was evaluation with the following 4 levels: 0: none, 1: mild, 2: moderate, 3: severe, with respect to 6 items: erythema, edema/papulation, oozing/crusting, excoriation, lichenification, and dryness. Since the regions of application were limited to parts of the body instead of the whole body, the total score was not determined in accordance with a specified calculation formula of the severity-level classification by SCORAD. Instead, a score, which is a simple summation of the rating scores of the 6 items of intensity of rash at the region of application before and after the application, was used. Since choice of the external therapeutic method, which is a primary therapy, is determined based on the severity of each rash, the severity level of each rash is the most important factor in selecting external therapy as well as in predicting therapeutic outcomes. Details of the SCORAD index are described, for example, in C. Gelmetti and C. Colonna, Allergy, Vol. 59, Supplement 78, p. 61, 2004.

3. Test Method:

In general, in order to evaluate the effects of external preparations on individual cases, a right/left comparative method is suitable. It is a method wherein, the therapeutic effects of active ingredients are identified by, for example, applying an external preparation comprising the active ingredient to be tested is applied to the left side of the affected region, and an external preparation without the active ingredient is applied to the right side. The preparations of the present invention were tested by right/left comparative method in preliminary tests. However, considering the medical ethics, preliminary tests by the right/left comparative method were limited to a minimum degree, and when preliminary tests were not performed, therapeutic effects were evaluated by the comparison between before and after application.

EXAMPLE 2

1. Production of CNP Gel Preparation 0.1 g of methyl parahydroxybenzoate (product name: Mekkins M, Ueno Fine Chemicals Industry), 0.2 g of phenoxyethanol, 3.0 g of 1,2-pentanediol, 6.0 g of concentrated glycerin, 0.1 g of dipotassium glycyrrhizinate, 0.1 g of allantoin, and 0.05 g of pyridoxine hydrochloride are added and dissolved in 75.72 g of purified water. Then 6.0 g of Lubrajel from Showa Denko K.K. (a mixture consisting of 4.674 g of purified water, 0.12 g of carboxy vinyl polymer, 0.006 g of sodium polyacrylate, and 1.2 g of glycerin), 0.44 g of carboxy vinyl polymer (product name: Carbopol 940, Lubrisol Advanced Materials, Inc.), and 8.00 g of 1% xanthan gum solution (product name: Keltrol T, CP Kelco) were added to this solution and stirred and mixed, then 0.04 g of natural vitamin E was further added to make a homogenous mixed solution. Finally, 0.25 g of potassium hydroxide was added for neutralization, and the solution was sufficiently stirred to form a gelled state to obtain a gel preparation.

The CNP gel preparation was prepared as follows: 3 mg of human CNP-22 (Peptide Institute, Inc.) as the principal agent was dissolved in 3 ml of saline, and 100 μl of the resulting solution was diluted with 400 μl of saline to adjust the concentration to be 200 μg/ml, then 1.5 ml of the resulting solution was mixed and stirred in 8.5 g of the above gel preparation. The CNP concentration of thus-obtained gel preparation is 30 μg/g.

EXAMPLE 3

2. Production of CNP Aqueous-Solution Preparation

The CNP aqueous-solution preparation was prepared as follows: 3 mg of human CNP-22 (Peptide Institute, Inc.) as the principal agent was dissolved in 3 ml of saline, and 100 μl of the resulting solution was diluted with 900 μl of saline to prepare the aqueous-solution preparation with a CNP concentration of 100 μg/ml. CNP aqueous-solution preparations with a CNP concentration of 50 μg/ml and 200 μg/ml were prepared similarly.

EXAMPLE 4

3. Diagnosis of Subjects:

Prior to administration of the CNP gel preparation and CNP aqueous-solution preparation of the present invention, history taking from the subjects, scratch tests for allergens, and a diagnosis were conducted. Table 3 (subjects 1-5) and Table 5 (subjects 6-10) show the results of the subjects' history taking and diagnosis, i.e., sex, age, onset and course of disease, family history, past history, scratch test results, diagnostic findings, and symptom evaluation based on "Guideline 2005" of the subject in each case.

EXAMPLE 5

4. Therapeutic Effects on Subjects

Therapeutic effects of the CNP gel preparation and CNP aqueous-solution preparation of the present invention are shown in Table 4 (subjects 1-5) and Table 6 (subjects 6-10). In Tables 4 and 6, "itching sensation" represents a comparison of the itching sensation evaluated using the visual analogue scale method before and after treatment. Similarly, "non-recurrence period" refers to the period after discontinuation of the treatment by the preparation of the present invention subsequent to improvement of symptoms, in which relapse of the symptoms did not occur. In order to evaluate objectively, photographs before and after application of CNP preparations were taken for all cases. Of these, photographs of some cases are shown in the figures.

TABLE 3

| | Diagnosis prior to application of CNP gel preparation. | | | | |
|---|---|---|---|---|---|
| | Subject | | | | |
| | Subject 1 | Subject 2 | Subject 3 | Subject 4 | Subject 5 |
| Case | Case 1 | Case 6 | Case 5 | Case 9 | Case 10 |
| Sex | Female | Female | Male | Female | Male |
| Age | 21 years old | 39 years old | 24 years old | 9 months old | 32 years old |

TABLE 3-continued

Diagnosis prior to application of CNP gel preparation.

| | Subject | | | | |
|---|---|---|---|---|---|
| | Subject 1 | Subject 2 | Subject 3 | Subject 4 | Subject 5 |
| Onset and course of disease | Developed in infancy, having recurrent eczema with itching. | Developed at 19 years of age, having recurrent eczema with itching. She is in the state of erythroderma posteczematosa presumably due to long period of steroid external therapy, and skin flush and desquamation are observed over the whole body. | Have repeated chronic recurrent dermatitis with itching from elementary school. Generalized type; symptoms on the face tend to worsen upon use of organic solvents and lack of sleep. | Developed at 10 days after birth; generalized-type recurrent eczema with itching. The face becomes occasionally full of excoriations due to scratching the skin all the time. Horse oil has been used for moisturization. | Developed in infancy, having recurrent eczema with itching, generalized type; he is in a state of erythroderma posteczematosa; chills, skin flush and scales are observed. |
| Family history | Mother and elder brother; Atopic dermatitis, allergic rhinitis | Mother; Atopic dermatitis | Mother; Bronchial asthma | Father; Atopic dermatitis | None |
| Past history | Allergic rhinitis | Child asthma | Allergic rhinitis | | Child asthma, Allergic rhinitis |
| Scratch test | House dust: 5+ Mite: 5+ | House dust: 3+ Mite: 2+ | House dust: 2+ Mite: 2+ Cedar: 1+ Orchard grass: 2+ Ragweed: 1+ | House dust: 1+ Mite: 2+ Egg white: 2+ Egg yolk: 2+ | House dust: 2+ Mite: 3+ |
| Diagnostic findings | Infiltrative erythema with itching associated with sleep disturbance, lichenified lesions, and erythema are observed over the whole body. | Infiltrative erythema with itching associated with sleep disturbance, lichenified lesions, and erythema are observed over the whole body. severe scales and infiltrative erythema with strong burning sensation are observed on the face. | Mild-to-severe level erythema, scales and excoriation are observed over the whole body. | Erythema, papules, scales and numerous excoriations are observed over the whole body. | Infiltrative erythema with itching associated with sleep disturbance, lichenified lesions, and erythema are observed over the whole body. In particular on the upper limbs, infiltrative erythema with strong burning sensation is repeatedly worsened. |
| Symptoms of application regions | Rash on the face and neck is mainly characterized by severe infiltration, and erythema with edema. | Rash on the face is mainly characterized by severe infiltration, erythema, and numerous excoriations. | Rash on the back is mainly characterized by severe swelling, erythema with edema, and scales. | Rash on the both forearms is mainly characterized by erythema, papules, scales, and numerous excoriations. | Rash on the forearms is mainly characterized by severe swelling, infiltration, erythema, scales, papules, erosions and numerous excoriations. |
| Effects of steroid external drug | Steroid external drug had no effects on erythema, infiltrative erythema and scales on the face and neck. | She is in the state of erythroderma posteczematosa presumably due to steroid external therapy. | Steroid external therapy relieves the infiltrative erythema on the back and face only insufficiently, and the symptoms relapse soon. | (Parents) desire use treatment without steroids. | He is in the state of erythroderma posteczematosa presumably due to long-term steroid external therapy. |
| Evaluation of symptoms | Most severe | Most severe | Severe | Most severe | Most severe |

TABLE 4

Therapeutic effects of CNP gel preparation.

| | Subject 1 | Subject 2 | Subject 3 | Subject 4 | Subject 5 (FIG. 1) |
|---|---|---|---|---|---|
| Case | Case 1 | Case 6 | Case 5 | Case 9 | Case 10 |
| Sex | Female | Female | Male | Female | Male |
| Age | 21 years old | 39 years old | 24 years old | 9 months old | 32 years old |
| Dosage form | CNP gel preparation | CNP gel preparation | CNP gel preparation | CNP gel preparation | CNP gel preparation |
| Dosage | 30 µg/g | 30 µg/g | 30 µg/g | 30 µg/g | 30 µg/g |
| Number of administration | Twice a day | Twice a day | Twice at 20-min interval | Twice at 20-min interval | 3 times at 20-min interval |
| Days of administration | 4 days | 3 days | Only 1 day when visiting the clinic. | Only 1 day when visiting the clinic. | Only 1 day when visiting the clinic. |
| Application region | Face and neck | Face and neck | Back | Forearm | Upper limb |
| Severity level of rash by Dermatological Association Guideline | Before: severe After: mild | Before: severe After: mild | Before: severe After: mild | Before: moderate After: mild | Before: severe After: moderate |
| Severity level evaluation of the rash region by SCORAD (before application) | Erythema: 3 Edema/papulation: 3 Oozing/crusting: 1 Excoriation: 1 Lichenification: 2 Dryness: 3 Total: 13/18 | Erythema: 3 Edema/papulation: 3 Oozing/crusting: 2 Excoriation: 2 Lichenification: 3 Dryness: 3 Total: 16/18 | Erythema: 3 Edema/papulation: 3 Oozing/crusting: 2 Excoriation: 2 Lichenification: 1 Dryness: 2 Total: 13/18 | Erythema: 2 Edema/papulation: 2 Oozing/crusting: 2 Excoriation: 2 Lichenification: 1 Dryness: 2 Total: 11/18 | Erythema: 3 Edema/papulation: 3 Oozing/crusting: 3 Excoriation: 3 Lichenification: 3 Dryness: 3 Total: 18/18 |
| Severity level evaluation of the rash region by SCORAD (after application) | Erythema: 1 Edema/papulation: 1 Oozing/crusting: 1 Excoriation: 1 Lichenification: 0 Dryness: 1 Total: 5/18 | Erythema: 1 Edema/papulation: 0 Oozing/crusting: 0 Excoriation: 0 Lichenification: 0 Dryness: 1 Total: 2/18 | Erythema: 1 Edema/papulation: 1 Oozing/crusting: 1 Excoriation: 1 Lichenification: 0 Dryness: 1 Total: 5/18 | Erythema: 1 Edema/papulation: 1 Oozing/crusting: 1 Excoriation: 0 Lichenification: 0 Dryness: 1 Total: 4/18 | Erythema: 1 Edema/papulation: 1 Oozing/crusting: 0 Excoriation: 1 Lichenification: 2 Dryness: 2 Total: 7/18 |
| Detailed description of improvement status of symptoms | After 4 days of application of 30-µg/g CNP gel preparation to both sides of the face and neck twice a day, erythema was markedly reduced, scales disappeared and the skin texture became fine and softened. | After 3 days of application of 30-µg/g CNP gel preparation to both sides of the face and neck twice a day, remarkable effects were shown and erythema was almost disappeared, in addition, scales disappeared and the skin texture became fine. | After application of 30-µg/g CNP gel preparation to left side of the back twice at 20-min interval, erythema with swelling on the left side of the back was markedly improved 45 min, to a mild symptom characterized by mild erythema. | After application of 30-µg/g CNP gel preparation to the right forearm twice at 20-min interval, scaly erythema and infiltration on the right cubital fossa were reduced and erythema, papules and scales on the forearms were improved. | After application of 30-µg/g CNP gel preparation to the right upper limb at 20-min interval, subjective burning sensation on the right side (where CNP gel preparation was applied) subsided, and infiltration, scales and erythema on the right side were markedly improved compared to those on the left side. |
| Itching sensation | Before: 10 After: 0 | Before: 10 After: 1 | Before: 10 After: 2 | (Infant) | Before: 10 After: 3 |
| Non-recurrence period | 2 weeks | 7 days | 7 days | 2 weeks or more | 7 days |

TABLE 5

Diagnosis prior to application of CNP aqueous-solution preparation.

| | Subject 6 (FIG. 2) | Subject 7 (FIG. 3) | Subject 8 | Subject 9 | Subject 10 |
|---|---|---|---|---|---|
| Case | Case 2 | Case 7 | Case 8 | Case 3 | Case 4 |
| Sex | Female | Female | Female | Female | Male |
| Age | 41 years old | 29 years old | 36 years old | 38 years old | 32 years old |
| Onset and course of disease | Developed at 7 years of age, having recurrent eczema with itching; in particular infiltrative erythema on the face tends to worsen acutely; herpes virus infection on the face as a complication has been repeated. | Developed in infancy; symptoms worsened since about a half year ago, showing severe infiltrative erythema on the four limbs and face. | Developed in infancy, having recurrent eczema with itching; she presents with severe infiltration and erythema over the whole body; without application of "the strongest" steroid external drugs, exudate leaks out. | Developed at 2 months after birth; she presents with generalized-type recurrent eczema with itching. | He presents with chronic recurrent dermatitis with itching repeatedly, which extended to the whole body since 2 years ago. |
| Family history | None | | Elder brother; Atopic dermatitis | None | Mother; Atopic dermatitis |
| Past history | Child asthma | Allergic rhinitis | Child asthma | Bronchial asthma | Allergic rhinitis |
| Scratch test | House dust: 3+ Mite: 3+ | House dust: 2+ Mite: 2+ Orchard grass: 2+ Ragweed: 1+ | House dust: 3+ Mite: 3+ Cedar: 3+ Orchard grass: 3+ Ragweed: 2+ | House dust: 2+ Mite: 3+ | House dust: 2+ Mite: 2+ Cedar: 2+ Orchard grass: 2+ Ragweed: 1+ |
| Diagnostic findings | Infiltrative erythema with itching associated with sleep disturbance, lichenified lesions, and erythema are observed over the whole body. On the face; she presents with repeated exacerbation of infiltrative erythema with a strong burning sensation associated with capillary dilation. | Infiltrative erythema lichenified lesions, erythema, severe scales, adhesion of crusts, and numerous excoriations are observed on the four limbs and face. | Infiltrative erythema with itching associated with sleep disturbance, lichenified lesions, and erythema are observed over the whole body. | Infiltrative erythema, lichenified lesions, erythema, severe scales, adhesion of crusts, and numerous excoriations are observed over the whole body; she is in the state of erythroderma posteczematosa. | Infiltrative erythema, scales, and numerous excoriations are observed over the whole body. |
| Symptoms of application regions | Rashes on the face are mainly characterized by erythema with severe swelling, infiltration or lichenification, as well as papules, erosions and numerous excoriations. | Rashes on the face are mainly characterized by erythema with severe lichenification, as well as papules, erosions, scales and numerous excoriations. | Rashes on the face and neck are mainly characterized by severe infiltration, and erythema with edema. | Rashes on the face are mainly characterized by erythema with lichenification, as well as papules, erosions, scales, and numerous excoriations. | Rashes on the forearms are mainly characterized by erythema with severe swelling, as well as scales, and excoriations. |
| Effects of steroid external drug | Not reduced by steroid external therapy. | Although infiltrative erythema on the face is reduced by steroid external therapy, it easily relapses and tends to worsen. | Steroid external drugs are not effective for erythema, infiltrative erythema and scales on the face and neck. | Not reduced even by "very strong" steroid external therapy. | Upon discontinuation of steroid external therapy, he is in a state of erythroderma with appearance of skin flush and desquamation over the whole body. |

TABLE 5-continued

Diagnosis prior to application of CNP aqueous-solution preparation.

|  | Subject | | | | |
| --- | --- | --- | --- | --- | --- |
|  | Subject 6 (FIG. 2) | Subject 7 (FIG. 3) | Subject 8 | Subject 9 | Subject 10 |
| Evaluation of symptoms | Most severe | Severe | Most severe | Most severe | Severe |

TABLE 6

Therapeutic effects of CNP aqueous-solution preparation.

|  | Subject | | | | |
| --- | --- | --- | --- | --- | --- |
|  | Subject 6 (FIG. 2) | Subject 7 (FIG. 3) | Subject 8 | Subject 9 | Subject 10 |
| Case | Case 2 | Case 7 | Case 8 | Case 3 | Case 4 |
| Sex | Female | Female | Female | Female | Male |
| Age | 41 years old | 29 years old | 36 years old | 38 years old | 32 years old |
| Dosage form | CNP aqueous-solution preparation | CNP aqueous-solution preparation | CNP aqueous-solution preparation | CNP aqueous-solution preparation | CNP aqueous-solution preparation |
| Dosage | 100 µg/ml | 100 µg/ml | 100 µg/ml | 100 µg/ml | 100 µg/ml |
| Number of administrations | Twice a day | Twice a day | Twice a day | Twice a day | 3 times at 20-min interval |
| Days of administration | 4 days | 4 days | 10 days | 4 days | Only 1 day when visiting the clinic. |
| Application regions | Face and neck | Face | Face and neck | Face | None |
| Severity level of rash by Dermatological Association Guideline | Before: severe After: mild | Before: severe After: mild | Before: severe After: moderate | Before: severe After: minor | Before: severe After: minor |
| Severity level evaluation of the rash region by SCORAD (before application) | Erythema: 3 Edema/papulation: 2 Oozing/crusting: 2 Excoriation: 1 Lichenification: 3 Dryness: 3 Total: 14/18 | Erythema: 3 Edema/papulation: 3 Oozing/crusting: 2 Excoriation: 2 Lichenification: 2 Dryness: 2 Total: 14/18 | Erythema: 3 Edema/papulation: 3 Oozing/crusting: 1 Excoriation: 2 Lichenification: 3 Dryness: 3 Total: 15/18 | Erythema: 3 Edema/papulation: 2 Oozing/crusting: 2 Excoriation: 2 Lichenification: 2 Dryness: 3 Total: 14/18 | Erythema: 3 Edema/papulation: 2 Oozing/crusting: 2 Excoriation: 2 Lichenification: 2 Dryness: 2 Total: 13/18 |
| Severity level evaluation of the rash region by SCORAD (after application) | Erythema: 0 Edema/papulation: 0 Oozing/crusting: 0 Excoriation: 0 Lichenification: 1 Dryness: 1 Total: 2/18 | Erythema: 1 Edema/papulation: 0 Oozing/crusting: 1 Excoriation: 1 Lichenification: 0 Dryness: 1 Total: 4/18 | Erythema: 1 Edema/papulation: 1 Oozing/crusting: 1 Excoriation: 0 Lichenification: 2 Dryness: 1 Total: 6/18 | Erythema: 1 Edema/papulation: 0 Oozing/crusting: 0 Excoriation: 1 Lichenification: 0 Dryness: 1 Total: 3/18 | Erythema: 0 Edema/papulation: 1 Oozing/crusting: 0 Excoriation: 0 Lichenification: 0 Dryness: 1 Total: 2/18 |
| Detailed description of improvement status of symptoms | After 4 days of application of 100 µg/ml CNP aqueous-solution preparation to both sides of the face and neck twice a day, erythema was markedly reduced and scales disappeared, and the skin texture became fine. | On 4th day of application of 100 µg/ml CNP aqueous-solution preparation, all of the infiltrative erythema, lichenified lesions, erythema, severe scales, adhesion of crusts, and numerous excoriations on the face were markedly improved. | After 3 days of application of 100-µg/ml CNP aqueous-solution preparation to both sides of the face and neck twice a day, erythema and infiltration were reduced and erosions were alleviated. | After 4 days of application of 100-µg/ml CNP aqueous-solution preparation, all of the infiltrative erythema, lichenified lesions, erythema, severe scales, adhesion of crusts, and numerous excoriations were markedly improved. | Sixty (60) min after the application of 100 µg/ml CNP aqueous-solution preparation 3 times at 20 min interval, subjective itching sensation on the right forearm was reduced and erythema was markedly improved, and inflammation and dryness symptoms almost disappeared. |
| Itching sensation | Before: 10 After: 1 | Before: 10 After: 0 | Before: 10 After: 4 | Before: 10 After: 0 | Before: 10 After: 1 |
| Non-recurrence period | 5 days | 2 weeks or more | 5 days | 2 weeks | 2 weeks |

EXAMPLE 6

Details of the test examples of the CNP gel preparation and CNP aqueous-solution preparation summarized in Tables 3 to 6 are as follows.
CNP Gel Preparation, Test-Example 1 (Case 1; Subject 1; See Tables 3 and 4):
Preliminary Test:

In the subject of Case 1, erythema, infiltrative erythema, and scales were observed on the face and neck. Steroid external drugs did not show any effects on these erythema, infiltrative erythema, and scales.

Therefore, the CNP gel preparation of the present invention was applied only to the right side of the face and neck of the subject, and a gel without CNP as the active ingredient was applied to the left side, twice a day, and symptoms were observed. The CNP gel preparation used was the CNP gel preparation (30 µg/g) obtained in Example 2.
Preliminary Test Results:

Ten min after the application, as a subjective symptom, a burning sensation subsided on the right side on which the CNP gel preparation was applied, and 30 min later, erythema also began to become less severe to a certain degree. In addition, there were no irritation symptoms due to the application of the CNP gel preparation.
Treatment and its Outcome:

From the above findings of the preliminary test, the CNP gel preparation of the present invention was judged to be effective in this case without side effects; therefore its application to both sides of the face and neck twice a day was started. As a result, erythema clearly improved by days after the start of the treatment, while scales disappeared, and the skin was softened and its texture became finer. Furthermore, given that the itching sensation level before the application of the CNP gel preparation is rated as 10, then the itching sensation level after the application was 0, i.e., it is completely disappeared. Here, evaluation of the itching sensation level was performed by the visual analogue scale method.

Clinical follow-up after this revealed that, when the application of the CNP gel preparation was discontinued for 4 or 5 days, recurrence of minor erythema and scales was observed, but the symptoms did not worsen acutely, and the symptoms were improved without prolongation by the application of the CNP gel preparation for several days. It was also effective for the exacerbation before the start of a menstrual period, and symptoms were improved to almost normal conditions with little inflammatory symptom by the next morning, by the application twice a day in the morning and evening.
CNP Gel Preparation, Test Example 2 (Case 6; Subject 2; See Tables 3 and 4):
Treatment and its Outcome:

The subject of Case 6 presented with infiltrative erythema with itching associated with sleep disturbance, lichenified lesions, and erythema over the whole body, and also infiltrative erythema with severe scales and a strong burning sensation on the face. In addition, the subject was in a state of erythroderma posteczematosa presumably due to the long-term steroid external therapy, presenting with skin flush and desquamation over the whole body. The severity level of the rash on the face was characterized mainly by severe infiltration, erythema and numerous excoriations.

Under such conditions, using the right/left comparative method, initially, the CNP gel preparation with a concentration of 30 µg/g obtained in Example 2 was applied only to the right side of the face, and a gel alone was applied to the left side of the face. As a result, immediately after the application of the CNP gel preparation, a burning sensation on the right side subjectively subsided, and erythema began to improve. Moreover, no symptoms of irritation due to the application of the CNP gel preparation were observed.

Subsequently, the CNP gel preparation with a concentration of 30 µg/g was applied to both sides of the face and the neck twice a day. As a result, significant effects were observed; erythema almost disappeared after 3 days, and scales disappeared and the texture of the skin became finer.

The severity level of the rash on the face was improved by the application of the CNP gel preparation of the present invention from severe to mild, according to the classification based on the Dermatological Association Guideline. Furthermore, by the application of the CNP gel preparation of the present invention, the itching sensation level was improved from 10 to 1 according to the visual analogue scale method.

Clinical follow-up after this revealed that, around 3 days after the discontinuation of the present CNP gel preparation, mild erythema recurred but did not worsen any further. In this case, when the present CNP gel preparation was re-applied, these symptoms disappeared after 3 or 4 days
CNP Gel Preparation, Test Example 3 (Case 5; Subject 3; See Tables 3 and 4):
Treatment and its Outcome:

This test mainly aimed at evaluation of absorbability of the CNP gel preparation at the dorsal region.

The subject of Case 5 had moderate to severe erythema, scales, and excoriations over the whole body, and the severity level of the rash on the back was characterized mainly by severe swelling, erythema with edema, and scales.

Under such condition, using the right/left comparative method, the CNP gel preparation with a concentration of 30 µg/g obtained in Example 2 was applied only to the left side of the back of the subject twice at an interval of 20 min, and a gel alone was applied to the right side of the back. As a result, erythema with swelling improved markedly on the left side after 45 min, to a mild symptom characterized mainly by mild erythema. The description in Table 4 shows the results of evaluation of the therapeutic effects of the CNP gel preparation at this point.

The above gel preparation (concentration of 30 µg/g) was applied to the face and neck of the same subject without right/left comparisons, twice a day for 3 days. As a result, erythema and scales on the face and neck markedly improved to be diagnosed as being a mild degree. Namely, the severity level on the face and neck was improved from severe to mild, according to the classification based on the Dermatological Association Guideline.

These test results demonstrated that the CNP gel preparation of the present invention has excellent transdermal absorbability not only on the face, neck and forearms, but also on the dorsal region.
CNP Gel Preparation, Test Example 4 (Case 9; Subject 4; See Tables 3 and 4):
Treatment and its Outcome:

The subject of Case 9 was a female infant suffering from recurrent eczema with itching over the whole body, and erythema, papules, scales and numerous excoriations were observed over the whole body. In addition, erythema, papules, scales and numerous excoriations were observed on both forearms.

Under such condition, the CNP gel preparation with a concentration of 30 µg/g obtained in Example 2 was applied only to the right forearm of the subject. The application was performed twice at an interval of 20 min. As a result, desquamative erythema and infiltration on the right cubital fossa were reduced, and erythema, papules and scales on the forearm were also improved.

Of particular note in this case is that improved condition was maintained for 2 weeks or longer after application only twice at the time of visiting the clinic. The result of this test showed that scales disappeared, and skin texture became finer and softened, thus the effectiveness in infant were also evident.

CNP Gel Preparation, Test Example 5 (Case 10; Subject 5; see Tables 3 and 4):

Treatment and its Outcome:

The subject of Case 10 developed atopic dermatitis in infancy; suffering from recurrent eczema with itching; presenting with infiltrative erythema with itching associated with sleep disturbance, lichenified lesions and scales over the whole body; being associated chilly sensation; and the subject was diagnosed as erythroderma posteczematosa. Particularly on the upper limbs, infiltrative erythema with a strong burning sensation was observed, signifying its intractable nature. The rash on both upper limbs was mainly characterized by severe swelling, infiltration, erythema and erosions, with numerous excoriations.

To this subject, using the right/left comparative method, the CNP gel preparation with a concentration of 30 μg/g obtained in Example 2 was applied only to the right upper limb at an interval of 20 min, and a gel alone was applied to the left upper limb. As a result, the burning sensation on the right side, where the CNP gel preparation was applied, subsided after 60 min as a subjective symptom, and the infiltration, scales and erythema on the right side were markedly improved compared to the right arm prior to the application, and compared to the left arm where the gel preparation without CNP was applied three times at 20 min interval. FIG. 1 is a photograph showing the result of application of the CNP gel preparation of the present invention to the subject.

CNP Aqueous-Solution Preparation, Test Example 1 (Case 2; Subject 6; see Tables 5 and 6):

Preliminary Test:

In the subject of Case 2, the rash on the face was characterized mainly by erythema with severe swelling, infiltration and lichenification, papules, erosions, and numerous excoriations. The subject had a burning sensation as a subjective symptom. In addition, the subject had a history of recurring herpes virus infections, thus this is a case for which tacrolimus external therapy cannot be used.

As in the case of the test example 1, the CNP aqueous-solution preparation with a concentration of 100 μg/ml obtained in Example 3 was applied only to the right side of the face of the subject, and saline alone was applied to the left side.

Preliminary Test Results:

Ten min after the application, the burning sensation subsided on the right side of the face on which the CNP aqueous-solution preparation had been applied, and erythema on the right side of the face also began to be slightly improved 30 min later. In addition, irritation symptoms attributed to the application of the CNP aqueous-solution preparation were completely absent. Since the subject felt that the burning sensation and heaviness on the skin were reduced and that the preparation permeated into the skin, the preparation of the present invention was considered to be effective for reducing subjective symptoms. Moreover, apparent improvement in infiltration and erythema was observed.

Treatment and its Outcome:

From the findings of the preliminary test above, the CNP aqueous-solution preparation of the present invention was judged to be effective without side effects in this case; therefore, its application to both sides of the face and neck twice a day was initiated. As a result, erythema was clearly improved after 4 days, while the scales disappeared and the texture of the skin became finer. Furthermore, while the itching sensation level before application of the CNP aqueous-solution preparation was scored 10 based on the visual analogue scale method, it was markedly improved to 1 after the application.

Figure 2:
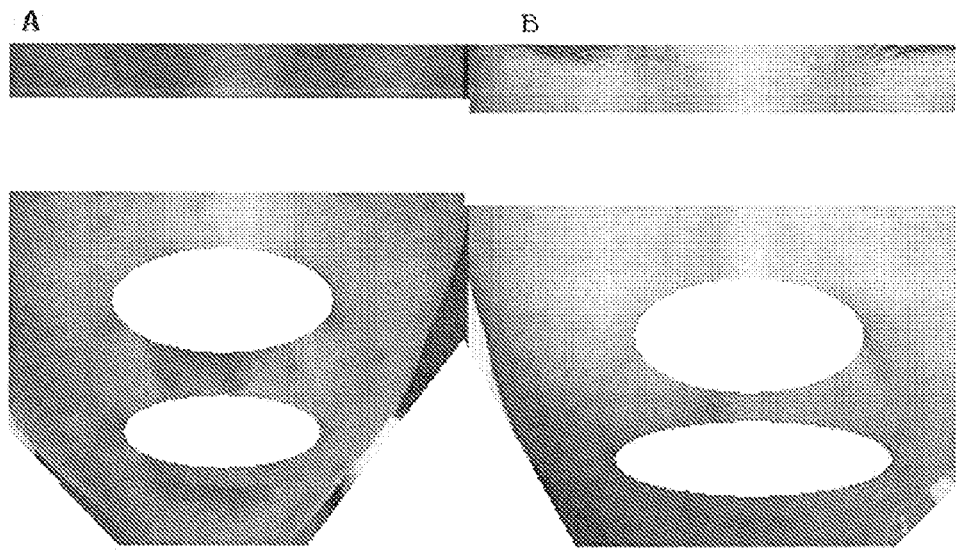
FIG. 2 is a photograph showing the effects of a CNP aqueous-solution preparation of the present invention when it was applied to a patient who had a rash mainly characterized by severe swelling, infiltration, erythema with lichenification, papules, erosions, and numerous excoriations on the face. A shows the state before application, and B shows the state after application of the CNP aqueous-solution preparation with a concentration of 100 µg/ml twice a day for 4 days. (Refer to Case 2 of the CNP aqueous-solution preparation; subject 6; Tables 5 and 6)

Clinical follow-up after this revealed that, when the application of the CNP aqueous-solution preparation was discontinued for 4 or 5 days, mild erythema recurred, but the symptoms did not worsen any further. In addition, this recurrence of mild erythema was improved again by further application of the CNP aqueous-solution preparation for a period of 3-4 days. FIG. 2 is a photograph showing the results of application of the CNP aqueous-solution preparation of the present invention to the subject.

Moreover, the symptoms of this subject were markedly improved by continuous application of the CNP aqueous-solution preparation; accordingly, the subject became able to wear makeup. Furthermore, the safety and efficacy of the present preparation as an externally applicable preparation to the patients with herpes virus infection complications, to whom tacrolimus external therapy cannot be applied, has been demonstrated by this test.

Dosage-Finding Study:

A dose-finding study was performed with the same subject. With the CNP solution preparation with a CNP concentration of 50 μg/ml, the healing process of the skin was slightly slower compared to that with the concentration of 100 μg/ml, and the treated skin was slightly rough to the touch. Although the CNP aqueous-solution preparation with a CNP concentration of 200 μg/ml remained to cause no irritation, this did not double its effectiveness.

CNP Aqueous-Solution Preparation, Test Example 2 (Case 7; Subject 7; see Tables 5 and 6):

Treatment and its Outcome:

The subject of Case 7 presented with infiltrative erythema, lichenified lesions, erythema, severe scales, adhesion of crusts and numerous excoriations on the four limbs and face, and the rash on the face was characterized mainly by erythema with lichenification, papules, erosions, scales and numerous excoriations.

Under such conditions, using the right/left comparative method, initially, the CNP aqueous-solution preparation with a concentration of 100 μg/ml obtained in Example 3 was applied only to the right side of the face, and saline alone was applied to the left side of the face.

Figure 3:
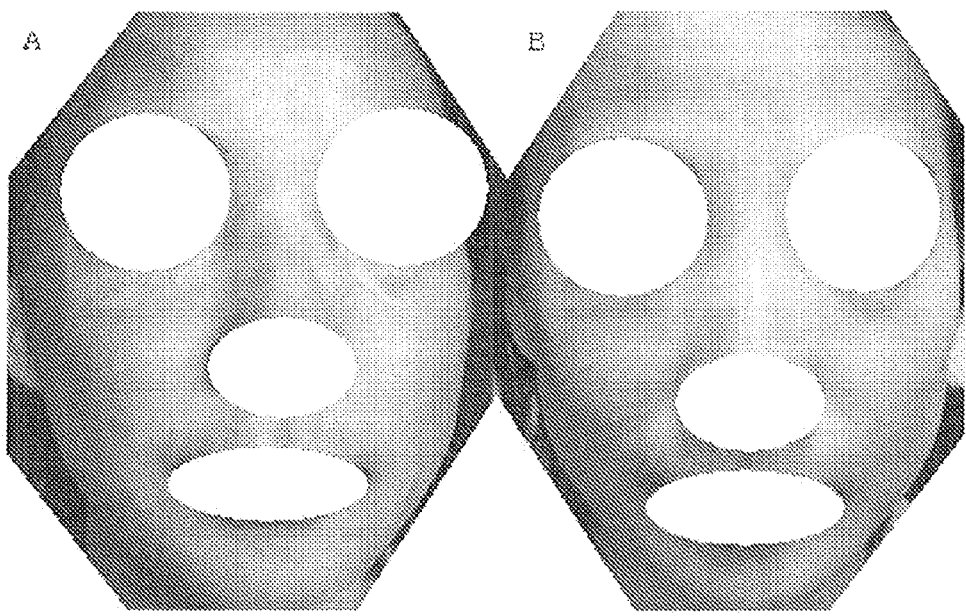
FIG. 3 is a photograph showing the effects of a CNP aqueous-solution preparation of the present invention when it was applied to a patient who had a rash mainly characterized by erythema with lichenification, papules, erosions, scales and numerous excoriations on the face. A shows the state before application, and B shows the state after application of the CNP aqueous-solution preparation with a concentration of 100 µg/ml twice a day for 4 days. (Refer to Case 7 of CNP aqueous-solution preparation; subject 7; Tables 5 and 6)

As a result, 20 min after application, a the subjective symptom of burning sensation on the right side of the face subsided, and erythema began to be slightly improved. No irritation symptom attributable to the application of the CNP aqueous-solution preparation was observed at all. On the 4th day from the start of the application of the CNP aqueous-solution preparation, all of the infiltrative erythema, lichenified lesions, erythema, severe scales, adhesion of crusts and numerous excoriations on the face were markedly improved. By the application of the CNP aqueous-solution preparation of the present invention, the itching sensation level was improved from 10 to 0, the absence of subjective itching, based on the visual analogue scale method. In addition, the severity level of the rash on the face was improved from severe to mild by the application of the CNP aqueous-solution preparation, in accordance with the classification by the Dermatological Association Guideline. Subsequently, follow-up showed no recurrence of erythema even after discontinuation of the administration of the CNP aqueous-solution preparation. FIG. 3 is a photograph showing the application of the CNP aqueous-solution preparation of the present invention to the subject.

CNP Aqueous-Solution Preparation, Test Example 3 (Case 8; Subject 8; see Tables 5 and 6):
Treatment and its Outcome:

The subject of Case 8 presented with infiltrative erythema with itching associated with sleep disturbance, lichenified lesions, and erythema over the whole body; had severe infiltration and erythema due to recurrence of eczema with itching over the whole body, and was in a state in which exudate would come out if not treated by the application of "the strongest" steroid external drugs.

Under such conditions, we attempted to apply the CNP aqueous-solution preparation with a concentration of 100 µg/ml obtained in Example 3 to the erythema, infiltrative erythema and scales on the face and neck, the areas in which no therapeutic effect was observed with steroid external drugs. The number of application was twice a day.

Using the right/left comparative method, the CNP aqueous-solution preparation was first applied to the right side of the face and neck twice at 20 min interval, and saline alone was applied to the left side. As a result, infiltration and erythema began to be slightly improved on the right side. No irritation symptom attributable to the CNP aqueous-solution preparation was observed at all.

Subsequently, the CNP aqueous-solution preparation was applied to both sides of the face and neck twice a day. As a result, erythema and infiltration were improved and erosions were also reduced after 3 days. The application of the CNP aqueous-solution preparation reduced itching, and the itching sensation level was improved from 10 to 4 based on the visual analogue scale method. The severity level of the rash 3 days after the start of the application was improved from most severe to moderate by the standards of the Guideline 2005. Subsequent further continuous application of the CNP aqueous-solution preparation twice a day for 7 days further improved the rash, and moderate infiltrative erythema was improved to mild erythema.

CNP Aqueous-Solution Preparation, Test Example 4 (Case 3; Subject 9; see Tables 5 and 6):
Treatment and its Outcome:

The subject of Case 3 presented with infiltrative erythema, lichenified lesions, erythema, severe scales, adhesion of crusts, and numerous excoriations over the whole body, and the rash on the face was characterized mainly by erythema with lichenification, papules, erosions, scales, and numerous excoriations.

The CNP aqueous-solution preparation with a concentration of 100 µg/ml was applied to both sides of the face of the subject. As a result, the subjective symptom of sensation of tight-stretched skin was improved after 10 min. Then erythema was improved and the skin became soft to the touch with a finer texture from after 30 min. No irritation symptoms were observed with the external application, and the efficacy for epithelization of erosion and excoriation also became evident. Furthermore, findings about some beneficial changes such as reduction of scales and becoming finer skin texture were obtained. After 4 days from the application of the CNP aqueous-solution preparation of 100 µg/ml, all of the infiltrative erythema, lichenified lesions, erythema, severe scales, adhesion of crusts, and numerous excoriations were markedly improved. While the itching sensation level before application was rated as 10, subjective itching completely disappeared after the application to a level of 0.

Regarding the severity of erythema on the face after application of the CNP aqueous-solution preparation, there were a little inflammatory symptoms with almost no dryness, and the severity level of the rash based on the Dermatological Association Guideline was markedly improved from severe to minor.

From the above findings, the CNP aqueous-solution preparation was concluded to be very effective in this case. Subsequent follow-up showed no recurrence of erythema after discontinuation of the application of the present preparation.
CNP Aqueous-Solution Preparation, Test Example 5 (Case 4; Subject 10; see Tables 5 and 6):
Treatment and its Outcome:

This test mainly aimed at evaluation of absorbability of the CNP preparations of the present invention on the forearms, on which absorbability is presumed to be inferior to that on the face.

The subject of Case 4 presented with moderate erythema, scales and excoriation over the whole body, and the rash on the forearms was characterized mainly by erythema with severe swelling, scales, and excoriations.

Under such conditions, 100 µl of the CNP aqueous-solution preparation with a concentration of 100 µg/ml was applied to the right forearm 3 times at 20 min interval, and saline alone was applied to the left forearm. As a result, 60 min later, subjective itching was reduced on the right forearm to which the CNP aqueous-solution preparation was applied; and erythema was also markedly improved; and inflammation and dryness symptoms mostly disappeared as well. No irritation symptom associated with the application of the aqueous-solution preparation was observed at all. Thus, the CNP aqueous-solution preparation of the present invention exhibited remarkable effects on the forearms of the subject of this case as well. These findings indicated that the preparation of the present invention is also effective to the regions other than the face where the drug absorbability is presumed to be relatively high, namely the disorders on forearms. The rash on the forearms was improved by the administration of the CNP aqueous-solution preparation, from severe to minor level according to the classification based on the Dermatological Association Guideline. In addition, application of the CNP aqueous-solution preparation improved the itching sensation level from 10 to 1 based on the visual analogue scale method.

Next, CNP gel-base preparations were tested. "Gel-base preparation" differs from "gel preparation" in that the former does not comprise dipotassium glycyrrhizinate, allantoin, pyridoxine hydrochloride, xanthan gum and vitamin E. The effects of CNP preparations would be more clearly demonstrated to be due to the effects of CNP itself by confirming the effects of CNP in a preparation without these components, which could have some efficacy potentially.

EXAMPLE 7

1. Production of CNP Gel-Base Preparation:
Preparation of the gel was performed as follows.
0.1 g of methyl parahydroxybenzoate (product name: Mekkins M, Ueno Fine Chemicals Industry), 0.2 g of phenoxyethanol, and 3.0 g of 1,2-pentanediol were measured in the same container, dissolved at 60-70° C., and introduced into a mixing kettle. The, 6.0 g of concentrated glycerin was introduced and a mixture of 0.44 g of carboxy vinyl polymer (product name: Carbopol 940, Lubrisol Advanced Materials, Inc.) and 0.08 g of xanthan gum (product name: Keltrol T, CP Kelco) were added, and stirred with a paddle at 15 rpm to be sufficiently dispersed. Next, while stirring with a paddle at 15 rpm, 83.95 g of purified water was gradually introduced and the mixture was dissolved by stirring at a kettle temperature of 70-80° C., with a paddle at 20 rpm and a disperser at 1500-2000 rpm. After stopping the disperser, dissolution was confirmed and cooling was immediately started; when the kettle temperature approached around 40° C., 6.0 g of Lubrajel NP from ISP Japan, Ltd. (2.7 g of Glycerin, 0.06 g of carboxy vinyl polymer, 0.018 g of sodium polyacrylate, 3.222 g of water) was added and mixed homogeneously with a paddle at 20 rpm, then 0.230 g of potassium hydroxide was added for neutralization, and when the kettle temperature reached 25° C., the rotation of the paddle was terminated to obtain a gel-base.

Then, 3 mg of human CNP-22 (Peptide Institute, Inc.) as a principal agent was dissolved in 3 ml of saline to obtain the CNP solution with a concentration of 1000 µg/ml, and 1 ml of this CNP solution was homogeneously stirred and mixed in 19 g of the gel-base obtained as above, to produce the gel-base preparation with a concentration of 50 µg/g.

Similarly, 600 µl of the above CNP solution with a concentration of 1000 µg/ml was diluted with 400 µl of saline to prepare the concentration of 600 µg/ml, then the 1 ml of resulting solution was homogeneously stirred and mixed in 19 g of the gel-base obtained as above, to produce the gel-base preparation with a concentration of 30 µg/g.

EXAMPLE 8

2. Diagnosis of Subjects:

Prior to administration of the CNP gel-base preparation of the present invention, history taking from the subjects, scratch tests for allergens and a diagnosis were conducted. Table 7 (subjects 11-15) and Table 9 (subjects 16-20) show the results of the subjects' history taking and diagnosis, i.e., sex, age, onset and disease course, family history, past history, scratch test results, diagnostic findings, and symptom evaluations based on "Guideline 2005" of the subject in each case.

EXAMPLE 9

3. Therapeutic Effects on Subjects:

Therapeutic effects of the CNP gel-base preparation of the present invention are shown in Table 8 (subjects 11-15) and Table 10 (subjects 16-20). In Tables 8 and 10, "itching sensation" represents a comparison of the itching sensation evaluated using the visual analogue scale method before and after treatment. Similarly, "non-recurrence period" refers to the period after discontinuation of the treatment by the preparation of the present invention subsequent to the improvement of symptoms, in which relapse of the symptoms did not occur. In order to evaluate objectively, photographs were taken before and after application of CNP preparations for all cases. Of these, photographs of some cases are shown in the figures.

As shown in Tables 7 to 10, simply applying the CNP gel-base preparations of the present invention to affected areas of atopic dermatitis twice a day for 2-4 days, resulted in itching sensation to be mostly disappeared, and the severity levels of the rash in terms of external appearance was markedly improved in accordance with the Dermatological Association Guideline and with the SCORAD method.

The CNP gel-base preparations of the present invention are almost identically effective with both concentrations of 30 µg/g and 50 µg/g, and the preparations showed their efficacy regardless of sex over a broad range of ages from 21 to 39 years old. In addition, the preparations were effective for any regions including the face, neck and upper limbs. Furthermore, atopic dermatitis was improved in the patients who have immunoreactivity for a wide range of allergens, from patients with immunoreactivity to house dust and mites, to patients with immunoreactivity for all of house dust, mites, cedar, orchard grass, and ragweed.

The CNP gel-base preparations of the present invention markedly improved atopic dermatitis of patients with a familial allergic diathesis. In addition, the CNP gel-base preparations of the invention markedly improved the symptoms of atopic dermatitis in subjects 11-18, who had developed the disease in their infancy and had recurrence repeatedly. Additionally, the CNP gel-base preparations of the present invention markedly improved the symptoms of intractable, frequently-recurrent atopic dermatitis. Moreover, it is surprising that the CNP gel-base preparations of the present invention markedly improved symptoms of atopic dermatitis which steroid external therapy had failed to alleviate. Furthermore, it deserves a special note that the recurrence of atopic dermatitis was not observed for at least 5 days, and for longer cases 2 weeks or more, after discontinuation of the application of the CNP gel-base preparations of the invention.

Here, the above therapeutic effects on atopic dermatitis were more clearly demonstrated to be attributable to the efficacy of CNP itself since the CNP gel-base preparation of the present invention differs from "gel preparation" in that the former does not comprise dipotassium glycyrrhizinate, allantoin, pyridoxine hydrochloride, xanthan gum, and vitamin E.

TABLE 7

Diagnosis prior to application of CNP gel-base preparation.

| | Subject | | | | |
|---|---|---|---|---|---|
| | Subject 11 | Subject 12 | Subject 13 | Subject 14 | Subject 15 |
| Case | — | — | — | — | — |
| Sex | Male | Female | Female | Female | Male |
| Age | 31 years old | 23 years old | 39 years old | 39 years old | 21 years old |
| Onset and course of disease | Developed in infancy, having recurrent eczema with itching; infiltrative erythema on the face appeared since he started to work, and it has recurred frequently. | Developed in infancy, having recurrent eczema with itching; eczema also developed and frequently recurred on the face starting several years ago. | Developed on the face in infancy; since around 20 years of age, dry eczema extended to almost whole body including the face. The face in particular has repeatedly become red with fever as if it | Developed in infancy, having recurrent eczema with itching; in particular infiltrative erythema on the neck induces strong itching, and the region is always wrapped in bandages, with complication of | Developed at the age of 4, having recurrent eczema with itching; recently, erythema on the face and neck began to show intractable nature. |

TABLE 7-continued

Diagnosis prior to application of CNP gel-base preparation.

| | Subject 11 | Subject 12 | Subject 13 | Subject 14 | Subject 15 |
|---|---|---|---|---|---|
| | | | got burned, and has also been severely dry for many years. | intractable atopic alopecia. | |
| Family history | Child; Atopic dermatitis | Mother; Atopic dermatitis | Mother; Atopic dermatitis | Father; Atopic dermatitis | Mother and grandmother; Atopic dermatitis |
| Past history | | Allergic rhinitis | Allergic rhinitis, Bronchial asthma | Bronchial asthma | Allergic rhinitis |
| Scratch tests | House dust: 2+ Mite: 3+ Cedar: 2+ Orchard grass: 2+ Ragweed: 1+ | House dust: 2+ Mite: 3+ Cedar: 1+ Orchard grass: 3+ Ragweed: 1+ | House dust: 2+ Mite: 2+ Cedar: 1+ | House dust: 2+ Mite: 3+ Cedar: 2+ Orchard grass: 2+ Ragweed: 1+ | House dust: 2+ Mite: 3+ Cedar: 2+ Orchard grass: 1+ |
| Diagnostic findings | Erythema with severe swelling/ edema/ infiltration/ lichenification, as well as many papules, severe scales, adhesion of crusts, vesicles, and erosions are observed on the face. | Up to moderate erythema, scales, a small number of papules, and excoriations are observed on the face. | Infiltrative erythema, lichenified lesions, erythema are observed on the face, neck and back, accompanied by strong itching with sleep disturbance.. | Erythema with lichenification, severe scales, adhesion of crusts, and erosions are observed on the face, neck, four limbs and body trunk. | Infiltrative erythema, erythema, scales, and lichenification are observed on the face and neck. |
| Symptoms of application regions | Rash on the face are associated with erythema with severe swelling/edema/ infiltration/ or lichenification, adhesion of crusts and vesicles. | Rash on the face is mainly characterized by erythema, edema, papules, erosions, and excoriations. | Rash on the face is mainly characterized by erythema with lichenification, and scales. | Rash on the face and neck are associated with erythema with infiltration or lichenification, as well as severe scales, and adhesion of crusts. | Rash on the face and neck is erythema with lichenification/ infiltration. |
| Effects of steroid external drug | Relapsed on discontinuation of steroid external therapy | No improvement even by "very strong" steroid external therapy. | Relapsed on discontinuation of steroid external therapy; in particular intractable nature is shown on the face. | Relapsed on discontinuation of steroid external therapy. | Relapsed on discontinuation of steroid external therapy. |
| Evaluation of symptoms | Severe | Moderate | Severe | Severe | Severe |

TABLE 8

Therapeutic effects of CNP gel-base preparation.

| | Subject 11 | Subject 12 | Subject 13 | Subject 14 | Subject 15 |
|---|---|---|---|---|---|
| Case | — | — | — | — | — |
| Sex | Male | Female | Female | Female | Male |
| Age | 31 years old | 23 years old | 39 years old | 39 years old | 21 years old |
| Dosage form | CNP gel-base preparation | CNP gel-base preparation | CNP gel-base preparation | CNP gel-base preparation | CNP gel-base preparation |
| Dosage | 30 μg/g | 30 μg/g | 30 μg/g | 30 μg/g | 30 μg/g |
| Number of administration | Twice a day | Twice a day | Twice a day | Twice a day | Twice a day |
| Days of administration | 3 days | 3 days | 3 days | 3 days | 3 days |
| Applied region | Face | Face | Face | Face and neck | Face and neck |

TABLE 8-continued

Therapeutic effects of CNP gel-base preparation.

| | Subject | | | | |
|---|---|---|---|---|---|
| | Subject 11 | Subject 12 | Subject 13 | Subject 14 | Subject 15 |
| Severity level of rash by Dermatological Association Guideline | Before: severe<br>After: mild | Before: severe<br>After: minor | Before: severe<br>After: mild | Before: severe<br>After: mild | Before: severe<br>After: mild |
| Severity level evaluation of the rash region by SCORAD (before application) | Erythema: 3<br>Edema/papulation: 3<br>Oozing/crusting: 2<br>Excoriation: 1<br>Lichenification: 2<br>Dryness: 2<br>Total: 13/18 | Erythema: 3<br>Edema/papulation: 2<br>Oozing/crusting: 2<br>Excoriation: 2<br>Lichenification: 1<br>Dryness: 2<br>Total: 12/18 | Erythema: 3<br>Edema/papulation: 2<br>Oozing/crusting: 1<br>Excoriation: 1<br>Lichenification: 3<br>Dryness: 3<br>Total: 13/18 | Erythema: 2<br>Edema/papulation: 2<br>Oozing/crusting: 2<br>Excoriation: 2<br>Lichenification: 2<br>Dryness: 3<br>Total: 13/18 | Erythema: 2<br>Edema/papulation: 2<br>Oozing/crusting: 1<br>Excoriation: 1<br>Lichenification: 2<br>Dryness: 2<br>Total: 10/18 |
| Severity level evaluation of the rash region by SCORAD (after application) | Erythema: 1<br>Edema/papulation: 0<br>Oozing/crusting: 1<br>Excoriation: 0<br>Lichenification: 0<br>Dryness: 1<br>Total: 3/18 | Erythema: 0<br>Edema/papulation: 0<br>Oozing/crusting: 0<br>Excoriation: 1<br>Lichenification: 0<br>Dryness: 1<br>Total: 2/18 | Erythema: 1<br>Edema/papulation: 0<br>Oozing/crusting: 0<br>Excoriation: 0<br>Lichenification: 0<br>Dryness: 1<br>Total: 2/18 | Erythema: 1<br>Edema/papulation: 0<br>Oozing/crusting: 1<br>Excoriation: 1<br>Lichenification: 0<br>Dryness: 1<br>Total: 4/18 | Erythema: 1<br>Edema/papulation: 0<br>Oozing/crusting: 0<br>Excoriation: 0<br>Lichenification: 0<br>Dryness: 1<br>Total: 2/18 |
| Detailed description of improvement status of symptoms | After 3 days of application of 30-µg/g CNP gel-base preparation to the face twice a day, erythema, infiltration and itching markedly improved and the skin textures became fine. | After 3 days of application of 30 µg/g CNP gel-base preparation to the face twice a day, erythema, infiltration, scales and itching were markedly improved. | By the application of 30 µg/g CNP gel-base preparation to the face twice a day, after 2 days erythema was reduced, and infiltration and itching were markedly improved, and burning sensation disappeared on day 3. | After 3 days of application of 30-µg/g CNP gel-base preparation to the face twice a day, erythema, infiltration, scales and itching were markedly improved. | After 3 days of application of 30-µg/g CNP gel-base preparation to the face and neck twice a day, erythema, infiltration, and itching were markedly improved. |
| Itching sensation | Before: 10<br>After: 0 | Before: 10<br>After: 0 | Before: 10<br>After: 1 | Before: 10<br>After: 0 | Before: 10<br>After: 0 |
| Non-recurrence period | 2 weeks | 2 weeks | 2 weeks or more | 5 days | 2 weeks |

TABLE 9

Diagnosis prior to application of CNP gel-base preparation.

Figure 4:
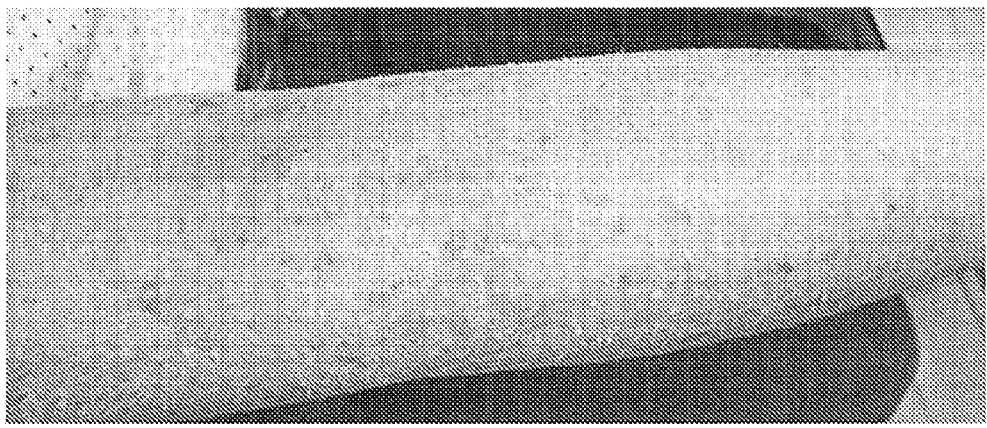
FIG. 4 is a photograph showing the effects of a CNP gel-base preparation of the present invention when it was applied to the arm of a patient who presented with erythema associated with lichenification, infiltrative erythema, severe scales, adhesion of crusts, vesicles, and erosions throughout the whole body. A shows the state before application, and B shows the state after application of the CNP gel-base preparation with a concentration of 30 µg/g, twice a day for 2 days. (Refer to CNP gel-base preparation; subject 17; Tables 9 and 10)
Figure 4:
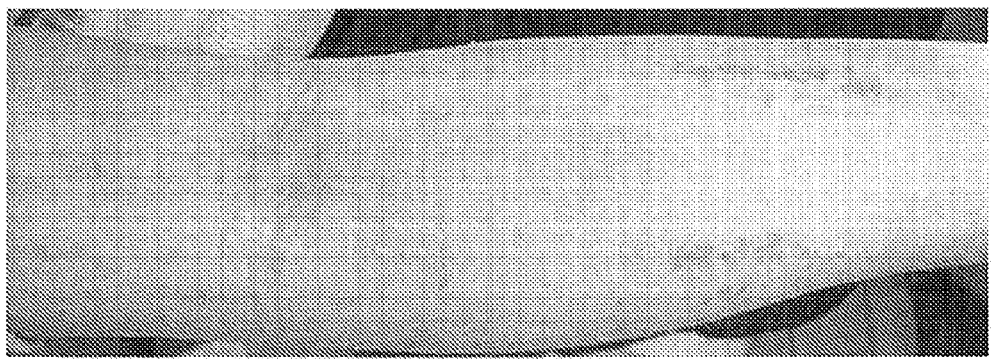
Figure 5:
FIG. 5 is a photograph showing the effects of a CNP gel-base preparation of the present invention when it was applied to a patient who presented with a rash associated with severe swelling/edema/infiltration/erythema on the upper limbs. A shows the state before application, and B shows the state after application of the CNP gel-base preparation with a concentration of 50 µg/g, twice a day for 4 days. (Refer to CNP gel-base preparation; subject 20; Tables 9 and 10)

| | Subject | | | | |
|---|---|---|---|---|---|
| | Subject 16 | Subject 17 (FIG. 4) | Subject 18 | Subject 19 | Subject 20 (FIG. 5) |
| Case | — | — | — | — | — |
| Sex | Male | Female | Male | Female | Female |
| Age | 25 years old | 36 years old | 22 years old | 31 years old | 35 years old |
| Onset and course of disease | Had recurrent eczema with itching since infancy, and symptoms worsened due to psychological stress during these last several years; by the application of steroid external drugs every day, skin flush, scales and infiltrative erythema became observed over the whole body. | Developed in infancy, and symptoms worsen due to change of seasons and sweating. Application of various external preparations did not stop the inflammation at all, and sleep disturbance due to itching continued; severe swelling prohibits bending of the arms. | Developed in infancy; symptoms were initially only on the body trunk, but rapidly worsened to extend to almost the whole body including the face. In particular, symptoms worsen when he is in dusty conditions. | She had eczema at cubital fossae and popliteal fossae that worsened by sweating, and which was reduced temporarily by steroid external application but relapsed repeatedly. Since around 2002 when she started to work, erythema appeared on the face due to leisureless life | Recurrent erythema appeared since 21 years of age when she began to work a night shift, and extended to the whole body. |

TABLE 9-continued

Diagnosis prior to application of CNP gel-base preparation.

| | Subject 16 | Subject 17 (FIG. 4) | Subject 18 | Subject 19 | Subject 20 (FIG. 5) |
|---|---|---|---|---|---|
| | | | | and stress caused by interpersonal relationships. | |
| Family history | Father; Atopic dermatitis | Father; Allergic rhinitis, conjunctivitis | Mother; Atopic dermatitis | Mother; Bronchial asthma | Elder brother; Bronchial asthma |
| Past history | Allergic rhinitis | Allergic rhinitis | Allergic rhinitis, Bronchial asthma | Allergic rhinitis, Conjunctivitis | Allergic rhinitis, Conjunctivitis |
| Scratch test | House dust: 3+ Mite: 3+ Cedar: 2+ Orchard grass: 3+ Ragweed: 1+ | House dust: 2+ Mite: 3+ Cedar: 2+ | House dust: 2+ Mite: 3+ | House dust: 3+ Mite: 3+ Cedar: 3+ Orchard grass: 1+ Ragweed: 2+ | House dust: 3+ Mite: 3+ Cedar: 2+ |
| Diagnostic findings | Infiltrative erythema, lichenified lesions, erythema, severe scales, adhesion of crusts, and numerous excoriations are observed over the whole body. He is in a state of erythroderma posteczematosa. | Erythema with lichenification, infiltrative erythema, severe scales, adhesion of crusts, vesicles, and erosions are observed over the whole body. | Infiltrative erythema with strong itching associated with sleep disturbance, erythema, and excoriations are observed on almost whole body including face and neck. | Infiltrative erythema, lichenified lesions, erythema, and numerous excoriations are observed over the whole body. Have strong itching associated with sleep disturbance. | Infiltrative erythema, lichenified lesions, erythema, severe scales, adhesion of crusts and numerous excoriations are observed over the whole body. |
| Symptoms of application regions | Rash on the face and neck includes erythema with severe swelling/ infiltration/ or lichenification. | Rash on the face, neck and four limbs are associated with erythema with infiltration or lichenification, severe scales, and numerous excoriations. | Rash on the face is mainly characterized by erythema with lichenification, erosions, scales, and numerous excoriations. | Rash on the face and neck consists of severe swelling/ edema/ infiltration/ erythema, vesicles and erosions. | Rash on the upper limbs are associated with severe swelling/ edema/ infiltration/ erythema. |
| Effects of steroid external drug | Skin flush and desquamation appear over the whole body after discontinuation of steroid external application, resulting in a state of erythroderma. | Symptoms are not alleviated by steroid external therapy at all. | Recurrence occurred soon after discontinuation of steroid external therapy. | Skin flush and desquamation appear after discontinuation of steroid external application. | Skin flush and desquamation appear after discontinuation of steroid external application. |
| Evaluation of symptoms | Most severe | Most severe | Most severe | Severe | Most severe |

TABLE 10

Therapeutic effects of CNP gel-base preparation.

| | Subject 16 | Subject 17 (FIG. 4) | Subject 18 | Subject 19 | Subject 20 (FIG. 5) |
|---|---|---|---|---|---|
| Case | — | — | — | — | — |
| Sex | Male | Female | Male | Female | Female |
| Age | 25 years old | 36 years old | 22 years old | 31 years old | 35 years old |
| Dosage form | CNP gel-base preparation | CNP gel-base preparation | CNP gel-base preparation | CNP gel-base preparation | CNP gel-base preparation |
| Dosage | 30 μg/g | 30 μg/g | 50 μg/g | 50 μg/g | 50 μg/g |
| Number of administration | Twice a day | Twice a day | Twice a day | Twice a day | Twice a day |

TABLE 10-continued

Therapeutic effects of CNP gel-base preparation.

| | Subject | | | | |
|---|---|---|---|---|---|
| | Subject 16 | Subject 17 (FIG. 4) | Subject 18 | Subject 19 | Subject 20 (FIG. 5) |
| Days of administration | 3 days | 2 days | 3 days | 2 days | 4 days |
| Applied region | Face and neck | Face, neck and upper limbs | Face | Face and neck | Forearms |
| Severity level of rash by Dermatological Association Guideline | Before: severe After: mild | Before: severe After: mild-moderate | Before: severe After: mild | Before: severe After: mild | Before: severe After: minor |
| Severity level evaluation of the rash region by SCORAD (before application) | Erythema: 3 Edema/papulation: 3 Oozing/crusting: 3 Excoriation: 2 Lichenification: 3 Dryness: 3 Total: 17/18 | Erythema: 3 Edema/papulation: 2 Oozing/crusting: 3 Excoriation: 3 Lichenification: 3 Dryness: 3 Total: 17/18 | Erythema: 3 Edema/papulation: 2 Oozing/crusting: 2 Excoriation: 1 Lichenification: 3 Dryness: 3 Total: 14/18 | Erythema: 3 Edema/papulation: 3 Oozing/crusting: 3 Excoriation: 2 Lichenification: 2 Dryness: 3 Total: 16/18 | Erythema: 3 Edema/papulation: 3 Oozing/crusting: 1 Excoriation: 1 Lichenification: 1 Dryness: 3 Total: 12/18 |
| Severity level evaluation of the rash region by SCORAD (after application) | Erythema: 1 Edema/papulation: 1 Oozing/crusting: 0 Excoriation: 1 Lichenification: 1 Dryness: 1 Total: 5/18 | Erythema: 1 Edema/papulation: 1 Oozing/crusting: 1 Excoriation: 2 Lichenification: 1 Dryness: 1 Total: 7/18 | Erythema: 1 Edema/papulation: 1 Oozing/crusting: 1 Excoriation: 1 Lichenification: 1 Dryness: 2 Total: 7/18 | Erythema: 1 Edema/papulation: 1 Oozing/crusting: 1 Excoriation: 0 Lichenification: 0 Dryness: 1 Total: 4/18 | Erythema: 0 Edema/papulation: 0 Oozing/crusting: 0 Excoriation: 0 Lichenification: 0 Dryness: 1 Total: 1/18 |
| Detailed description of improvement status of symptoms | After 2 or 3 days of application of 30 μg/g CNP gel-base preparation to the face and neck twice a day, tingling sensation disappeared, and erythema, infiltration and itching were markedly improved. | After 2 days of application of 30 μg/g CNP gel-base preparation to the face, neck and upper limbs twice a day, erythema, infiltration, scales and itching were markedly improved, and she was able to sleep. | After application of 50 μg/g CNP gel-base preparation twice a day, dryness and itching were markedly improved on the next day. 2 days later, erythema was reduced, and only slight scales remained on the 3rd day. | After 2 days of application of 50 μg/g CNP gel-base preparation to the face and neck twice a day, erythema was reduced, and itching disappeared. Slight dryness and erythema remained. | After 3 days of application of 50 μg/g CNP gel-base preparation twice a day, erythema was markedly reduced, and the skin texture became fine on the 4th day. |
| Itching sensation | Before: 10 After: 2 | Before: 10 After: 2 | Before: 10 After: 3 | Before: 10 After: 0 | Before: 10 After: 0 |
| Non-recurrence period | 7 days | 5 days | 5 days | 5 days | 7 days |

EXAMPLE 10

1. Production of CNP Ointment Preparation:

Ointments were prepared as follows: 3 mg of human CNP-22 (Peptide Institute, Inc.) as a principal agent was dissolved in 3 ml of saline to obtain the CNP solution with a concentration of 1000 μg/ml; 1 ml of this CNP solution was homogeneously mixed in 9 g of white vaseline of Japanese Pharmacopoeia by high-speed stirring, to adjust its concentration to 100 μg/g.

Similarly, 500 μl of the above CNP solution with a concentration of 1000 μg/ml was diluted with 500 μl of saline to adjust its concentration at 500 μg/ml, and 1 ml of this solution was homogeneously mixed in 9 g of white vaseline of the Japanese Pharmacopoeia by high-speed stirring, to adjust its concentration at 50 μg/g.

In addition, 300 μl of the above CNP solution with a concentration of 1000 μg/ml was diluted with 700 μl of saline to adjust its the concentration at 300 μg/ml, and 1 ml of this solution was homogeneously mixed in 9 g of white vaseline of the Japanese Pharmacopoeia by high-speed stirring, to adjust its concentration to 30 μg/g.

EXAMPLE 11

2. Diagnosis of Subjects:

Prior to administration of the CNP ointment preparation of the present invention, history taking from subjects, scratch tests for allergens and diagnosis were conducted. Table 11 (subjects 21-25), Table 13 (subjects 26-30), and Table 15 (subjects 31-35) show the results of the subjects' history taking and diagnosis, i.e., sex, age, onset and course of disease, family history, past history, scratch test results, diagnostic findings, and symptom evaluation based on "Guideline 2005" of the subject in each case.

EXAMPLE 12

3. Therapeutic Effect on Subjects:

Therapeutic effects of the CNP ointment preparation of the present invention are shown in Table 12 (subjects 21-25), Table 14 (subjects 26-30), and Table 16 (subjects 31-35). In Tables 12, 14 and 16, "itching sensation" represents a comparison of the itching sensation evaluated using the visual analogue scale method before and after treatment. Similarly, the "non-recurrence period" refers to the period after discontinuation of the treatment by the preparation of the present invention subsequent to the improvement of symptoms, for which relapse of the symptoms did not occur.

As shown in Tables 11 through 16, simply applying the CNP ointment preparation of the present invention to affected areas of atopic dermatitis twice a day for 2-3 days resulted in the itching sensation to disappear mostly, and the severity levels of the rash in terms of external appearance was markedly improved in accordance with the Dermatological Association Guideline or in terms of external appearance according to the SCORAD method. Here, in order to evaluate objectively, photographs were taken before and after the application of CNP preparations for all cases. Of these, photographs of some of the cases are shown in the figures.

The CNP ointment preparations of the present invention are almost identically effective with concentrations of 30 μg/g, 50 μg/g, and 100 μg/g, and the preparations showed their efficacy regardless of sex over a broad range of ages from 3 to 56 years old. In addition, the preparations were effective for any regions including the face, neck, back, and upper limbs. Furthermore, atopic dermatitis was improved in the patients who have immunoreactivity for a wide range of allergens, from patients with immunoreactivity to house dust, mites, and orchard grass to patients with immunoreactivity to all of house dust, mites, cedar, orchard grass, and ragweed.

The CNP ointment preparations of the present invention markedly improved atopic dermatitis of the patients with a familial allergic diathesis. In addition, the CNP ointment preparations of the present invention markedly improved symptoms of atopic dermatitis in the subjects who had developed the disease in their infancy and had recurrence repeatedly. Additionally, the CNP ointment preparations of the present invention also markedly improved symptoms of intractable, frequently-recurrent atopic dermatitis. Moreover, it is surprising that the CNP ointment preparations of the present invention markedly improved symptoms of atopic dermatitis steroid external therapy had failed to alleviate. Furthermore, it deserves special note that recurrence of atopic dermatitis was not observed for at least 5 days, and for longer cases, 2 weeks or more, after discontinuation of the application of the CNP ointment preparations of the present invention.

Here, since the CNP ointment preparations of the present invention do not comprise any components, other than CNP, which could potentially have some efficacy, the above therapeutic effects on atopic dermatitis are clearly demonstrated to be the efficacy of the CNP itself.

TABLE 11

Diagnosis prior to application of CNP ointment preparation.

Figure 6:
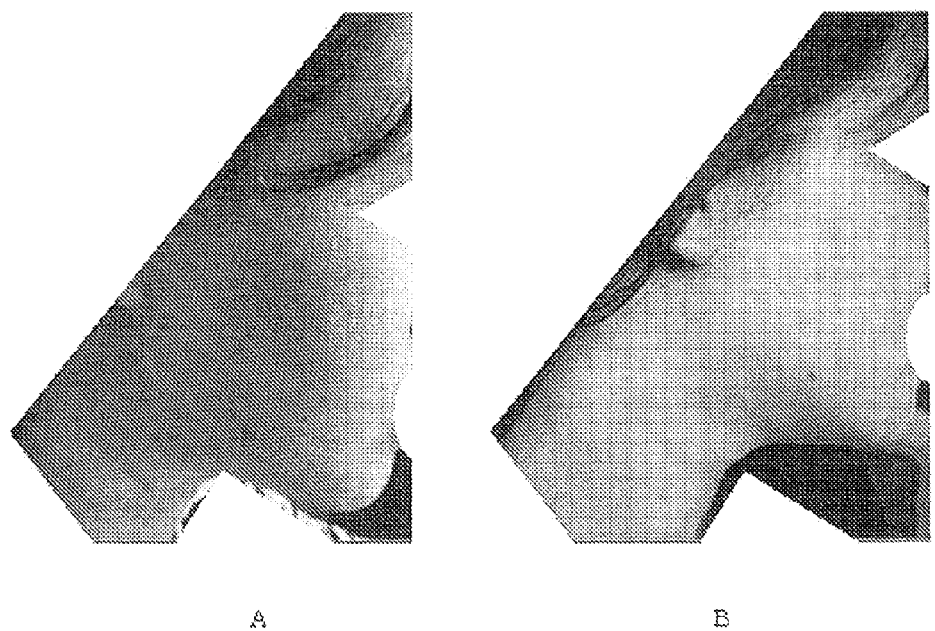
FIG. 6 is a photograph showing the effects of a CNP ointment preparation of the present invention, when it was applied to the face and neck of a patient who presented with infiltrative erythema, erythema, severe scales, adhesion of crusts, and numerous excoriations over the whole body, and particularly apparent on the face and neck. A shows the state before application, and B shows the state after application of the CNP ointment preparation with a concentration of 30 µg/g twice a day for 2 days. (Refer to CNP ointment preparation; subject 21; Tables 11 and 12)
Figure 7:
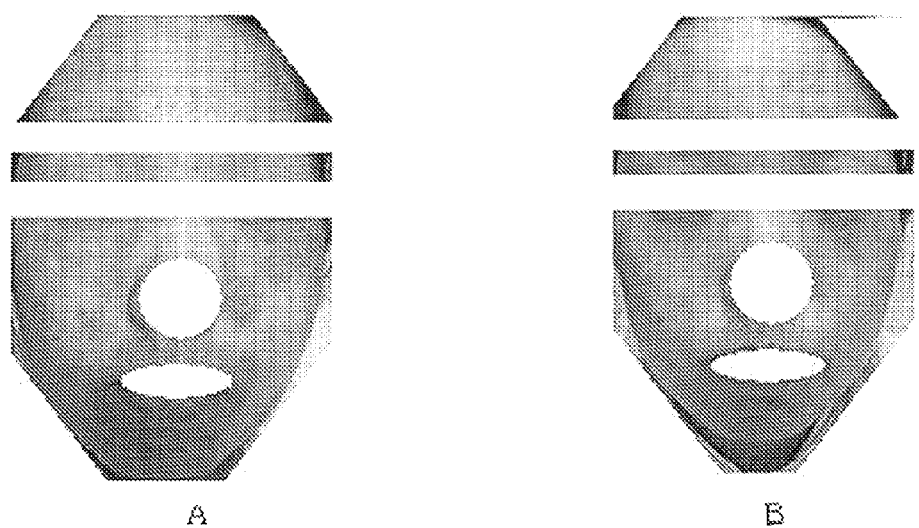
FIG. 7 is a photograph showing the effects of a CNP ointment preparation of the present invention when it was applied to the face of a patient who presented with infiltrative erythema with strong itching associated with sleep disturbance, erythema, excoriations on the face, neck, four limbs, and back, and had a rash mainly characterized by severe infiltrative erythema, scales, and numerous excoriations particularly on the face. A shows the state before application, and B shows the state after application of the CNP ointment preparation with a concentration of 50 µg/g, twice a day for 3 days. (Refer to CNP ointment preparation; subject 23; Tables 11 and 12)

| | Subject | | | | |
|---|---|---|---|---|---|
| | Subject 21 (FIG. 6) | Subject 22 | Subject 23 (FIG. 7) | Subject 24 | Subject 25 |
| Case | — | — | — | — | — |
| Sex | Female | Male | Female | Female | Male |
| Age | 21 years old | 21 years old | 28 years old | 33 years old | 39 years old |
| Onset and course of disease | Developed in infancy; symptoms worsen in dry seasons, erythema with itching appears mainly on the face, neck, upper limbs and body trunk, and the symptoms recurred repeatedly despite the application of steroid external drugs. | Developed at 3 months of age with eczema mainly on the four limbs; asthma worsened 4 years ago, and dermatitis rapidly expanded due to the stress of examinations and family relationships starting 3 years ago. | Developed at the time of being a junior high school student with symptoms on the face; eczema with itching which worsens with sweating have appeared repeatedly on the cubital fossae and back, etc.; since 3 years ago, erythema has always appeared despite steroid external application. | Developed in infancy, has recurrent eczema with itching; from around starting to work, infiltrative erythema appeared particularly on the face and neck, which extended to the whole body and she claims that she can hardly sleep because of itching. | Eczema appeared on the face since around 17 years of age, and he repeatedly suffers from dry dermatitis that worsens in winter. Thereafter he has continuously visited a dermatologist for treatment, but symptoms show intractable nature even against long-term steroid external therapy. |
| Family history | Mother; Atopic dermatitis | Younger sister, Father; Atopic dermatitis Mother: allergic rhinitis | Elder brother; Atopic dermatitis, Allergic rhinitis | Mother and younger brother; Atopic dermatitis | Child; Atopic dermatitis |
| Past history | Allergic rhinitis, Atopic conjunctivitis | Bronchial asthma | Allergic rhinitis, Bronchial asthma | Allergic rhinitis, Conjunctivitis | Bronchial asthma, Allergic rhinitis |
| Scratch test | House dust: 1+ Mite: 1+ Cedar: 2+ Orchard grass: 2+ | House dust: 2+ Mite: 3+ Cedar: 2+ Orchard grass: 2+ Ragweed: 2+ | House dust: 2+ Mite: 2+ Cedar: 2+ Orchard grass: 3+ Ragweed: 2+ | House dust: 2+ Mite: 2+ Cedar: 1+ Orchard grass: 1+ Ragweed: 1+ | House dust: 3+ Mite: 3+ Cedar: 2+ Orchard grass: 2+ |
| Diagnostic findings | Infiltrative erythema, erythema, severe scales, adhesion | Infiltrative erythema, erythema, severe scales, adhesion | Infiltrative erythema with strong itching associated with | Infiltrative erythema with strong itching and erythema are | Infiltrative erythema with strong itching associated with |

TABLE 11-continued

Diagnosis prior to application of CNP ointment preparation.

| | Subject 21 (FIG. 6) | Subject 22 | Subject 23 (FIG. 7) | Subject 24 | Subject 25 |
|---|---|---|---|---|---|
| | of crusts, and numerous excoriations are observed over the whole body, and particularly severe on the face and neck. | of crusts, and edema are observed on almost whole body, accompanied by hair loss. | sleep disturbance, erythema, and excoriations are observed on the face, neck, four limbs and back. | observed on the face, neck and body trunk. | sleep disturbance, lichenified lesions, and erythema are observed over the whole body. |
| Symptoms of application regions | Rash on the face and neck is mainly characterized by erythema with infiltration, scales and crusts. | Rash on the face and neck is mainly characterized by erythema with infiltration and lichenification. | Rash on the face and neck is mainly characterized by severe infiltrative erythema, scales and numerous excoriations. | Rash on the face and neck is mainly characterized by erythema with severe infiltration. | Rash on the face and neck is mainly characterized by erythema with infiltration and lichenification. |
| Effects of steroid external drug | Since recurrence soon observed by discontinuation of steroid external therapy, non-steroid external preparations were applied, leading to further exacerbation. | Out of control with steroid external therapy. | Sufficient effects are not obtained with steroid external drugs for erythema and infiltrative erythema on the face. | Recurrence occurred soon after discontinuation of steroid external therapy. | Sufficient effects are not obtained with steroid external drugs for lichenified lesions and infiltrative erythema. |
| Evaluation of symptoms | Severe | Most severe | Severe | Severe | Severe |

TABLE 12

Therapeutic effects of CNP ointment preparation

| | Subject 21 (FIG. 6) | Subject 22 | Subject 23 (FIG. 7) | Subject 24 | Subject 25 |
|---|---|---|---|---|---|
| Case | — | — | — | — | — |
| Sex | Female | Male | Female | Female | Male |
| Age | 21 years old | 21 years old | 28 years old | 33 years old | 39 years old |
| Dosage form | CNP ointment preparation | CNP ointment preparation | CNP ointment preparation | CNP ointment preparation | CNP ointment preparation |
| Dosage | 30 µg/g | 50 µg/g | 50 µg/g | 50 µg/g | 50 µg/g |
| Number of administration | Twice a day | Twice a day | Twice a day | Twice a day | Twice a day |
| Days of administration | 2 days | 2 days | 3 days | 2 days | 3 days |
| Applied region | Face and neck | Face and neck | Face and neck | Face and neck | Face and neck |
| Severity level of rash by Dermatological Association Guideline | Before: severe After: mild | Before: severe After: mild | Before: severe After: mild | Before: severe After: mild | Before: severe After: mild |
| Severity level evaluation of the rash region by SCORAD (before application) | Erythema: 3 Edema/papulation: 2 Oozing/crusting: 3 Excoriation: 2 Lichenification: 2 Dryness: 3 Total: 15/18 | Erythema: 3 Edema/papulation: 1 Oozing/crusting: 2 Excoriation: 1 Lichenification: 2 Dryness: 3 Total: 12/18 | Erythema: 3 Edema/papulation: 2 Oozing/crusting: 3 Excoriation: 2 Lichenification: 2 Dryness: 3 Total: 15/18 | Erythema: 3 Edema/papulation: 2 Oozing/crusting: 2 Excoriation: 1 Lichenification: 2 Dryness: 2 Total: 12/18 | Erythema: 2 Edema/papulation: 1 Oozing/crusting: 1 Excoriation: 1 Lichenification: 2 Dryness: 3 Total: 10/18 |
| Severity level evaluation of the rash region by | Erythema: 1 Edema/papulation: 1 Oozing/crusting: 1 Excoriation: 1 | Erythema: 1 Edema/papulation: 0 Oozing/crusting: 1 Excoriation: 1 | Erythema: 1 Edema/papulation: 1 Oozing/crusting: 1 Excoriation: 0 | Erythema: 1 Edema/papulation: 1 Oozing/crusting: 0 Excoriation: 0 | Erythema: 1 Edema/papulation: 0 Oozing/crusting: 0 Excoriation: 0 |

TABLE 12-continued

Therapeutic effects of CNP ointment preparation

| | Subject | | | | |
|---|---|---|---|---|---|
| | Subject 21 (FIG. 6) | Subject 22 | Subject 23 (FIG. 7) | Subject 24 | Subject 25 |
| SCORAD (after application) | Lichenification: 1 Dryness: 1 Total: 6/18 | Lichenification: 1 Dryness: 1 Total: 5/18 | Lichenification: 1 Dryness: 1 Total: 5/18 | Lichenification: 1 Dryness: 1 Total: 4/18 | Lichenification: 1 Dryness: 1 Total: 3/18 |
| Detailed description of improvement status of symptoms | After 2 days of application of 30-µg/g CNP ointment preparation to the face twice a day, erythema, infiltration, scales and itching were markedly improved. | After 2 days of application to the face and neck twice a day, erythema, infiltration, and itching were markedly improved. | After 3 days of application to the face and neck twice a day, erythema, excoriations, infiltration, and itching were markedly improved. | After 2 days of application to the face and neck twice a day, erythema, infiltration, and itching were markedly improved. | After 3 days of application to the face and neck twice a day, erythema, infiltration, and itching were markedly improved. |
| Itching sensation | Before: 10 After: 0 | Before: 10 After: 1 | Before: 10 After: 0 | Before: 10 After: 0 | Before: 10 After: 0 |
| Non-recurrence period | 5 days | 7 days | 7 days | 10 days | 2 weeks |

TABLE 13

Diagnosis prior to application of CNP ointment preparation.

Figure 8:
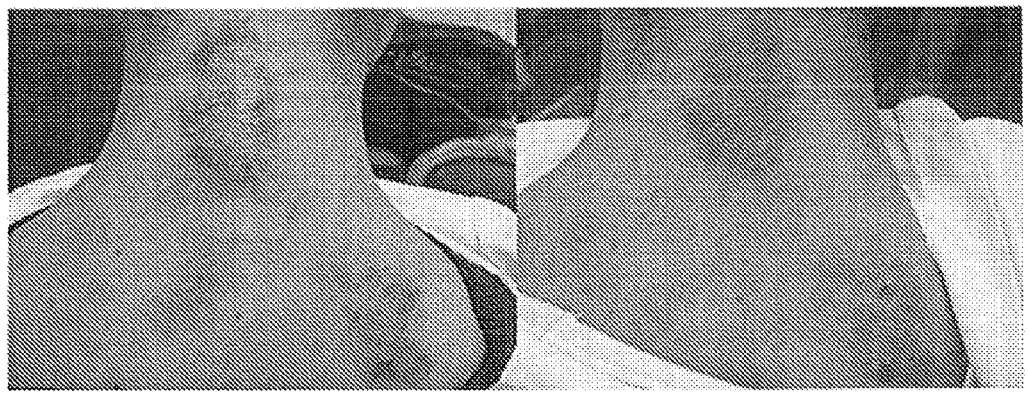
FIG. 8 is a photograph showing the effects of a CNP ointment preparation of the present invention, when it was applied to the neck and back of a patient who presented with infiltrative erythema, lichenified lesions, erythema, adhesion of crusts, and numerous excoriations on the body trunk, and had a rash forming a plaque associated with erythema with severe infiltration/lichenification, severe scales, and adhesion of crusts on the back. A shows the state before application, and B shows the state after application of the CNP ointment preparation with a concentration of 50 μg/g twice a day for 3 days. (Refer to CNP ointment preparation; subject 29; Tables 13 and 14)
Figure 9:
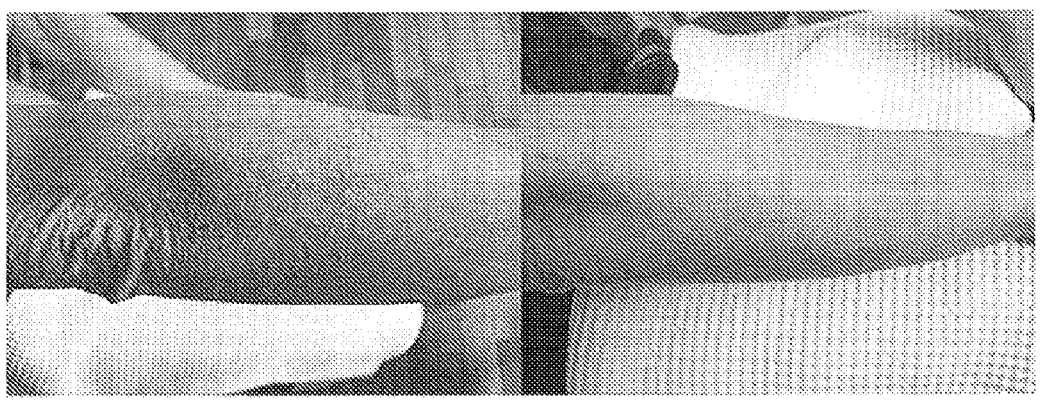
FIG. 9 is a photograph showing the effects of a CNP ointment preparation of the present invention, when it was applied to the upper limb of a patient suffering from the condition of erythroderma posteczematosa who presented infiltrative erythema, lichenified lesions, erythema, severe scales, adhesion of crusts, numerous excoriations over the whole body, and who had a rash mainly characterized by erythema associated with severe swelling and infiltration on the upper limbs. A shows the state before application, and B shows the state after application of the CNP ointment preparation with a concentration of 50 μg/g, twice a day for 2 days. (Refer to CNP ointment preparation; subject 30; Tables 13 and 14)
Figure 10:
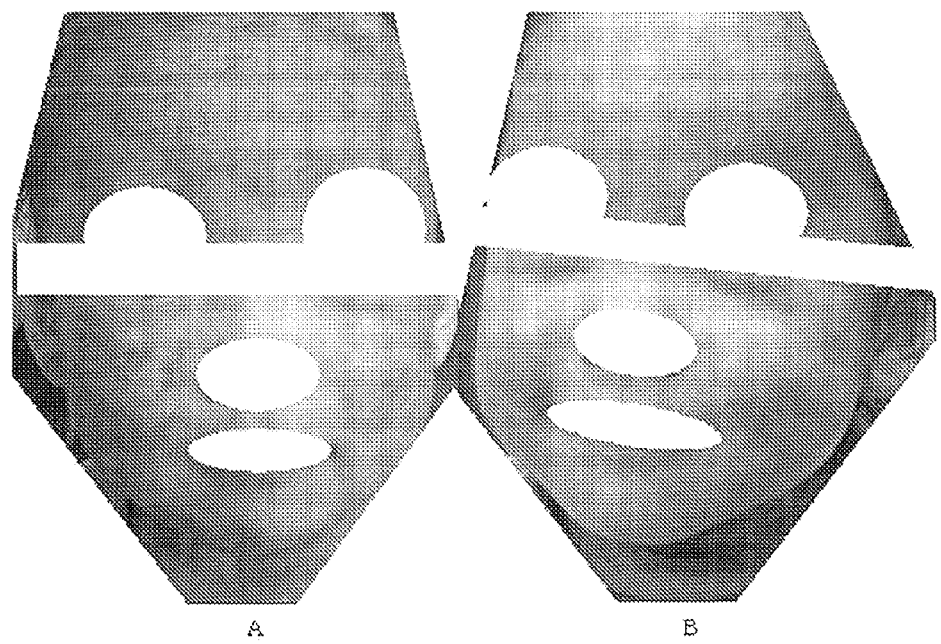
FIG. 10 is a photograph showing the effects of a CNP ointment preparation of the present invention when it was applied to the face of a patient who presented a rash consisting of infiltration/severe scales, adhesion of crusts, erosions and numerous excoriations on the face, and also infiltrative erythema, lichenified lesions, erythema, severe scales, adhesion of crusts, and numerous excoriations over the whole body. A shows the state before application, and B shows the state after application of the CNP ointment preparation with a concentration of 50 μg/g twice a day for 3 days. (Refer to CNP ointment preparation; subject 27; Tables 13 and 14)
Figure 11:
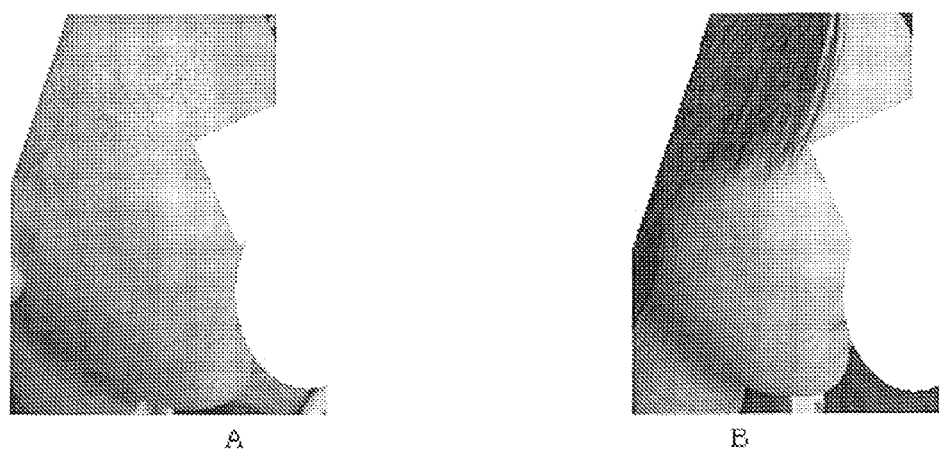
FIG. 11 is a photograph showing the effects of a CNP ointment preparation of the present invention when it was applied to the face of a patient suffering from the condition of erythroderma posteczematosa who presented a rash mainly characterized by infiltrative erythema with swelling and erosions on the face and neck, and infiltrative erythema, lichenified lesions, erythema, severe scales, and adhesion of crusts throughout the whole body. A shows the state before application, and B shows the state after application of the CNP ointment preparation with a concentration of 50 μg/g twice a day for 3 days. (Refer to CNP ointment preparation; subject 28; Tables 13 and 14)

| | Subject | | | | |
|---|---|---|---|---|---|
| | Subject 26 | Subject 27 (FIG. 10) | Subject 28 (FIG. 11) | Subject 29 (FIG. 8) | Subject 30 (FIG. 9) |
| Case | — | — | — | — | — |
| Sex | Female | Female | Female | Male | Male |
| Age | 32 years old | 3 years old | 22 years old | 44 years old | 36 years old |
| Onset and course of disease | Erythema began to appear on the face at the age of 20; erythema and papules appeared on the back and four limbs, which worsened by sweating; they have recurred repeatedly. | Developed at 2 months of age, having erythema over the whole body. In particular, the face is sometimes full of excoriations due to scratching all the time. | Developed in infancy, having recurrent eczema with itching; due to steroid external application every day, skin flush, scales, and infiltrative erythema become observed over the whole body. She is complicated with intractable alopecia. | Starting 10 years ago, chronic recurrent dermatitis with itching repeatedly appeared due to the stress caused by professional responsibility. | Developed in infancy, having recurrent eczema with itching; due to steroid external application every day starting 10 years ago, skin flush, scales and infiltrated erythema appeared over the whole body. |
| Family history | Elder brother; Atopic dermatitis | Father; Atopic dermatitis Elder brother: Atopic dermatitis | Mother; Allergic rhinitis | Child; Atopic dermatitis | |
| Past history | Allergic rhinitis, Conjunctivitis | | Allergic rhinitis, | Allergic rhinitis | Allergic rhinitis |
| Scratch test | House dust: 2+ Mite: 2+ Cedar: 2+ Orchard grass: 3+ Ragweed: 2+ | House dust: 1+ Mite: 2+ Egg white: 2+ | House dust: 2+ Mite: 3+ Cedar: 3+ | House dust: 1+ Mite: 3+ Cedar: 1+ Ragweed: 1+ | House dust: 2+ Mite: 1+ Cedar: 2+ Orchard grass: 1+ |
| Diagnostic findings | Infiltrative erythema and swelling of the face and neck are observed, and erythema, scales, adhesion of crusts, and | Infiltrative erythema, lichenified lesions, erythema, severe scales, adhesion of crusts, and numerous | Infiltrative erythema, lichenified lesions, erythema, severe scales, and adhesion of crusts are | Infiltrative erythema, lichenified lesions, erythema, adhesion of crusts and numerous | Infiltrative erythema, lichenified lesions, erythema, severe scales, adhesion of crusts and numerous |

TABLE 13-continued

Diagnosis prior to application of CNP ointment preparation.

| | Subject | | | | |
|---|---|---|---|---|---|
| | Subject 26 | Subject 27 (FIG. 10) | Subject 28 (FIG. 11) | Subject 29 (FIG. 8) | Subject 30 (FIG. 9) |
| | numerous excoriations are observed on the four limbs and body trunk. | excoriations are observed over the whole body. She is in a state of erythroderma posteczematosa. | observed over the whole body. She is in a state of erythroderma posteczematosa. | excoriations are observed on the body trunk. | excoriations are observed over the whole body. He is in a state of erythroderma posteczematosa. |
| Symptoms of application regions | Rash on the face and neck is mainly characterized by erythema with swelling. | Rash on the face consists of infiltration/ severe scales, adhesion of crusts, erosions, and numerous excoriations. | Rash on the face and neck is mainly characterized by infiltrative erythema with swelling. | Rash on the back forms a plaque accompanied by erythema with infiltration/ lichenification, scales, and adhesion of crusts. | Rash on the face and upper limbs is mainly characterized by erythema with severe swelling and infiltration. |
| Effects of steroid external drug | Symptoms recur soon after discontinuation of steroid external therapy. | After discontinuation of steroid external application, skin flush and desquamation appear over the whole body, and she becomes a state of erythroderma. | Not improved even by "very strong" steroid external therapy. | Recurrence appears soon with "very strong" steroid external therapy. | Not improved even by steroid external therapy. |
| Evaluation of symptoms | Severe | Most severe | Most severe | Severe | Most severe |

TABLE 14

Therapeutic effects of CNP ointment preparation.

| | Subject | | | | |
|---|---|---|---|---|---|
| | Subject 26 | Subject 27 (FIG. 10) | Subject 28 (FIG. 11) | Subject 29 (FIG. 8) | Subject 30 (FIG. 9) |
| Case | — | — | — | — | — |
| Sex | Female | Female | Female | Male | Male |
| Age | 32 years old | 3 years old | 22 years old | 44 years old | 36 years old |
| Dosage form | CNP ointment preparation | CNP ointment preparation | CNP ointment preparation | CNP ointment preparation | CNP ointment preparation |
| Dosage | 50 μg/g | 50 μg/g | 50 μg/g | 50 μg/g | 50 μg/g |
| Number of administration | Twice a day | Twice a day | Twice a day | Twice a day | Twice a day |
| Days of administration | 2 days | 3 days | 3 days | 3 days | 2 days |
| Applied region | Face and neck | Face | Face, neck, head | Neck and back | Face and upper limbs |
| Severity level of rash by Dermatological Association Guideline | Before: severe After: mild | Before: severe After: mild | Before: severe After: minor | Before: severe After: mild | Before: severe After: mild |
| Severity level evaluation of the rash region by SCORAD (before application) | Erythema: 3 Edema/papulation: 2 Oozing/crusting: 1 Excoriation: 1 Lichenification: 1 Dryness: 2 Total: 10/18 | Erythema: 3 Edema/papulation: 2 Oozing/crusting: 3 Excoriation: 3 Lichenification: 2 Dryness: 3 Total: 16/18 | Erythema: 3 Edema/papulation: 3 Oozing/crusting: 3 Excoriation: 2 Lichenification: 2 Dryness: 3 Total: 16/18 | Erythema: 3 Edema/papulation: 2 Oozing/crusting: 3 Excoriation: 2 Lichenification: 3 Dryness: 3 Total: 16/18 | Erythema: 3 Edema/papulation: 3 Oozing/crusting: 3 Excoriation: 3 Lichenification: 3 Dryness: 3 Total: 18/18 |
| Severity level evaluation of the rash region by | Erythema: 1 Edema/papulation: 1 Oozing/crusting: 1 Excoriation: 0 | Erythema: 1 Edema/papulation: 1 Oozing/crusting: 1 Excoriation: 1 | Erythema: 0 Edema/papulation: 0 Oozing/crusting: 1 Excoriation: 0 | Erythema: 1 Edema/papulation: 1 Oozing/crusting: 1 Excoriation: 1 | Erythema: 1 Edema/papulation: 0 Oozing/crusting: 1 Excoriation: 1 |

TABLE 14-continued

Therapeutic effects of CNP ointment preparation.

| | Subject 26 | Subject 27 (FIG. 10) | Subject 28 (FIG. 11) | Subject 29 (FIG. 8) | Subject 30 (FIG. 9) |
|---|---|---|---|---|---|
| SCORAD (after application) | Lichenification: 0 Dryness: 1 Total: 4/18 | Lichenification: 1 Dryness: 1 Total: 6/18 | Lichenification: 0 Dryness: 1 Total: 2/18 | Lichenification: 1 Dryness: 1 Total: 6/18 | Lichenification: 1 Dryness: 1 Total: 5/18 |
| Detailed description of improvement status of symptoms | After 2 days of application to the face and neck twice a day, erythema, swelling and itching were improved. | After 3 days of application to the face twice a day, erythema, infiltration, scales, and itching were markedly improved. | After 7 days of application to the face, neck and head twice a day, erythema, infiltration, and itching were improved, and remarkable hair growth was observed in the hair-loss regions. | After 3 days of application to the neck and back twice a day, lichenification, erythema, infiltration, scales and itching were markedly improved. | After 2 days of application to the face and upper limbs twice a day, erythema, excoriations, infiltration and itching were markedly improved. |
| Itching sensation | Before: 10 After: 2 | Before: 10 After: 1 | Before: 10 After: 1 | Before: 10 After: 1 | Before: 10 After: 1 |
| Non-recurrence period | 5 days | 2 weeks | 2 weeks | 2 weeks or more | 5 days |

TABLE 15

Diagnosis prior to application of CNP ointment preparation.

| | Subject 31 | Subject 32 | Subject 33 | Subject 34 | Subject 35 |
|---|---|---|---|---|---|
| Case | — | — | — | — | — |
| Sex | Female | Female | Female | Male | Male |
| Age | 38 years old | 24 years old | 56 years old | 36 years old | 25 years old |
| Onset and course of disease | Developed in infancy; worsening of symptoms was triggered by delivery 7 years ago, and erythema with itching appeared mainly on the face, upper limbs and body trunk; despite application of steroid external drugs, recurrence persisted. | Chronic recurrent dermatitis with itching occurred repeatedly since kindergarten; due to external application of strong steroid ointments, she has erythroderma posteczematosa; she has had cataract surgery and retinal detachment 6 times, and she uses eye-drops to decrease eye pressure. | Skin flush with a burning sensation erythema, and scales appeared on the face since several years ago, and they recurred repeatedly. | Developed in infancy, having recurrent eczema with itching; since 4 years ago, steroid external drugs have been applied every day, resulting in skin flush, scales and infiltrative erythema over the whole body. | Diagnosed to have atopic dermatitis at 2 months of age; since then he has continued to visit dermatology department for treatment, but symptoms worsened starting 2 years ago; he has erythroderma posteczematosa presumably due to long-term steroid external therapy. |
| Family history | Child; Atopic dermatitis | Father, mother; Allergic rhinitis Younger sister; Atopic dermatitis | | Elder brother; Atopic dermatitis, Bronchial asthma | Mother; Atopic dermatitis |
| Past history | Allergic rhinitis, Allergic conjunctivitis | Allergic rhinitis | Allergic rhinitis | Allergic rhinitis | Child asthma, Allergic rhinitis, Allergic conjunctivitis |
| Scratch test | House dust: 2+ Mite: 2+ Cedar: 1+ Orchard grass: 2+ Ragweed: 2+ | House dust: 3+ Mite: 3+ Cedar: 3+ Orchard grass: 1+ Ragweed: 2+ | House dust: 1+ Mite: 2+ Orchard grass: 1+ | House dust: 2+ Mite: 3+ Cedar: 1+ Orchard grass: 3+ Ragweed: 1+ | House dust: 2+ Mite: 3+ Orchard grass: 2+ |
| Diagnostic findings | Infiltrative erythema with itching | Infiltrative erythema, lichenified | Infiltrative erythema, lichenified | Infiltrative erythema, lichenified | Strong itching with sleep disturbance, |

TABLE 15-continued

Diagnosis prior to application of CNP ointment preparation.

| | Subject 31 | Subject 32 | Subject 33 | Subject 34 | Subject 35 |
|---|---|---|---|---|---|
| | associated with sleep disturbance, and erythema are observed on almost whole body. | lesions, erythema, severe scales, adhesion of crusts, and numerous excoriations are observed over the whole body. She has erythroderma posteczematosa. | lesions, erythema, severe scales, adhesion of crusts, and numerous excoriations are observed on the four limbs and face. | lesions, erythema, severe scales, adhesion of crusts, and numerous excoriations are observed over the whole body. He has erythroderma posteczematosa. | infiltrative erythema, lichenified lesions and erythema are observed over the whole body; and severe scales, infiltrative erythema, adhesion of crusts, and numerous excoriations are observed on the face. |
| Symptoms of application regions | Rash on the face is mainly characterized by erythema with severe infiltration and edema. | Rash on the face includes erythema with severe swelling/edema/infiltration/or lichenification, as well as severe scales, adhesion of crusts, vesicles, erosions, and numerous excoriations. | Rash on the face is mainly characterized by erythema, erosions, crusts, and excoriations. | Rash on the face is mainly characterized by erythema with lichenification, erosions, scales, and numerous excoriations. | Rash on the face is mainly characterized by severe infiltration, erythema, exudate, crusts, and numerous excoriations. |
| Effects of steroid external drug | Steroid external drug is not sufficiently effective against erythema, infiltrative erythema and scales on the face, upper limbs and body trunk, which show an intractable nature. | Skin flush and desquamation appear over the whole body upon discontinuation of steroid external application, leading to the state of erythroderma. | Infiltrative erythema on the face is temporarily reduced by steroid external therapy, but symptoms soon recur with a worsening tendency. | Not improved even by "very strong" steroid external therapy. | He has erythroderma posteczematosa presumably due to steroid external therapy. |
| Evaluation of symptoms | Severe | Most severe | Moderate | Most severe | Most severe |

TABLE 16

Therapeutic effects of CNP ointment preparation

| | Subject 31 | Subject 32 | Subject 33 | Subject 34 | Subject 35 |
|---|---|---|---|---|---|
| Case | — | — | — | — | — |
| Sex | Female | Female | Female | Male | Male |
| Age | 38 years old | 24 years old | 56 years old | 36 years old | 25 years old |
| Dosage form | CNP ointment preparation | CNP ointment preparation | CNP ointment preparation | CNP ointment preparation | CNP ointment preparation |
| Dosage | 100 µg/g | 100 µg/g | 100 µg/g | 100 µg/g | 100 µg/g |
| Number of administration | Twice a day | Twice a day | Twice a day | Twice a day | Twice a day |
| Days of administration | 3 days | 3 days | 3 days | 3 days | 3 days |
| Applied region | Face | Face | Face | Face and back | Face |

TABLE 16-continued

Therapeutic effects of CNP ointment preparation

| | Subject | | | | |
|---|---|---|---|---|---|
| | Subject 31 | Subject 32 | Subject 33 | Subject 34 | Subject 35 |
| Severity level of rash by Dermatological Association Guideline | Before: moderate After: minor | Before: severe After: moderate | Before: severe After: minor | Before: severe After: mild | Before: severe After: mild |
| Severity level evaluation of the rash region by SCORAD (before application) | Erythema: 2 Edema/papulation: 2 Oozing/crusting: 1 Excoriation: 1 Lichenification: 1 Dryness: 1 Total: 8/18 | Erythema: 3 Edema/papulation: 2 Oozing/crusting: 3 Excoriation: 3 Lichenification: 3 Dryness: 3 Total: 17/18 | Erythema: 3 Edema/papulation: 2 Oozing/crusting: 3 Excoriation: 1 Lichenification: 1 Dryness: 1 Total: 11/18 | Erythema: 2 Edema/papulation: 1 Oozing/crusting: 2 Excoriation: 2 Lichenification: 3 Dryness: 3 Total: 13/18 | Erythema: 2 Edema/papulation: 2 Oozing/crusting: 3 Excoriation: 3 Lichenification: 2 Dryness: 2 Total: 14/18 |
| Severity level evaluation of the rash region by SCORAD (after application) | Erythema: 0 Edema/papulation: 0 Oozing/crusting: 0 Excoriation: 1 Lichenification: 0 Dryness: 0 Total: 1/18 | Erythema: 1 Edema/papulation: 1 Oozing/crusting: 1 Excoriation: 1 Lichenification: 2 Dryness: 2 Total: 8/18 | Erythema: 0 Edema/papulation: 0 Oozing/crusting: 0 Excoriation: 0 Lichenification: 0 Dryness: 1 Total: 1/18 | Erythema: 1 Edema/papulation: 0 Oozing/crusting: 1 Excoriation: 0 Lichenification: 1 Dryness: 1 Total: 4/18 | Erythema: 1 Edema/papulation: 1 Oozing/crusting: 1 Excoriation: 1 Lichenification: 1 Dryness: 1 Total: 6/18 |
| Detailed description of improvement status of symptoms | After 3 days of application to the face twice a day, erythema and infiltration were markedly improved to the best condition since 20 years ago. | After 3 days of application to the face twice a day, erythema, infiltration, scales, and itching were markedly improved. | After 3 days of application to the face twice a day, erythema, infiltration, crusts, itching, and burning sensation were markedly improved. | After 3 days of application to the face and neck twice a day, erythema, infiltration, scales, and itching were markedly improved. | After 3 days of application to the face twice a day, erythema, infiltration, scales, and itching were markedly improved. |
| Itching sensation | Before: 10 After: 2 | Before: 10 After: 1 | Before: 10 After: 0 | Before: 10 After: 1 | Before: 10 After: 1 |
| Non-recurrence period | 10 days | 7 days | 2 weeks | 2 weeks or more | 5 days |

Summary of Therapeutic Effects of CNP Gel Preparation, CNP Aqueous-Solution Preparation, CNP Gel-Base Preparation, and CNP Ointment Preparation:

The above case studies clarified the following.

By administering skin external preparations comprising CNP, erythema with severe swelling/edema/infiltration, erythema with lichenification, papules, and scales were markedly improved, or they were improved to the mild symptoms that are characterized mainly by dryness, mild erythema, scales, etc., or to the minor rash characterized mainly by dryness with less inflammation. In particular, by administering skin external preparations comprising CNP, skin flush, infiltration, scales lichenification and burning sensation of on the face of adult patients, which are difficult to cure and can disrupt the patients' social lives, could be dramatically improved to a condition without any irritation symptoms. Moreover, remarkable improvement was observed in other regions such as the upper limbs and back, and similar effects were observed for infants as well, and were not limited to adults. Any of these skin external preparations comprising CNP such as CNP gel preparation, CNP aqueous-solution preparation, CNP gel-base preparation and CNP ointment preparation demonstrated almost identical therapeutic effects.

Manifestation of these effects of the skin external preparations comprising CNP is as follows: approximately 10 min after the application, a subjective burning sensation subsides, and on and after approximately 30 min after the application, improvements in erythema and infiltration were objectively observed. Furthermore, continuation of the application for 3 or 4 days apparently reduced erythema and infiltration, resulting in near-normal skin with fine texture. This could be a great relief for patients with severe atopic dermatitis.

In addition, by administering skin external preparations comprising CNP, beneficial changes in vasodilation and inflammatory erythema was observed by the findings in the upper dermis of the skin by dermoscopy. Furthermore, by administering skin external preparations comprising CNP, it was demonstrated that the texture of the skin surface becomes finer, scales decrease, and the skin become soft to the touch. These findings were also confirmed by the findings in the upper dermis of the skin by dermoscopy. The fact that "the texture of the skin surface becomes finer, scales decrease, and the skin become soft to the touch" is important in compensating for skin dryness and deterioration of barrier functions, as well as preventing recurrence of inflammation. Such effects were also observed in psoriasis; disappearance of scales and reduction of infiltration were observed. Neither local irritation symptoms nor systemic side effects were observed at all by the CNP application. Likewise in rosacea, improvements in capillary dilation and erythema were achieved by the CNP application.

These therapeutic effects of good skin conditions were maintained for between 5 days to approximately 2 weeks after discontinuation of the application. Thereafter, even when erythema relapsed, it did not worsen as was observed before the application, and symptoms were merely mild, and this demonstrates that stable conditions could be maintained. This deserves a special note since these effects could not have been obtained by conventional therapy, i.e., steroid external application. In addition, even when symptoms relapsed, it was evident that re-application to the rash could lead to mild or minor rash by a smaller number of applications than the initial application.

The primary goal of treatment of atopic dermatitis is to achieve the following conditions in patients.
(1) No symptoms; if any, minor symptoms without any problems caused in daily life, with a requirement of a low degree of drug therapy.
(2) While minor or mild symptoms persist, there is a small possibility of acute worsening; even when the symptoms worsen, they will not persist for a long time.

The above case studies clearly demonstrated that the skin external preparations comprising CNP of the present invention are able to achieve these conditions in patients.

Next, skin external preparations comprising BNP were examined.

EXAMPLE 13

1. Production of BNP Gel-Base Preparation:

Preparation of the BNP gel-base preparations was performed as follows.

0.1 g of methyl parahydroxybenzoate (product name: Mekkins M, Ueno Fine Chemicals Industry), 0.2 g of phenoxyethanol, and 3.0 g of 1,2-pentanediol were measured in the same container, dissolved at 60-70° C., and introduced into a mixing kettle. 6.0 g of concentrated glycerin was introduced, and a mixture of 0.44 g of carboxy vinyl polymer (product name: Carbopol 940, Lubrisol Advanced Materials, Inc.) and 0.08 g of xanthan gum (product name: Keltrol T, CP Kelco) was added to this solution and stirred thoroughly with a paddle at 15 rpm for dispersion. Then, while stirring with a paddle at 15 rpm, 83.95 g of purified water was gradually introduced, and the mixture was dissolved by stirring at a kettle temperature of 70-80° C. using a paddle at 20 rpm and a disperser at 1500-2000 rpm. After stopping the disperser, dissolution was confirmed and cooling was immediately started; when the kettle temperature approached around 40° C., 6.0 g of Lubrajel NP from ISP Japan, Ltd. (2.7 g of glycerin, 0.06 g of carboxy vinyl polymer, 0.018 g of sodium polyacrylate, 3.222 g of water) was added and mixed homogeneously with a paddle at 20 rpm, then 0.230 g of potassium hydroxide was added for neutralization, and when the kettle temperature reached 25° C., the rotation of the paddle was terminated to obtain a gel-base.

Then, 3 mg of human BNP-32 (Peptide Institute, Inc.) as a principal agent was dissolved in 3 ml of saline to obtain the BNP solution with a concentration of 1000 µg/ml, and 1 ml of this BNP solution was homogeneously stirred and mixed in 19 g of the gel-base obtained as above, to produce the gel-base preparation with a concentration of 50 µg/g.

Similarly, 600 µl of the above BNP solution with a concentration of 1000 µg/ml was diluted with 400 µl of saline to adjust the concentration at 600 µg/ml, then 1 ml of the resulting solution was homogeneously mixed in 19 g of the gel-base obtained as above and stirred, to produce the gel-base preparation with a concentration of 30 µg/g.

EXAMPLE 14

2. Production of BNP Aqueous-Solution Preparation:

3 mg of human BNP-32 (Peptide Institute, Inc.) as a principal agent was dissolved in 3 ml of saline to obtain a BNP solution, and 1 ml of this solution was diluted with 19 ml of saline to produce the aqueous-solution preparation with a BNP concentration of 50 µg/ml.

EXAMPLE 15

3. Diagnosis of Subjects:

The patients' diagnosis, evaluation of symptoms, selection of external therapy, test methods and observation of the skin were performed similarly to the methods of Example 1.

In addition, similarly to the methods of Example 1, prior to administration of the BNP gel-base preparation or BNP aqueous-solution preparation of the present invention, history taking from the subjects, scratch tests for allergens and diagnosis were conducted. Table 17 (subjects 36-40) and Table 19 (subjects 41-45) show the results of the subjects' history taking and diagnosis, i.e., sex, age, onset and course of disease, family history, past history, scratch test results, diagnostic findings, and symptom evaluation based on "Guideline 2005" of the subject in each case.

EXAMPLE 16

4. Therapeutic Effects on Subjects:

Therapeutic effects of the BNP gel-base preparation or BNP aqueous-solution preparation of the present invention are shown in Table 18 (subjects 36-40) and Table 20 (subjects 41-45). In Tables 18 and 20, "itching sensation" represents a comparison of the itching sensation evaluated using the visual analogue scale method before and after treatment. Similarly, "non-recurrence period" refers to the period after discontinuation of the treatment by the preparation of the present invention subsequent to improvement of symptoms, for which relapse of the symptoms did not occur. In order to evaluate objectively, photographs before and after the application of BNP preparations were taken for all cases. Of these, photographs of some of the cases are shown in the figures.

TABLE 17

Diagnosis prior to application of BNP gel-base preparation or BNP aqueous-solution preparation.

| | Subject | | | | |
|---|---|---|---|---|---|
| | Subject 36 | Subject 37 | Subject 38 | Subject 39 | Subject 40 (FIG. 14) |
| Case | Case 7 | Case 6 | Case 2 | Case 3 | Case 5 |
| Sex | Female | Female | Male | Male | Female |
| Age | 32 years old | 22 years old | 31 years old | 21 years old | 36 years old |
| Onset and course of disease | She had severe bronchial asthma until about 20 years of age; since then, she has been suffering mainly from erythema on the face. | Developed soon after birth, continuously receiving steroid external therapy; symptoms worsened in junior-high | Developed atopic dermatitis in infancy; infiltrative erythema appeared particularly on the face recently, | Developed in infancy; symptoms worsened after entering university 3 years ago and eczema is appearing even | Developed in infancy, continuously using commercially-available steroid ointments; but the symptoms do |

TABLE 17-continued

Diagnosis prior to application of BNP gel-base preparation or BNP aqueous-solution preparation.

| | Subject 36 | Subject 37 | Subject 38 | Subject 39 | Subject 40 (FIG. 14) |
|---|---|---|---|---|---|
| | | school. Symptoms relapse soon after discontinuation due to steroid rebound, and worsen further. | showing intractable nature. | on the face. | not subside at all, and she can hardly sleep because of itching. |
| Family history | Elder brother; Atopic dermatitis | Uncle; Allergic rhinitis | Mother; Allergic rhinitis | Father; Bronchial asthma | Father; Atopic dermatitis, Allergic rhinitis |
| Past history | Allergic rhinitis, Conjunctivitis | Allergic rhinitis | Allergic rhinitis | Bronchial asthma | Allergic rhinitis |
| Scratch test | House dust: 3+ Mite: 3+ Cedar: 2+ Orchard grass: 2+ Ragweed: 1+ | House dust: 2+ Mite: 2+ Cedar: 1+ Orchard grass: 2+ Ragweed: 1+ | House dust: 1+ Mite: 3+ Cedar: 3+ | House dust: 2+ Mite: 3+ Cedar: 2+ Orchard grass: 3+ Ragweed: 2+ | House dust: 2+ Mite: 3+ Cedar: 2+ |
| Diagnostic findings | Infiltrative erythema, edema, and erythema are disseminated on the face and neck; papules and erythema are disseminated on the four limbs. | Edema, infiltrative erythema, erythema, scales, and numerous excoriations are observed over the whole body. She has erythroderma posteczematosa. | Infiltrative erythema, erythema and scales on the face, neck and body trunk. | Infiltrative erythema, erythema, many, adhesion of crusts, and excoriations are observed on the face, four limbs, and back. | Infiltrative erythema, erythema, edema, scales, adhesion of crusts, and numerous excoriations are observed on the face, neck, four limbs and body trunk. |
| Symptoms of application regions | Rash on the face and neck is mainly characterized by severe infiltration, erythema and swelling. | Rash on the face and neck is mainly characterized by severe edema, infiltration, erythema, erosions, scales and numerous excoriations. | Rash on the face and neck is mainly characterized by severe infiltration, erythema and scales. | Rash on the face is mainly characterized by infiltrative erythema, many papules, and excoriations. | Rash on the face and neck is mainly characterized by erythema with edema, erosions, scales and numerous excoriations. |
| Effects of steroid external drug | Symptoms relapse soon after discontinuation of steroid external therapy. | Symptoms cannot be improved by steroid external therapy. | Symptoms relapse soon after discontinuation of steroid external therapy. | Symptoms relapse soon after discontinuation of steroid external therapy. | Symptoms are not reduced by steroid external therapy. |
| Evaluation of symptoms | Severe | Most severe | Severe | Severe | Most severe |

TABLE 18

Therapeutic effects of BNP gel-base preparation or BNP aqueous-solution preparation.

| | Subject 36 | Subject 37 | Subject 38 | Subject 39 | Subject 40 (FIG. 14) |
|---|---|---|---|---|---|
| Case | Case 7 | Case 6 | Case 2 | Case 3 | Case 5 |
| Sex | Female | Female | Male | Male | Female |
| Age | 32 years old | 22 years old | 31 years old | 21 years old | 36 years old |
| Dosage form | BNP gel-base preparation | BNP gel-base preparation | BNP gel-base preparation | BNP gel-base preparation | BNP gel-base preparation |
| Dosage | 30 μg/g | 30 μg/g | 50 μg/g | 50 μg/g | 50 μg/g |
| Number of administration | Twice a day | Twice a day | Twice a day | Twice a day | Twice a day |
| Days of administration | 3 days | 5 days | 3 days | 3 days | 2 days |

TABLE 18-continued

Therapeutic effects of BNP gel-base preparation or BNP aqueous-solution preparation.

| | Subject | | | | |
|---|---|---|---|---|---|
| | Subject 36 | Subject 37 | Subject 38 | Subject 39 | Subject 40 (FIG. 14) |
| Applied region | Face | Face and neck | Face | Face | Face and neck |
| Severity level of rash by Dermatological Association Guideline | Before: severe After: minor | Before: severe After: mild | Before: severe After: minor | Before: severe After: mild | Before: severe After: mild |
| Severity level evaluation of the rash region by SCORAD (before application) | Erythema: 3 Edema/papulation: 3 Oozing/crusting: 1 Excoriation: 1 Lichenification: 1 Dryness: 2 Total: 11/18 | Erythema: 3 Edema/papulation: 3 Oozing/crusting: 2 Excoriation: 2 Lichenification: 2 Dryness: 3 Total: 15/18 | Erythema: 3 Edema/papulation: 2 Oozing/crusting: 2 Excoriation: 2 Lichenification: 1 Dryness: 2 Total: 12/18 | Erythema: 3 Edema/papulation: 2 Oozing/crusting: 2 Excoriation: 2 Lichenification: 1 Dryness: 2 Total: 12/18 | Erythema: 3 Edema/papulation: 3 Oozing/crusting: 1 Excoriation: 2 Lichenification: 2 Dryness: 3 Total: 14/18 |
| Severity level evaluation of the rash region by SCORAD (after application) | Erythema: 1 Edema/papulation: 0 Oozing/crusting: 0 Excoriation: 0 Lichenification: 0 Dryness: 0 Total: 1/18 | Erythema: 1 Edema/papulation: 1 Oozing/crusting: 1 Excoriation: 0 Lichenification: 0 Dryness: 1 Total: 4/18 | Erythema: 1 Edema/papulation: 0 Oozing/crusting: 0 Excoriation: 0 Lichenification: 0 Dryness: 1 Total: 2/18 | Erythema: 1 Edema/papulation: 1 Oozing/crusting: 1 Excoriation: 0 Lichenification: 0 Dryness: 1 Total: 4/18 | Erythema: 1 Edema/papulation: 1 Oozing/crusting: 0 Excoriation: 0 Lichenification: 0 Dryness: 1 Total: 3/18 |
| Detailed description of improvement status of symptoms | After 2 to 3 days of application of 30 µg/g BNP gel-base preparation, erythema, edema, dryness and itching were markedly improved. | After 5 days of application of 30 µg/g BNP gel-base preparation to the face and neck twice a day, edema, erythema, excoriations, infiltration, scales, burning sensation and itching were markedly improved. | After 3 days of application of 50 µg/g BNP gel-base preparation to the face twice a day, erythema, infiltration, burning sensation and itching were markedly improved. Symptoms are mainly characterized by dryness with less inflammatory symptoms. | After 3 days of application of 50 µg/g BNP gel-base preparation to the face twice a day, erythema, infiltration, and itching were markedly improved. | By application of 50 µg/g BNP gel-base preparation twice a day, erosions were improved in 1 day, and 2 days later, erythema, infiltration, excoriations and itching were markedly improved. |
| Itching | Before: 10 After: 0 | Before: 10 After: 2 | Before: 10 After: 0 | Before: 10 After: 3 | Before: 10 After: 1 |
| Non-recurrence period | 10 days | 5 days | 2 weeks | 2 weeks | 7 days |

TABLE 19

Diagnosis prior to application of BNP gel-base preparation or BNP aqueous-solution preparation.

| | Subject | | | | |
|---|---|---|---|---|---|
| | Subject 41 (FIG. 12) | Subject 42 (FIG. 13) | Subject 43 (FIG. 15) | Subject 44 | Subject 45 |
| Case | Case 1 | Case 4 | Case 8 | Case 9 | Case 10 |
| Sex | Female | Male | Male | Male | Female |
| Age | 11 years old | 23 years old | 21 years old | 28 years old | 48 years old |
| Onset and course of disease | Developed in infancy; having recurrent eczema that worsens as seasons change; it developed into erythroderma recently. | Developed at around 3 years of age; symptoms worsened after transferring jobs last year. In particular erythema on the face shows intractable nature. | Symptoms worsened since last autumn, and he has eczema over the whole body including the face, and he claims that he can hardly sleep because of itching. | Developed when he was in elementary school. In recent years intractable recurrent erythema became obvious mainly on the face. | Developed at 3 months of age; symptoms worsen as seasons change. Recently the rash worsened due to leisureless life, and she is in a state of erythroderma. |
| Family history | Mother; Atopic dermatitis | | Mother; Allergic rhinitis | Mother; Bronchial asthma | Elder brother; Atopic dermatitis |
| Past history | Allergic rhinitis | Bronchial asthma | | Allergic rhinitis | Allergic rhinitis |

TABLE 19-continued

Diagnosis prior to application of BNP gel-base preparation or BNP aqueous-solution preparation.

| | Subject 41 (FIG. 12) | Subject 42 (FIG. 13) | Subject 43 (FIG. 15) | Subject 44 | Subject 45 |
|---|---|---|---|---|---|
| Scratch test | House dust: 2+<br>Mite: 3+<br>Cedar: 2+<br>Orchard grass: 2+<br>Ragweed: 1+ | House dust: 2+<br>Mite: 3+<br>Cedar: 2+<br>Orchard grass: 2+<br>Ragweed: 1+ | House dust: 3+<br>Mite: 3+<br>Cedar: 2+<br>Orchard grass: 2+<br>Ragweed: 3+ | House dust: 1+<br>Mite: 1+<br>Cedar: 1+<br>Orchard grass: 2+ | House dust: 3+<br>Mite: 3+<br>Cedar: 2+<br>Orchard grass: 3+ |
| Diagnostic findings | Edema, infiltrative erythema, erythema, severe scales, and numerous excoriations are observed over the whole body. She has erythroderma posteczematosa. | Infiltrative erythema, erythema, edema, scales, and adhesion of crusts are observed on the four limbs, body trunk, neck and face. | Infiltrative erythema with lichenification, erythema, many papules and excoriations are observed on the body; and infiltrative erythema, erythema and many papules are observed on the face. | Infiltrative erythema, erythema, edema, scales, and numerous excoriations are observed on the four limbs, body trunk, neck and face. | Skin flush with chills, edema, and infiltrative erythema are observed on the almost whole body. |
| Symptoms of application regions | Rash on the neck is mainly characterized by severe edema, infiltration, erythema, erosions, scales, and numerous excoriations. | Rash on the upper limbs consists of infiltrative erythema, erythema, papules, scales and crusts. | Rash on the face is mainly characterized by infiltrative erythema, many papules, scales and excoriations. | Rash on the face consists of infiltration, erythema, severe scales and crusts. | Rash on the face, neck, and four limbs consist of severe swelling, skin flush and edema. |
| Effects of steroid external drug | Symptoms cannot be improved by steroid external therapy. | Symptoms cannot be controlled by steroid external application. | Symptoms relapse soon after discontinuation of steroid external therapy. | Symptoms soon relapse with steroid external therapy. | She is in a state of erythroderma due to side effects of long-term and excessive steroid external application. |
| Evaluation of symptoms | Most severe | Most severe | Most severe | Severe | Most severe |

TABLE 20

Therapeutic effects of BNP gel-base preparation or BNP aqueous-solution preparation.

| | Subject 41 (FIG. 12) | Subject 42 (FIG. 13) | Subject 43 (FIG. 15) | Subject 44 | Subject 45 |
|---|---|---|---|---|---|
| Case | Case 1 | Case 4 | Case 8 | Case 9 | Case 10 |
| Sex | Female | Male | Male | Male | Female |
| Age | 11 years old | 23 years old | 21 years old | 28 years old | 48 years old |
| Dosage form | BNP gel-base preparation | BNP gel-base preparation | BNP aqueous-solution preparation | BNP aqueous-solution preparation | BNP aqueous-solution preparation |
| Dosage | 50 μg/g | 50 μg/g | 50 μg/ml | 50 μg/ml | 50 μg/ml |
| Number of administration | Twice a day | Twice a day | Twice a day | Twice a day | Twice a day |
| Days of administration | 5 days | 5 days | 5 days | 1 day | 3 days |
| Applied region | Neck | Upper limbs | Face | Face and neck | Face and neck |
| Severity level of rash by Dermatological Association Guideline | Before: severe<br>After: mild | Before: severe<br>After: mild | Before: severe<br>After: mild | Before: severe<br>After: minor | Before: severe<br>After: moderate |
| Severity level evaluation of the rash region by | Erythema: 3<br>Edema/papulation: 3<br>Oozing/crusting: 3<br>Excoriation: 3 | Erythema: 2<br>Edema/papulation: 2<br>Oozing/crusting: 2<br>Excoriation: 2 | Erythema: 3<br>Edema/papulation: 2<br>Oozing/crusting: 2<br>Excoriation: 1 | Erythema: 3<br>Edema/papulation: 2<br>Oozing/crusting: 3<br>Excoriation: 2 | Erythema: 3<br>Edema/papulation: 3<br>Oozing/crusting: 3<br>Excoriation: 2 |

TABLE 20-continued

Therapeutic effects of BNP gel-base preparation or BNP aqueous-solution preparation.

| | Subject | | | | |
|---|---|---|---|---|---|
| | Subject 41 (FIG. 12) | Subject 42 (FIG. 13) | Subject 43 (FIG. 15) | Subject 44 | Subject 45 |
| SCORAD (before application) | Lichenification: 3 Dryness: 2 Total: 17/18 | Lichenification: 2 Dryness: 3 Total: 13/18 | Lichenification: 2 Dryness: 2 Total: 12/18 | Lichenification: 2 Dryness: 2 Total: 14/18 | Lichenification: 3 Dryness: 3 Total: 17/18 |
| Severity level evaluation of the rash region by SCORAD (after application) | Erythema: 1 Edema/papulation: 1 Oozing/crusting: 1 Excoriation: 1 Lichenification: 1 Dryness: 1 Total: 6/18 | Erythema: 1 Edema/papulation: 0 Oozing/crusting: 1 Excoriation: 0 Lichenification: 0 Dryness: 1 Total: 3/18 | Erythema: 1 Edema/papulation: 0 Oozing/crusting: 1 Excoriation: 0 Lichenification: 0 Dryness: 1 Total: 3/18 | Erythema: 1 Edema/papulation: 0 Oozing/crusting: 0 Excoriation: 0 Lichenification: 0 Dryness: 1 Total: 2/18 | Erythema: 2 Edema/papulation: 1 Oozing/crusting: 2 Excoriation: 1 Lichenification: 1 Dryness: 2 Total: 9/18 |
| Detailed description of improvement status of symptoms | After 5 days of application of 50 μg/g BNP gel-base preparation to the neck twice a day, edema, erythema, excoriations, infiltration, scales, burning sensation and itching were markedly improved. Symptoms are mainly characterized by dryness, mild erythema, and scales. | After 3 days of application of 50 μg/g BNP gel-base preparation twice a day, erythema, infiltration, and itching were markedly improved although the skin was slightly dry. | After 2 days of application of 50 μg/ml BNP saline-solution preparation twice a day, erythema, infiltration, scales and itching were markedly improved. | By the application of 50 μg/ml BNP saline-solution preparation twice a day, on the next day, erythema, itching and dryness were markedly improved. | By the application of 50 μg/ml BNP saline-solution preparation twice a day, swelling, erythema, itching sensation and tight-stretched sensation were fairly improved in 1 day, and infiltrative erythema, swelling, excoriations and itching were markedly improved 3 days later; however, scales and dryness still remained. |
| Itching sensation | Before: 10 After: 2 | Before: 10 After: 1 | Before: 10 After: 3 | Before: 10 After: 0 | Before: 10 After: 1 |
| Non-recurrence period | 5 days | 2 weeks | 10 days | 7 days | 5 days |

EXAMPLE 17

Figure 12:
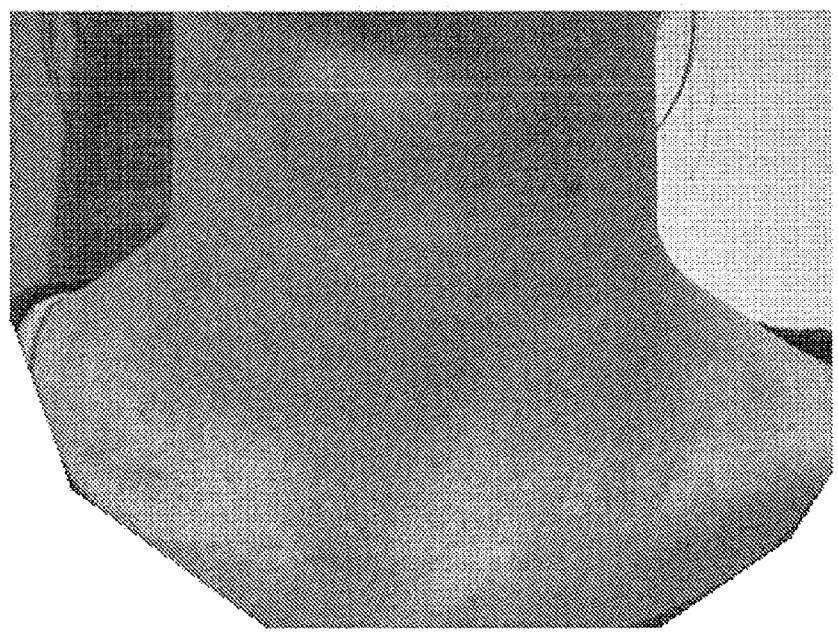
FIG. 12 is a photograph showing the effects of a BNP gel-base preparation of the present invention when it was applied to a patient who had a rash mainly characterized by severe edema, infiltration, erythema, erosions, scales and numerous excoriations on the neck. A shows the state before application, and B shows the state after application of the BNP gel-base preparation with a concentration of 50 μg/g twice a day for 5 days. (Refer to Case 1 of BNP gel-base preparation; subject 41; Tables 19 and 20)
Figure 12:
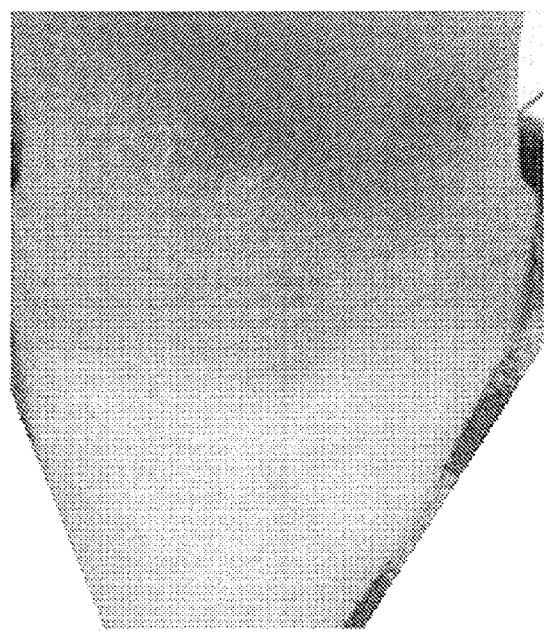
Figure 13:
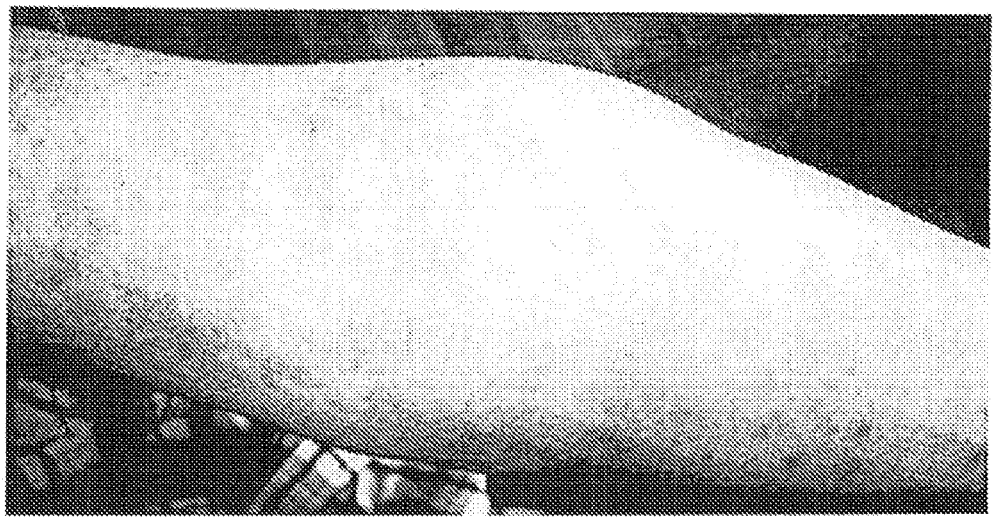
FIG. 13 is a photograph showing the effects of a BNP gel-base preparation of the present invention when it was applied to a patient who had a rash on the forearms, characterized by infiltration, erythema, severe scales and crusts. A shows the state before application, and B shows the state after application of the BNP gel-base preparation with a concentration of 50 μg/g twice a day for 5 days. (Refer to Case 4 of BNP gel-base preparation; subject 42; Tables 19 and 20)
Figure 13:
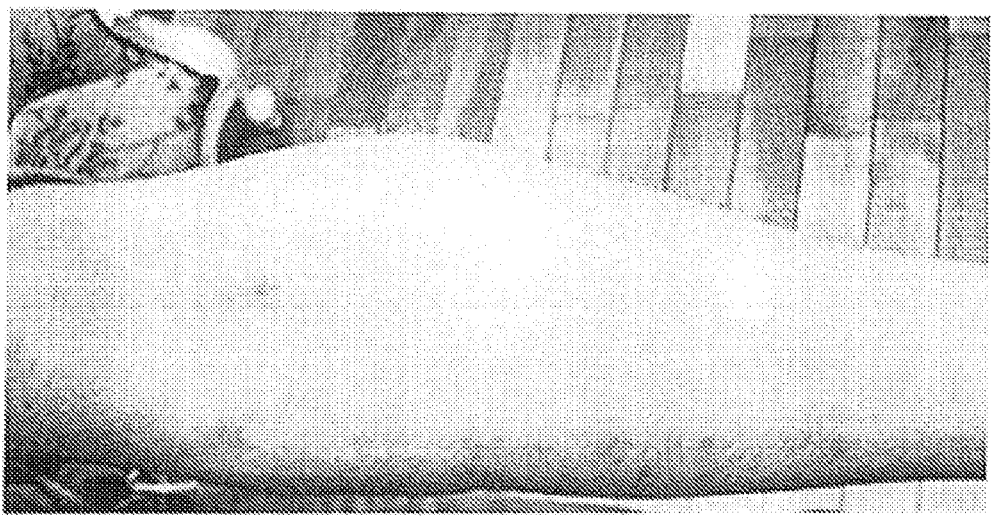
Figure 14:
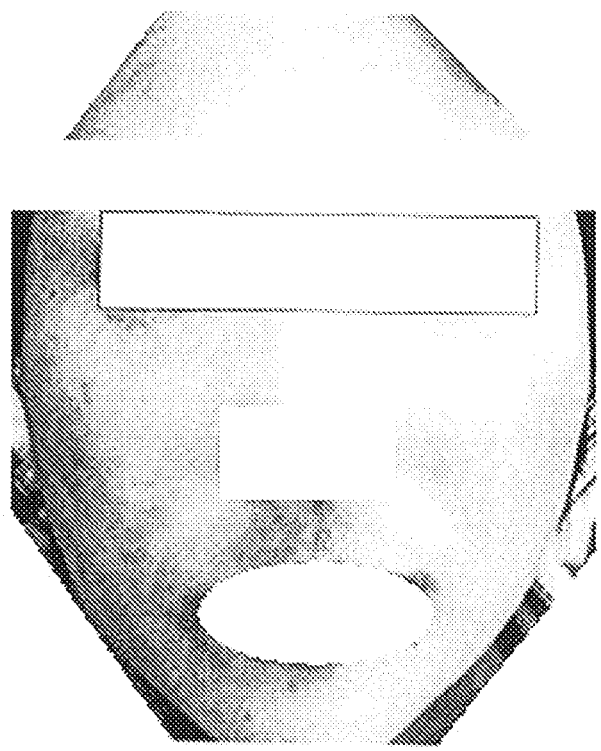
FIG. 14 is a photograph showing the effects of a BNP gel-base preparation of the present invention when it was applied to a patient who had a rash on the face and neck, mainly characterized by erythema with edema, erosions, scales and numerous excoriations. A shows the state before application, and B shows the state after application of the BNP gel-base preparation with a concentration of 50 μg/g twice a day for 2 days. (Refer to Case 5 of BNP gel-base preparation; subject 40; Tables 17 and 18)
Figure 14:
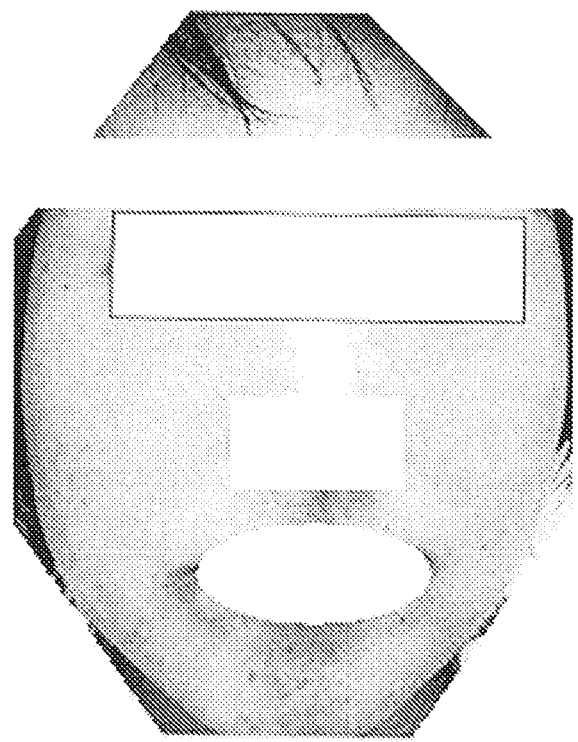

Details of the test examples of the BNP gel-base preparations and BNP aqueous-solution preparations shown in Tables 17-20 are described below. For reference, photographs of Case 1 (subject 41), Case 4 (subject 42), and Case 5 (subject 40) as examples of most severe patients before and after the application are shown in FIGS. 12, 13 and 14, respectively.

BNP test example 1 (Case 1; subject 41):

The subject of Case 1 presented with edema, infiltrative erythema, erythema, severe scales, and numerous excoriations over the whole body, and was diagnosed to be in the state of erythroderma posteczematosa. Furthermore, the rash on the neck was characterized mainly by severe edema, infiltration, erythema, erosions, scales and numerous excoriations, and the severity level based on "Dermatological Association Guideline" was severe. Meanwhile, symptom evaluation according to "Guideline 2005" was most severe. The symptoms of this subject did not improve by the use of steroid external preparations.

Treatment and its Outcome:

To the subject of Case 1, the BNP gel-base preparation with a concentration of 50 μg/g obtained in Example 13 was applied to the neck twice a day; 5 days later, edema, erythema, excoriations, infiltration, scales, burning sensation and itching were markedly improved. Itching sensation level was improved from 10 prior to the application to 2 after the application. FIG. 12 shows photographs before and after 5 days of application; A shows the state before application, and B shows the state after application.

BNP test example 2 (Case 2; subject 38):

The subject of case 2 presented with infiltrative erythema, erythema and scales on the face, neck and body trunk; and the rash on the face and neck was mainly characterized by severe infiltration, erythema and scales. The rash on the face and neck was mainly characterized by severe infiltration, erythema and scales, and the severity level based on "Dermatological Association Guideline" was severe. Meanwhile, symptom evaluation according to "Guideline 2005" was severe. Steroid external therapy was applied to this subject, but the subject had recurrence soon after discontinuation of the external application.

Treatment and its Outcome:

To the subject of Case 2, the BNP gel-base preparation with a concentration of 50 μg/g obtained in Example 13 was applied to the face twice a day; 3 days later, erythema, infiltration, burning sensation and itching were markedly improved. Itching sensation level was improved from 10 prior to the application to 0 after the application.

BNP test example 3(Case 3; subject 39):

The subject of Case 3 presented with infiltrative erythema, erythema, many papules, adhesion of crusts and excoriations on the face, four limbs and back, and the rash on the face was mainly characterized by infiltrative erythema, many papules and excoriations. In addition, the rash on the face and neck was mainly characterized by severe infiltration, erythema and scales, and the severity level based on "Dermatological Association Guideline" was severe. Meanwhile, symptom evaluation based on "Guideline 2005" was severe. Steroid external therapy was applied to this subject; but the subject had recurrence soon after discontinuation of the external application.
Treatment and its Outcome:

To the subject of Case 3, the BNP gel-base preparation with a concentration of 50 μg/g obtained in Example 13 was applied to the face twice a day; 3 days later, erythema, infiltration, and itching markedly improved. Itching level improved from 10 prior to the application to 0 after the application for 3 days.

BNP test example 4 (Case 4; subject 42):

The subject of Case 4 presented with infiltrative erythema, erythema, edema, scales and adhesion of crusts on the four limbs, body trunk, neck and face, and the rash on the upper limbs consists of infiltrative erythema, erythema, papules, severe scales and crusts. In addition, the rash on the upper limbs consists of infiltration, erythema, edema, severe scales and crusts, and the severity level based on the "Dermatological Association Guideline" was severe. Meanwhile, symptom evaluation based on the "Guideline 2005" was most severe, and the symptoms were not improved by steroid external preparations.
Treatment and its Outcome:

The BNP gel-base preparation with a concentration of 50 μg/g obtained in Example 13 was applied to the upper limbs of the subject of Case 4 twice a day; 3 days later, although mild erythema remained, infiltration, papules, scales, crusts and itching were markedly improved. Itching sensation level was improved from 10 prior to the application to 1 after the application for 3 days. FIG. 13 shows photographs before and after 5 days of application. A shows the state before application, and B shows the state after application.

The subject of Case 5 presented with infiltrative erythema, erythema, edema, scales, adhesion of crusts and
BNP test example 5 (Case 5; Subject 40): numerous excoriations on the face, neck, four limbs and body trunk, and the rash on the face and neck was mainly characterized by erythema with edema, erosions, scales, and numerous excoriations. In addition, the rash on the face and neck was mainly characterized by erythema with edema, erosions, scales, and numerous excoriations, and the severity level based on the "Dermatological Association Guideline" was severe. Meanwhile, symptom evaluation based on the "Guideline 2005" was most severe, and the symptoms were not improved by steroid external preparations.
Treatment and its Outcome:

The BNP gel-base preparation with a concentration of 50 μg/g obtained in Example 13 was applied to the face and neck of the subject of Case 5 twice a day; erosions were improved 1 day later, and erythema, infiltration, excoriations and itching were markedly improved 2 days later. Itching sensation level was improved from 10 prior to the application to 1 after the application of 2 days. FIG. 14 shows photographs before and after 1 day of application. A shows the state before application, and B shows the state after application.
BNP test example 6 (Case 6; subject 37):

The subject of Case 6 presented with edema, infiltrative erythema, erythema, severe scales, and numerous excoriations over the whole body, and the subject was in a state of erythroderma posteczematosa. The rash on the face and neck was mainly characterized by severe edema, infiltration, erythema, erosions, scales and numerous excoriations, and the severity level based on the "Dermatological Association Guideline" was severe. Meanwhile, symptom evaluation based on the "Guideline 2005" was most severe, and the symptoms of this subject were not improved by steroid external therapy.
Treatment and its Outcome:

The BNP gel-base preparation with a concentration of 30 μg/g obtained in Example 13 was applied to the face and neck of the subject of Case 6 twice a day; 5 days later, edema, erythema, excoriations, infiltration, scales, burning sensation and itching were markedly improved. Itching sensation level was improved from 10 prior to the application to 2.

BNP test example 7 (Case 7; subject 36):

The subject of Case 7 presented with infiltrative erythema, edema and erythema on the face and neck, and papules and erythema were disseminated on the four limbs. The rash on the face and neck was mainly characterized by severe infiltration, erythema and swelling. The severity level based on the "Dermatological Association Guideline" was severe, and symptom evaluation based on the "Guideline 2005" was severe. Steroid external therapy was applied to this subject, but the subject had recurrence soon after its discontinuation.
Treatment and its Outcome:

The ANP gel-base preparation with a concentration of 50 μg/g obtained in Example 18 was applied to the subject of Case 7, but both erythema and itching worsened by drying. Therefore, the BNP gel-base preparation with a concentration of 30 μg/g obtained in Example 13 was applied to the face twice a day; after 2 to 3 days, erythema, edema, dryness, and itching were markedly improved. Itching sensation level was improved from 10 prior to the application to 0.

Figure 15:
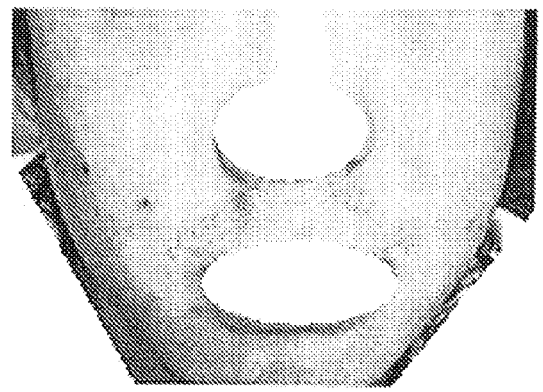
FIG. 15 is a photograph showing the effects of a BNP aqueous-solution preparation of the present invention when it was applied to a patient who had a rash on the face, mainly characterized by infiltrative erythema, many papules, scales and excoriations. A shows the state before application, and B shows the state after application of the BNP aqueous-solution preparation with a concentration of 50 μg/ml twice a day for 5 days. (Refer to Case 8 of BNP aqueous-solution preparation; subject 43; Tables 19 and 20)
Figure 15:
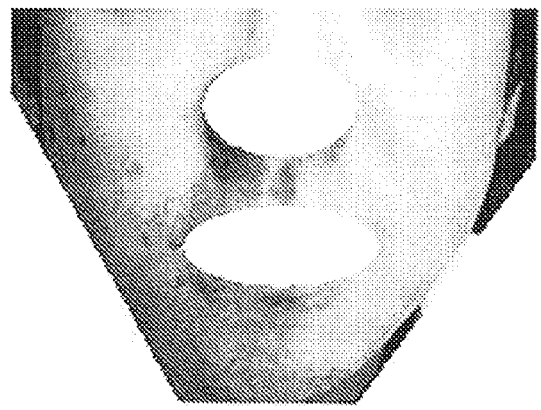

BNP test example 8 (Case 8; subject 43):

The subject of Case 8 presented with infiltrative erythema with lichenification, erythema, many papules, and excoriations on the body, and infiltrative erythema, erythema and many papules on the face; the rash on the face was mainly characterized by infiltrative erythema, many papules, scales and excoriations. The severity level based on the "Dermatological Association Guideline" was severe, and symptom evaluation based on the "Guideline 2005" was most severe. Steroid external therapy was applied to this subject, but the subject had recurrence soon after its discontinuation.
Treatment and its Outcome:

The BNP aqueous-solution preparation with a concentration of 50 μg/ml obtained in Example 14 was applied to the subject of Case 8 twice a day; after 2 days, erythema, infiltration, scales, and itching were markedly improved. Itching sensation level was improved from 10 prior to the application to 3. FIG. 15 shows photographs before and after 5 days of application. A shows the state before application, and B shows the state after application.

BNP test example 9 (Case 9; subject 44):

The subject of Case 9 presented with infiltrative erythema, erythema, edema, scales and numerous excoriations on the four limbs, body trunk, neck and face, and the rash on the face consisted of infiltration, erythema, severe scales and crusts. The severity level based on the "Dermatological Association Guideline" was severe, and symptom evaluation based on the "Guideline 2005" was severe. Steroid external therapy was applied to this subject, but the subject had recurrence soon after its discontinuation.

Treatment and its Outcome:

The ANP gel-base preparation with a concentration of 50 µg/g obtained in Example 18 was applied to the subject of Case 9; while redness of the skin slightly disappeared after approximately 3 days, erythema did not fade away any more even after 7 days of further application, and scales also remained. Therefore, the BNP aqueous-solution preparation with a concentration of 50 µg/ml obtained in Example 14 was applied to the face and neck twice a day; then erythema, itching, and dryness were markedly improved on the next day. Itching sensation level was improved from 10 prior to the application to 0.

BNP test example 10 (Case 10; subject 45):

The subject of Case 10 presented with skin flush with chills, edema, and infiltrative erythema on almost the whole body, and the rash on the face, neck and four limbs consisted of severe swelling, skin flush, and edema. The severity level based on the "Dermatological Association Guideline" was severe, and symptom evaluation based on the "Guideline 2005" was most severe. Due to side effects caused by a long period of steroid external therapy and its excessive application, the subject was in a state of erythroderma.
Treatment and its Outcome:

The subject of Case 10 is the subject of Comparative case 3 in the comparative test example in which the later-described ANP gel-base preparation has been applied. The BNP aqueous-solution preparation with a concentration of 50 µg/ml obtained in Example 14 was applied to the face and neck of this subject twice a day; swelling, erythema, itching, and the sensation of tight-stretched skin were fairly improved the next day, and 3 days later, infiltrative erythema, swelling, excoriations, and itching were markedly improved, but scales and dryness still remained. Itching sensation level was improved from 10 prior to the application to 1.

Subsequently, the ANP aqueous solution with a concentration of 50 µg/g was applied twice a day, then the areas of erythema extended in one day, and itching worsened to a level that could be clearly perceived subjectively.
Summary of Therapeutic Effects of BNP Gel-Base Preparation And BNP Aqueous-Solution Preparation:

The above case studies clarified the following.

By administering skin external preparations comprising BNP, erythema with severe swelling/edema/infiltration, erythema with lichenification, papules, and scales were markedly improved, or they were improved to the mild symptoms mainly characterized by dryness, mild erythema, scales, etc., or to the minor rash mainly characterized by dryness with less inflammation. In particular, by administering skin external preparations comprising BNP, skin flush, infiltration, scales lichenification and burning sensation on the face of adult patients, which are hardly curable and can disrupt the patients' social lives, could be dramatically improved to a condition without any irritation symptoms. Any of these skin external preparations comprising BNP such as BNP aqueous-solution preparation and BNP gel-base preparation demonstrated almost identical therapeutic effects.

Due to such effects of the skin external preparations comprising BNP, continuation of application for 3 to 4 days apparently reduced erythema and infiltration, resulting in almost normal skin with fine texture in some cases. This could be a great relief for patients with severe atopic dermatitis.

In addition, by administering skin external preparations comprising BNP, improvement of vasodilation and inflammatory erythema was confirmed from findings in the upper dermis of the skin by dermoscopy. Furthermore, by administering skin external preparations comprising BNP, it was confirmed that the texture of the skin surface becomes finer, scales decrease, and the skin becomes soft to the touch. These findings were also confirmed by the findings in the upper dermis of the skin by dermoscopy. The fact that "the texture of the skin surface becomes finer, scales decrease, and the skin become soft to the touch" is important in compensating for skin dryness and deterioration of barrier functions as well as preventing recurrence of inflammation. Such effects were also observed in psoriasis; disappearance of scales and improvement of infiltration were confirmed. Neither local irritation symptom nor systemic side effect was observed at all by the BNP application. In rosacea as well, improvement in capillary dilation and erythema was observed by the BNP application.

These effects of BNP therapeutic preparations for dermatitis were almost similar to those of CNP claimed in the priority application, which include the following: subjective burning sensation and sensation of heaviness were improved at approximately 20 min after the application, and at approximately 40 min after the application, improvement of erythema, infiltration and swelling were objectively observed. Moreover, after 2 to 3 days of application, erythema with severe infiltration/edema/swelling, erythema with lichenification, papules and scales were markedly improved to symptoms mainly characterized by dryness, mild to minor erythema and scales, etc. The continuation of the effects was also observed, and good skin conditions were maintained for 5 days to around 2 weeks after discontinuation of the application.

Thereafter, even when erythema relapsed, it did not worsen as was observed before the application, and symptoms were merely mild, and it was confirmed that stable conditions could be maintained. This deserves a special note since these effects could not have been obtained by conventional therapy, i.e., steroid external application. In addition, even when symptoms relapsed, it was confirmed that re-application to the rash could lead to mild or minor rash by a smaller number of application than the initial application.

Regarding the degree of improvement of the rash, the severity level of the rash based on the "Dermatological Association Guideline" were improved from severe to mild or minor. According to the severity level of local symptoms based on the globally used "SCORAD index: Clinical Evaluation", severity levels for most of the items "Erythema", "Edema/population", "Oozing/crusting", "Excoriation" and "Lichenification" were improved from stage 3 to stage 1, i.e., the most mild state.

In the first place, the goal of treatment of atopic dermatitis is to achieve the following conditions in patients.
(1) No symptoms; if any, minor symptoms without any problem in daily life, with a requirement of a low degree of drug therapy.
(2) While minor or mild symptoms persist, there is low possibility of acute worsening; even when the symptoms worsen, they will not persist for a long time.

The above case studies clearly confirmed that the skin external preparations comprising BNP of the present invention are able to achieve these conditions in patients.

EXAMPLE 18

Comparative test
1. Production of ANP Gel-Base Preparation:
For comparative testing, ANP gel-base preparations were prepared as follows.

0.1 g of methyl parahydroxybenzoate (product name: Mekkins M, Ueno Fine Chemicals Industry), 0.2 g of phenoxyethanol, and 3.0 g of 1,2-pentanediol were measured in the same container, dissolved at 60-70° C., and introduced into a mixing kettle. 6.0 g of concentrated glycerin was introduced and a mixture of 0.44 g of carboxy vinyl polymer (product name: Carbopol 940, Lubrisol Advanced Materials, Inc.) and 0.08 g of xanthan gum (product name: Keltrol T, CP Kelco) was added to this solution and stirred thoroughly with a paddle at 15 rpm for dispersion. Then, while stirring with a paddle at 15 rpm, 83.95 g of purified water was gradually introduced, and the mixture was dissolved by stirring at a kettle temperature of 70-80° C. using a paddle at 20 rpm and a disperser at 1500-2000 rpm. After stopping the disperser, dissolution was confirmed and cooling was immediately started; when the kettle temperature approached around 40° C., 6.0 g of Lubrajel NP from ISP Japan, Ltd. (2.7 g of glycerin, 0.06 g of carboxy vinyl polymer, 0.018 g of sodium polyacrylate, 3.222 g of water) was added and mixed homogeneously with a paddle at 20 rpm, then 0.230 g of potassium hydroxide was added for neutralization, and when the kettle temperature reached 25° C., the rotation of the paddle was terminated to obtain a gel base.

Then, 1000 μg of HANP injection 1000 (carperitide for injection; α-atrial natriuretic peptide preparation) as a principal agent was dissolved in 10 ml of an injection solvent to obtain the ANP solution with a concentration of 100 μg/ml, and 10 ml of this ANP solution was diluted with 10 g of the gel-base obtained as above, to produce a gel-base preparation with an ANP concentration of 50 μg/g.

In addition, in order to conduct the comparison under the same condition as BNP, human ANP-28 (Peptide Institute, Inc.) was also used for the examination. In this case, 0.5 mg of human ANP-28 was dissolved in 1 ml of purified water to obtain an ANP solution with a concentration of 500 μg/ml, then 1.0 ml of this solution was homogeneously mixed and stirred in 9 g of the above gel-base to obtain the ANP gel-base preparation. The ANP concentration of this gel-base preparation is 50 μg/g.

EXAMPLE 19

2. Production of ANP Aqueous-Solution Preparation:

0.5 mg of human ANP-28 (Peptide Institute, Inc.) as a principal agent was dissolved in 1 ml of purified water to obtain an ANP solution, and 1.0 ml of this solution was diluted with 9 ml of purified water to produce the aqueous-solution preparation with an ANP concentration of 50 μg/ml.

EXAMPLE 20

3. Diagnosis of Subjects:

Patients' diagnosis, evaluation of symptoms, selection of external therapy, test method and observation of the skin were performed similarly to the methods of Example 1.

In addition, similarly to the methods of Example 1, prior to administration of the ANP gel-base preparation of the present invention, history taking from subjects, scratch tests for allergens, and diagnosis were conducted. Table 21 (subjects 45-49) shows the results of the subjects' history taking and diagnosis, i.e., sex, age, onset and course of disease, family history, past history, scratch test result, diagnostic findings, and symptom evaluation based on the "Guideline 2005" of the subject in each case.

EXAMPLE 21

4. Therapeutic Effects on Subjects:

Therapeutic effects of the ANP gel-base preparation of the present invention are shown in Table 22 (subjects 45-49). In Table 22, "itching sensation" represents comparison of the itching sensation evaluated using visual analogue scale method before and after treatment. Similarly, "non-recurrence period" refers to the period after discontinuation of the treatment by the preparation of the present invention subsequent to improvement of symptoms, for which relapse of the symptoms did not occur. In order to evaluate the results objectively, photographs before and after the application of ANP preparations were taken for all cases. Of these, photographs of some of the cases are shown in the figures.

TABLE 21

Diagnosis prior to application of ANP gel-base preparation.

| | Subject | | | | |
|---|---|---|---|---|---|
| | Subject 45 (FIG. 17) | Subject 46 (FIG. 16) | Subject 47 | Subject 48 (FIG. 18) | Subject 49 |
| Case | Case 3 | Case 2 | Case 4 | Case 5 | Case 1 |
| Sex | Female | Female | Female | Male | Male |
| Age | 48 years old | 27 years old | 21 years old | 28 years old | 14 years old |
| Onset and course of disease | Developed at 3 months of age; symptoms worsen as seasons change. Recently the rash worsened due to leisureless life, and she is in a sate of erythroderma. | Developed in infancy; symptoms worsened since the start of menstruation in the junior high school, and they were alleviated during pregnancy, but relapsed after birth, extending to the whole body. | Developed in infancy; symptoms worsen in dry seasons, and erythema with itching appeared mainly on the face, neck, upper limbs and trunk; they relapse and worsen due to steroids. | Developed in infancy; symptoms were mainly on the body trunk and four limbs; they extended to the face and neck after he reached adulthood. In particular, the rash on the back shows intractable nature. | Developed in infancy; symptoms worsened since around the 2nd grade of elementary school, and he visited many clinics but they were not improved; starting 5 years ago, dryness has become particularly severe. |
| Family history | Elder brother; Atopic dermatitis, | Younger brother; Bronchial asthma, Mother; Allergic rhinitis | Mother; Atopic dermatitis | | Mother; Allergic rhinitis, Allergic conjunctivitis |

TABLE 21-continued

Diagnosis prior to application of ANP gel-base preparation.

| | Subject 45 (FIG. 17) | Subject 46 (FIG. 16) | Subject 47 | Subject 48 (FIG. 18) | Subject 49 |
|---|---|---|---|---|---|
| Past history | Allergic rhinitis | Allergic rhinitis | Allergic rhinitis, Allergic conjunctivitis | Allergic rhinitis | Bronchial asthma, Allergic rhinitis, Allergic conjunctivitis |
| Scratch test | House dust: 3+ Mite: 3+ Cedar: 2+ Orchard grass: 3+ | House dust: 2+ Mite: 3+ | House dust: 1+ Mite: 1+ Cedar: 2+ Orchard grass: 2+ | House dust: 1+ Mite: 2+ Cedar: 1+ Orchard grass: 3+ Ragweed: 1+ | House dust: 3+ Mite: 3+ Cedar: 3+ Orchard grass: 2+ |
| Diagnostic findings | Skin flush with chills, edema, and infiltrative erythema are observed on the almost whole body. | Infiltrative erythema with lichenification, erythema, and severe scales are observed on the face and neck, infiltrated erythema is observed on the four limbs and body trunk. | Infiltrative erythema, erythema, severe scales, adhesion of crusts, and numerous excoriations are observed over the whole body, and they are particularly severe on the face and neck. | Infiltrative erythema, erythema, numerous excoriations, and papules are particularly severely observed on the back. | Erythema with strong itching associated with sleep disturbance, severe scales, and numerous excoriations are observed over the whole body. |
| Symptoms of application regions | Rash on the face, neck, and four limbs consist of severe swelling, skin flush and edema. | Rash on the face is mainly characterized by severe lichenified infiltration, erythema, and scales. | Rash on the face is mainly characterized by severe infiltration, edema, erythema, scales, crusts and excoriations. | Rash on the back consists of severe infiltration, erythema, numerous excoriations, papules and lichenification. | Rash on the back is mainly characterized by severe scales, erythema, and numerous excoriations. |
| Effects of steroid external drug | She is in a state of erythroderma due to the side effects by long-term steroid external therapy and excessive application. | Steroid external therapy is not sufficiently effective to infiltrative erythema on the face. | Symptoms on the face soon relapse with the use of steroid, and further worsen compared to the condition before the use. | Sufficient effects cannot be obtained with steroid external application, and symptoms soon relapse strong itching does not subside. | Symptoms are temporarily reduced with steroid external therapy, but soon relapse and dryness occurs. |
| Evaluation of symptoms | Most severe | Most severe | Severe | Severe | Most severe |

TABLE 22

Therapeutic effects of ANP gel-base preparation.

| | Subject 45 (FIG. 17) | Subject 46 (FIG. 16) | Subject 47 | Subject 48 (FIG. 18) | Subject 49 |
|---|---|---|---|---|---|
| Case | Case 3 | Case 2 | Case 4 | Case 5 | Case 1 |
| Sex | Female | Female | Female | Male | Male |
| Age | 48 years old | 27 years old | 21 years old | 28 years old | 14 years old |
| Dosage form | ANP gel-base preparation | ANP gel-base preparation | ANP gel-base preparation | ANP gel-base preparation | ANP gel-base preparation |
| Dosage | 50 µg/g | 50 µg/g | 50 µg/g | 50 µg/g | 50 µg/g |
| Number of administration | Twice a day | Twice a day | Twice a day | Twice a day | Twice a day |
| Days of administration | 7 days | 7 days | 5 days | 5 days | 7 days |
| Applied region | Face and upper limbs | Face and neck | Face | Back | Back |
| Severity level of rash by | Before: severe After: severe | Before: severe After: severe | Before: severe After: severe | Before: severe After: severe | Before: severe After: severe |

TABLE 22-continued

Therapeutic effects of ANP gel-base preparation.

| | Subject | | | | |
|---|---|---|---|---|---|
| | Subject 45 (FIG. 17) | Subject 46 (FIG. 16) | Subject 47 | Subject 48 (FIG. 18) | Subject 49 |
| Dermatological Association Guideline Severity level evaluation of the rash region by SCORAD (before application) | Erythema: 3 Edema/papulation: 3 Oozing/crusting: 3 Excoriation: 1 Lichenification: 2 Dryness: 3 Total: 15/18 | Erythema: 2 Edema/papulation: 2 Oozing/crusting: 1 Excoriation: 1 Lichenification: 2 Dryness: 3 Total: 11/18 | Erythema: 3 Edema/papulation: 2 Oozing/crusting: 3 Excoriation: 2 Lichenification: 2 Dryness: 2 Total: 14/18 | Erythema: 3 Edema/papulation: 2 Oozing/crusting: 3 Excoriation: 3 Lichenification: 3 Dryness: 2 Total: 16/18 | Erythema: 2 Edema/papulation: 1 Oozing/crusting: 2 Excoriation: 2 Lichenification: 2 Dryness: 3 Total: 12/18 |
| Severity level evaluation of the rash region by SCORAD (after application) | Erythema: 3 Edema/papulation: 2 Oozing/crusting: 3 Excoriation: 2 Lichenification: 2 Dryness: 3 Total: 15/18 | Erythema: 3 Edema/papulation: 2 Oozing/crusting: 2 Excoriation: 1 Lichenification: 2 Dryness: 3 Total: 13/18 | Erythema: 3 Edema/papulation: 2 Oozing/crusting: 2 Excoriation: 2 Lichenification: 2 Dryness: 2 Total: 13/18 | Erythema: 3 Edema/papulation: 3 Oozing/crusting: 3 Excoriation: 3 Lichenification: 3 Dryness: 2 Total: 17/18 | Erythema: 2 Edema/papulation: 1 Oozing/crusting: 2 Excoriation: 2 Lichenification: 2 Dryness: 3 Total: 12/18 |
| Detailed description of improvement status of symptoms | By the application of 50 μg/g ANP gel-base preparation twice a day, edema was slightly reduced, but skin flush and erythema were not improved even after 7 days. | Despite the application of 50 μg/g ANP gel-base preparation twice a day for 7 days, redness did not disappear and erythema and scales worsened. | Despite the application of 50 μg/g ANP gel-base preparation twice a day, erythema and infiltration were not reduced at all even after 5 days. | Despite the application of 50 μg/g ANP gel-base preparation twice a day for 3 days, erythema and itching were not improved and edema even worsened. | Despite the application of 50 μg/g ANP gel-base preparation twice a day for 7 days, severe scales, erythema and numerous excoriations still remained just as the condition before application. |
| Itching sensation | Before: 10 After: 10 | Before: 10 After: 10 | Before: 10 After: 10 | Before: 10 After: 10 | Before: 10 After: 10 |
| Non-recurrence period | — | — | — | — | — |

EXAMPLE 22

Figure 16:
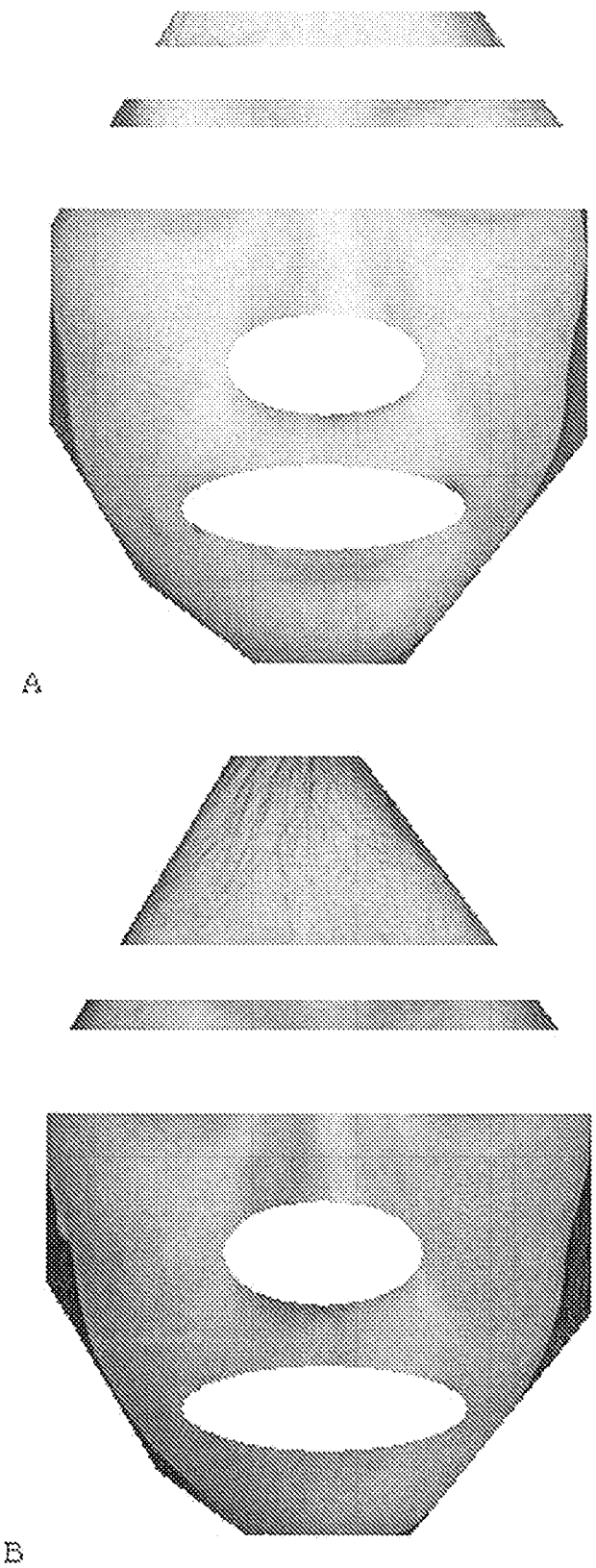
FIG. 16 is a photograph showing the effects in a comparative case when an ANP gel-base preparation was applied to a patient who had a rash on the face, mainly characterized by severe lichenified infiltration, erythema and scales. A shows the state before application, and B shows the state after application of the ANP gel-base preparation with a concentration of 50 μg/g twice a day for days. (Refer to Case 2 of ANP gel-base preparation; subject 46; Tables 21 and 22)
Figure 17:
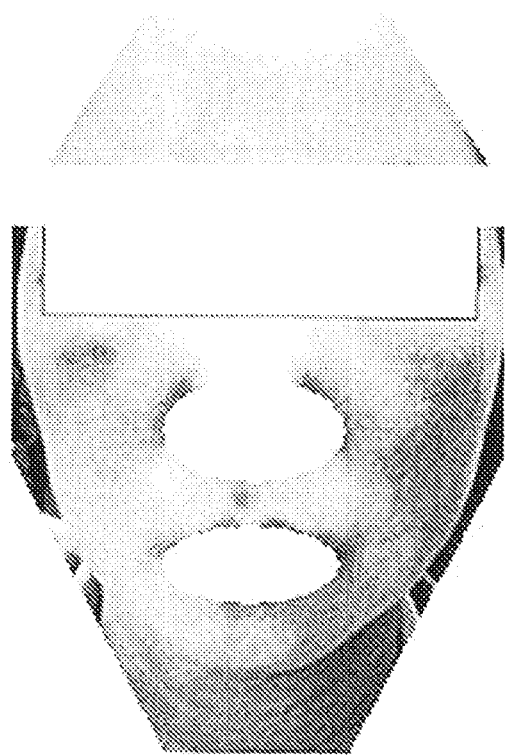
FIG. 17 is a photograph showing the effects in a comparative case when an ANP gel-base preparation was applied to a patient who had a rash on the face, neck and the four limbs, characterized by severe swelling, skin flush and edema. A shows the state before application, and B shows the state after application of the ANP gel-base preparation with a concentration of 50 μg/g twice a day for days. (Refer to Case 3 of ANP gel-base preparation; subject 45; Tables 21 and 22)
Figure 17:
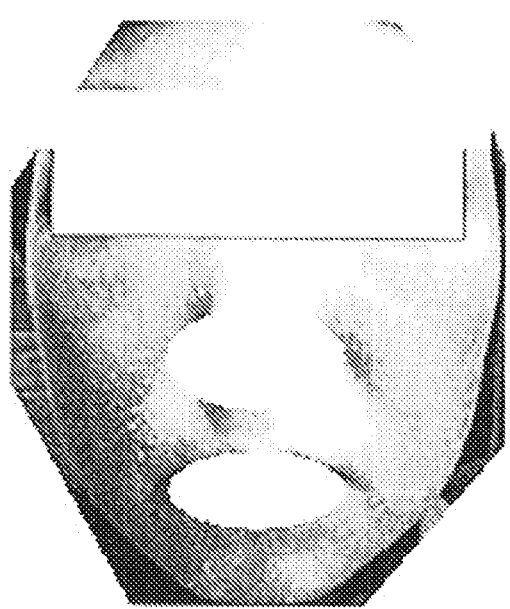
Figure 18:
FIG. 18 is a photograph showing the effects in a comparative case when an ANP gel-base preparation was applied to a patient who had a rash on the back, characterized by severe infiltration, erythema, numerous excoriations, papules and lichenification. A shows the state before application, and B shows the state after application of the ANP gel-base preparation with a concentration of 50 μg/g twice a day for 5 days. (Refer to Case 5 of ANP gel-base preparation; subject 48; Tables 21 and 22)
Figure 18:

For comparison, a test was performed using the ANP gel-base preparation with a concentration of 50 μg/g obtained in Example 18. For reference, as photographs before and after application, FIG. 16 shows photographs of Comparative test example 2 (Case 2; subject 46), FIG. 17 shows photographs of Comparative test example 3 (Case 3; subject 45), and FIG. 18 shows photographs of Comparative test example 5 (Case 5; subject 48).

Comparative test example 1 (Case 1; subject 49):

The subject of Comparative case 1 presented with erythema with strong itching associated with sleep disturbance, severe scales and numerous excoriations over the whole body. In addition, the rash on the back was mainly characterized by severe scales, erythema and numerous excoriations, and the severity level based on the "Dermatological Association Guideline" was severe. The symptom evaluation of this subject based on the "Guideline 2005" was most severe, and the symptoms were reduced temporarily by steroid external therapy, but they relapsed immediately and the skin dried.

Treatment and its Outcome:

The ANP gel-base preparation with a concentration of 50 μg/g obtained in Example 18 was applied to the back of the subject of Comparative case 1 twice a day for 7 days, but the severe scales, erythema and numerous excoriations remained unchanged compared to the condition before the application. The itching sensation level before application was 10, and it was still 10 after application; the severity level remained severe after application.

Comparative test example 2 (Case 2; subject 46):

The subject of Comparative case 2 presented with infiltrative erythema with lichenification, erythema, and severe scales on the face and neck, and infiltrative erythema on the four limbs and body trunk. The rash on the face was mainly characterized by severe lichenified infiltration, erythema and scales, and the severity level based on the "Dermatological Association Guideline" was severe. The symptom evaluation of this subject based on the "Guideline 2005" was most severe, and sufficient effects of steroid external therapy were not observed for the infiltrative erythema on the face.

Treatment and its Outcome:

The ANP gel-base preparation with a concentration of 50 μg/g obtained in Example 18 was applied to the face and neck of the subject of Comparative case 2 twice a day for 7 days, but redness did not disappear, and both erythema and scales worsened. FIG. 16 shows photographs before and after 5 days of application. A shows the state before application, and B shows the state after application. The itching sensation level before application was 10, and it was still 10 after application; the severity level remained severe after application.

Comparative test example 3 (Case 3; subject 45):

The subject of Comparative case 3 presented with skin flush with chills, edema, and infiltrative erythema on the almost whole body. The rash on the face, neck, and four limbs consists of severe swelling, skin flush, and edema, and the severity level based on the "Dermatological Association Guideline" was severe. The symptom evaluation of this subject based on the "Guideline 2005" was most severe, and due to the side effects caused by a long period of steroid external therapy and its excessive application, the subject was in a state of erythroderma.

Treatment and its Outcome:

The ANP gel-base preparation with a concentration of 50 μg/g obtained in Example 18 was applied to the face and upper limbs of the subject of Comparative case 3 twice a day, then edema was slightly reduced, but both skin flush and erythema was not improved even after 7 days of application. FIG. 17 shows photographs before and after days of application. A shows the state before application, and B shows the state after application. The itching sensation level before application was 10, and it was still 10 after application; the severity level remained severe after application.

Comparative test example 4 (Case 4; subject 47):

The subject of Comparative case 4 presented with infiltrative erythema, erythema, severe scales, adhesion of crusts, and numerous excoriations over the whole body, and they are particularly severe on the face and neck. The rash on the face was mainly characterized by severe infiltration, edema, erythema, papules, scales, crusts and excoriations, and the severity level based on the "Dermatological Association Guideline" was severe. The symptom evaluation of this subject based on the "Guideline 2005" was severe; and despite the use of steroids, symptoms on the face soon relapsed and they tended to worsen compared to those before the application.

Treatment and its Outcome:

The ANP gel-base preparation with a concentration of 50 μg/g obtained in Example 18 was applied to the face of the subject of Comparative case 4 twice a day, but both erythema and infiltration was not reduced even after 5 days of application. The itching sensation level before application was 10, and it was still approximately 10 after application; the severity level remained severe after application.

Comparative test example 5 (Case 5; subject 48):

The subject of Comparative case 5 presented with infiltrative erythema, erythema, numerous excoriations and papules particularly on the back. The rash on the back consists of severe infiltration, erythema, numerous excoriations, papules and lichenification, and the severity level based on the "Dermatological Association Guideline" was severe. The symptom evaluation of this subject based on the "Guideline 2005" was severe, and sufficient effects were not observed by steroid external application, the symptoms relapsed soon, and strong itching was not reduced.

Treatment and its Outcome:

The ANP gel-base preparation with a concentration of 50 μg/g obtained in Example 18 was applied to the back of the subject of Comparative case 5 twice a day, but no effect was observed for both erythema and itching after 3 days of application. FIG. 18 shows photographs before and after 5 days of application. A shows the state before application, and B shows the state after application. The itching sensation level before application was 10, and it was still 10 after application; the severity level remained severe after application.

Summary of the comparative test examples:

The above comparative case studies clarified the following.

According to the comparative tests using external preparations comprising ANP, the ANP external preparations with the same concentration as CNP or BNP exhibited marginal effects in a certain cases; however, onset of the effects required approximately 3 days of application, and erythema did not disappear completely; even when application was continued for 7 days or more, erythema did not disappear as in the cases of therapeutic agents for dermatitis comprising CNP or BNP, and erythema even worsened in some cases. Furthermore, when the external application was discontinued, symptoms soon relapsed and dryness increased, with enhanced itching. Apparently, these effects were inferior to those of the therapeutic agents for dermatitis comprising CNP or BNP. In many cases, ANP external preparations did not improve the conditions or even worsened the conditions, and improvement of the rash was, in terms of the severity level of the rash by the "Dermatological Association Guideline", from severe to severe, remaining at the same level. According to the severity level of local symptoms based on the globally used "SCORAD index: Clinical Evaluation" including the items "Erythema", "Edema/papulation", "Oozing/crusting", "Excoriation" and "Lichenification", severity levels for "Edema/papulation" and "Oozing/crusting" were improved from stage 3 to stage 2 in some of the cases; however, those for "Excoriation," "Lichenification" and "Erythema" remained at the same level of stage 3.

In the first place, the goal of treatment of atopic dermatitis is to achieve the following conditions in patients.

(1) No symptoms; if any, minor symptoms without any problem in daily life, with a requirement of a low degree of drug therapy.

(2) While minor or mild symptoms persist, there is low possibility of acute worsening; even when the symptoms worsen, they will not persist for a long time.

The above comparative case studies confirmed that the skin external preparation comprising ANP was unable to achieve these conditions in patients.

Comprehensive summary of the effects of the invention

Figure 19:
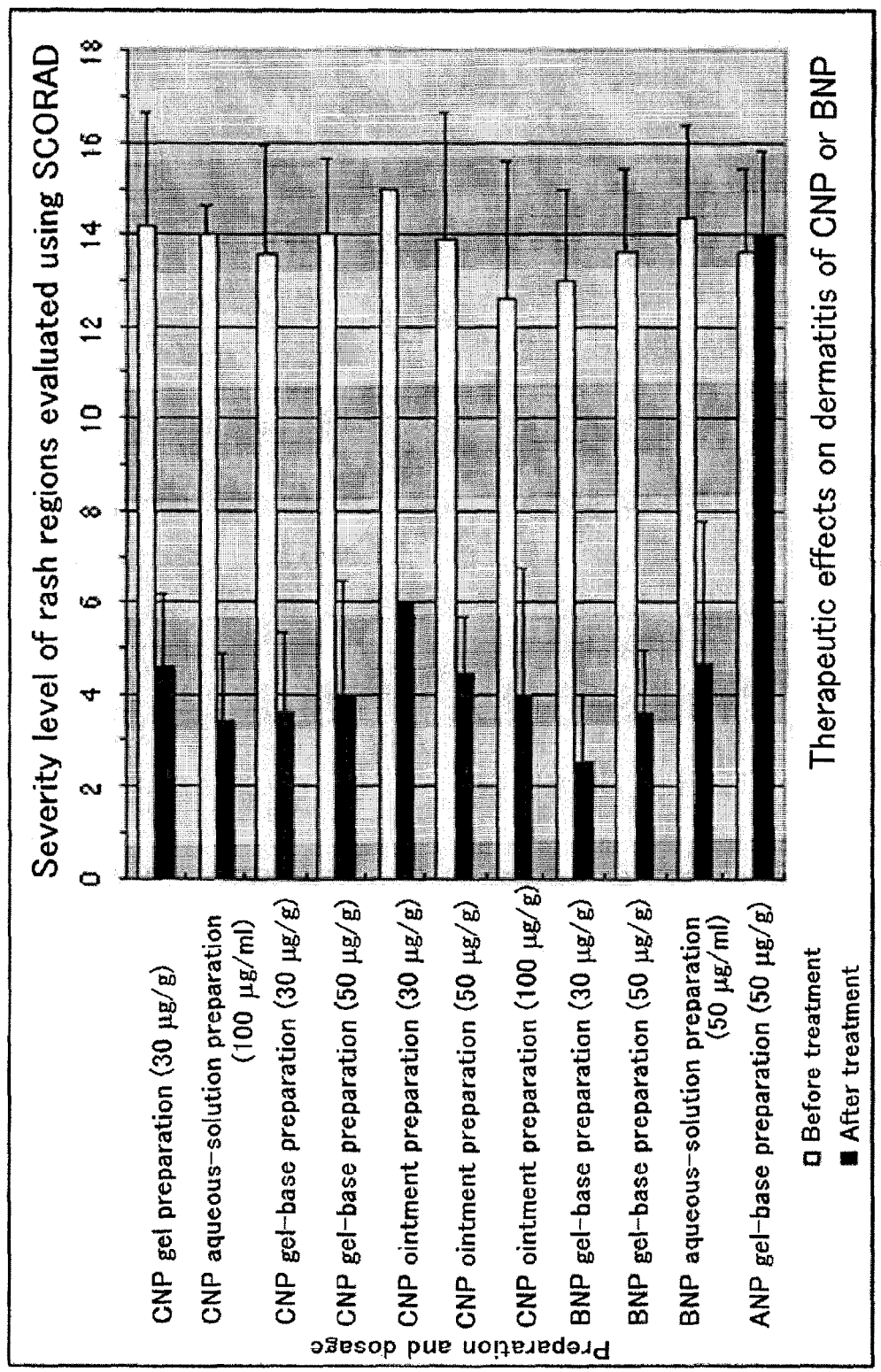
FIG. 19 is a graph showing the changes in the severity of the rashes evaluated using SCORAD before and after application of the skin external-preparation compositions comprising CNP or BNP of the present invention. The white bars represent severity levels before application, while the black bars represent severity levels after application. The length of the bars represents the average, and the lines extending from the end of the bars represent the standard deviation. The number of cases in each group is as follows: 5 cases in the CNP gel preparation (30 μg/g) group, 5 cases in the CNP aqueous-solution preparation (100 μg/ml) group, 7 cases in the CNP gel-base preparation (30 μg/g) group, 3 cases in the CNP gel-base preparation (50 μg/g) group, 1 case in the CNP ointment preparation (30 μg/g) group, 9 cases in the CNP ointment preparation (50 μg/g) group, 5 cases in the CNP ointment preparation (100 μg/g) group, 2 cases in the BNP gel-base preparation (30 μg/g) group, 5 cases in the BNP gel-base preparation (50 μg/g) group, 3 cases in the BNP aqueous-solution preparation (50 μg/ml) group, and 5 cases in the ANP gel-base preparation (50 μg/g) group.

In order to confirm the effects of the skin external-preparation composition of the present invention in overview, composite indices made by severity evaluation of rash regions based on SCORAD for each preparation were compared between before and after application, and the result of the comparison was expressed with a bar graph as shown in FIG. 19.

Severity levels of rash regions based on SCORAD compared between before and after application of the ANP gel-base preparations as comparative test examples showed almost no difference. In contrast, when the skin external-preparation compositions comprising CNP or BNP were used, the severity level of rash regions based on SCORAD was dramatically improved after application.

Figure 20:
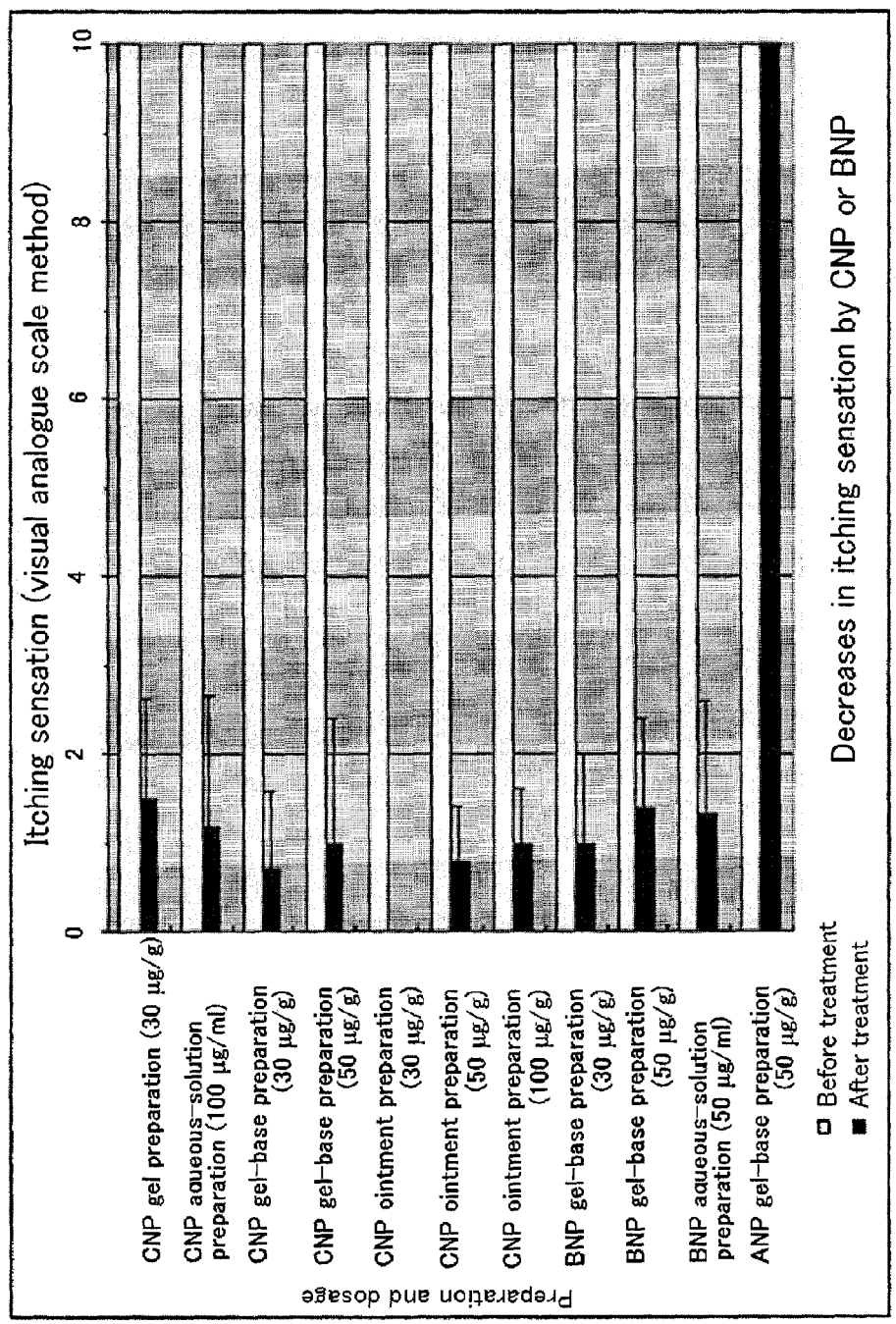
FIG. 20 is a graph showing the changes in the itching sensation subjectively evaluated by the participants using visual analogue scale method, before and after application of the skin external-preparation compositions comprising CNP or BNP of the present invention. The white bars represent the levels before application, while the black bars represent the levels after application. The length of the bars represents the average, and the lines extending from the end of the bars represent the standard deviation. The number of cases in each group is as follows: 5 cases in the CNP gel preparation (30 μg/g) group, 5 cases in the CNP aqueous-solution preparation (100 μg/ml) group, 7 cases in the CNP gel-base preparation (30 μg/g) group, 3 cases in the CNP gel-base preparation (50 μg/g) group, 1 case in the CNP ointment preparation (30 μg/g) group, 9 cases in the CNP ointment preparation (50 μg/g) group, 5 cases in the CNP ointment preparation (100 μg/g) group, 2 cases in the BNP gel-base preparation (30 μg/g) group, 5 cases in the BNP gel-base preparation (50 μg/g) group, 3 cases in the BNP aqueous-solution preparation (50 μg/ml) group, and 5 cases in the ANP gel-base preparation (50 μg/g) group.

Similarly, in order to confirm the effects of the skin external-preparation compositions of the present invention in a panoramic manner, itching sensation evaluated using visual analogue scale method for each preparation were compared between before and after application, and the result of the comparison was expressed with a bar graph, as shown in FIG. 20.

There was no change in the itching sensation before and after application of the ANP gel-base preparations as comparative test examples. In contrast, when the skin external-preparation compositions comprising CNP or BNP were used, the itching sensation level was dramatically improved after application.

Thus, the results shown in FIGS. 19 and 20 demonstrated that the skin external-preparation compositions comprising CNP or BNP of the present invention dramatically improved symptoms of atopic dermatitis.

INDUSTRIAL APPLICABILITY

The skin external-preparation compositions comprising CNP or BNP, in particular the therapeutic preparations for dermatitis, of the present invention, are extremely effective in the treatment of atopic dermatitis, which is recognized to have particularly-intractable nature. And the preparations of the present invention are capable of wide application. In addition, there is little concern of systemic side effects since CNP and BNP are originally intrinsic hormones, since the number of days of external application is only approximately 3 days, since an amount taken into the body through absorption from the skin upon being used as a topical medication is extremely small, and since a concentration used in the present invention is merely around 30 μg/g. The preparations of the present invention dramatically reduce subjective itching sensation without causing local irritation symptoms. Hence, the preparations of the present invention can be applied to patients in whom conventional steroids and tacrolimus were ineffective, as well as to patients and young subjects in whom steroids and tacrolimus cannot be used due to the concern of side effects. Moreover, the QOL of psoriasis patients who suffer from many scales can be improved.

Therefore, research and development as well as practical application of the present invention as novel therapeutic preparations for dermatitis can be greatly expected.

Furthermore, the preparations of the present invention have an efficacy as skin-care cosmetics that improve texture of the skin, since the effects with the preparations of the present invention that "the texture of the skin surface becomes finer, scales decrease, and the skin become soft to the touch" is important in compensating for skin dryness and the deterioration of barrier functions as well as preventing recurrence of inflammation, and since the preparations of the present invention exert the effects regardless of dosage form.

Namely, effects of anti-inflammation, horny cell layer care, epidermis care, and basal membrane care are observed, and in terms of clinical effects, improvement of elasticity and wrinkles of the skin, and moisturizing the skin are observed. From such a point of view, BNP therapeutic preparations for dermatitis of the present invention are also expected for their practical application as a skin-texture improving agent.

What is claimed is:

1. A method for treating dermatitis, comprising: externally applying a composition comprising an effective amount of a natriuretic peptide of C-type natriuretic peptide (CNP) or B-type natriuretic peptide (BNP) to skin of a subject in need of such treatment, wherein:
    said CNP comprises the human amino acid sequence of CNP-22 or CNP53, and
    said BNP comprises the human amino acid sequence of BNP-26, BNP-32, or BNP-45.

2. The method for treating dermatitis according to claim 1, wherein the natriuretic peptide is CNP-22.

3. The method for treating dermatitis according to claim 1, wherein the natriuretic peptide is BNP-32.

4. The method for treating dermatitis according to claim 1, wherein the composition comprises 1-500 µg/g of said C-type natriuretic peptide (CNP) or said B-type natriuretic peptide (BNP) based on the weight of the composition.

5. The method for treating dermatitis according to claim 1, wherein the composition comprises 20-200 µg/g of said C-type natriuretic peptide (CNP) or said B-type natriuretic peptide (BNP) based on the weight of the composition.

6. The method for treating dermatitis according to claim 1, wherein the composition comprises 30-100 µg/g of said C-type natriuretic peptide (CNP) or said B-type natriuretic peptide (BNP) based on the weight of the composition.

7. The method for treating dermatitis according to claim 1, wherein the dermatitis is selected from the group consisting of atopic dermatitis, dermatitis that led up to steroid dermatitis, steroid resistant dermatitis, dermatitis to which tacrolimus is not applicable, chronic dermatitis, erythroderma, eczema, contact dermatitis, seborrheic dermatitis, autosensitization dermatitis, stasis dermatitis, urticaria, drug eruption, dermal vasculitis, prurigo, pruritus cutaneus erythema, psoriasis, rosacea, rosacea like dermatitis, lichen planus, and follicular keratosis.

8. The method for treating dermatitis according to claim 1, wherein the dermatitis is an inflammation associated with at least one rash symptom selected from the group consisting of erythema, infiltrative erythema, lichenified lesion, scales, adhesion of crusts, eczema, abrasion, excoriation, prurigo nodularis, papule, erosions, infiltration, vesicle, and edema.

9. The method for treating dermatitis according to claim 1, wherein the dermatitis shows an immune reaction to at least one allergen selected from the group consisting of house dust, mites, cedar pollen, orchard grass pollen, ragweed pollen, egg white, and egg yolk.

10. The method for treating dermatitis according to claim 1, wherein the dermatitis occurs in at least one region selected from the group consisting of face, neck, back, and arms.

11. The method for treating deiinatitis according to claim 1, wherein the dosage form of the composition is selected from the group consisting of ointment, gel, cream, lotion, solution, spray, and patch.

12. A method for improving skin texture, comprising: externally applying a composition comprising an effective amount of a natriuretic peptide of C-type natriuretic peptide (CNP) or B-type natriuretic peptide (BNP) to skin of a subject in need of such treatment, wherein:
    said CNP comprises the human amino acid sequence of CNP-22 or CNP-53; and said BNP comprises the human amino acid sequence of BNP-26, BNP-32, or BNP-45.

13. The method for improving skin texture according to claim 12, wherein the natriuretic peptide is CNP-22.

14. The method for improving skin texture according to claim 12, wherein the natriuretic peptide is BNP-32.

15. The method for improving skin texture according to claim 12, comprising 1-500 µg/g of C-type natriuretic peptide (CNP) or B-type natriuretic peptide (BNP) based on the weight of the composition.

16. The method for improving skin texture according to claim 12, comprising 20-200 µg/g of C-type natriuretic peptide (CNP) or B-type natriuretic peptide (BNP) based on the weight of the composition.

17. The method for improving skin texture according to claim 12, comprising 30-100 µg/g of C-type natriuretic peptide (CNP) or B-type natriuretic peptide (BNP) based on the weight of the composition.

18. The method for improving skin texture according to claim 12, wherein improving skin texture is improving dry skin, rough skin, sensitive skin or fine wrinkles.

19. The method for improving skin texture according to claim 12, wherein the composition is a skin care product or a quasi drug.

20. The method for improving skin texture according to claim 12, wherein the dosage form of the composition is cream, foam, skin lotion, facial mask, skin-softening water, skin emulsion, foundation, makeup base, essence, soap, liquid cleanser, bath agent, sun-block cream, suntan oil or spray type liquid preparation.

* * * * *